US007122321B2

(12) United States Patent
Pantoliano et al.

(10) Patent No.: US 7,122,321 B2
(45) Date of Patent: Oct. 17, 2006

(54) HIGH THROUGHPUT METHOD FOR FUNCTIONALLY CLASSIFYING PROTEINS IDENTIFIED USING A GENOMICS APPROACH

(75) Inventors: Michael W Pantoliano, Avondale, PA (US); Francis R Salemme, Yardley, PA (US); Theodore E Carver, Jr., Thorndale, PA (US)

(73) Assignee: Johnson & Johnson Pharmaceutical Research & Development, L.L.C., Raritan, NJ (US)

( * ) Notice: Subject to any disclaimer, the term of this patent is extended or adjusted under 35 U.S.C. 154(b) by 409 days.

(21) Appl. No.: 10/057,940

(22) Filed: Jan. 29, 2002

(65) Prior Publication Data

US 2002/0168686 A1    Nov. 14, 2002

Related U.S. Application Data

(63) Continuation of application No. 09/190,128, filed on Nov. 12, 1998, now abandoned.

(60) Provisional application No. 60/065,129, filed on Nov. 12, 1997.

(51) Int. Cl.
   *G01N 33/53* (2006.01)
   *G01N 21/76* (2006.01)

(52) U.S. Cl. ............................ 435/7.1; 435/4; 435/7.4; 435/DIG. 1; 435/DIG. 14; 435/DIG. 41; 436/518; 530/350

(58) Field of Classification Search ................ 435/7.1, 435/7.4, 4, DIG. 1, DIG. 14, DIG. 41; 436/518, 436/501, 514; 530/300, 350
See application file for complete search history.

(56) References Cited

U.S. PATENT DOCUMENTS

| 4,580,895 A | 4/1986 | Patel ........................... 356/39 |
| 4,626,684 A | 12/1986 | Landa ......................... 250/328 |
| 4,628,026 A | 12/1986 | Gardell et al. ................. 435/7 |
| 4,774,055 A | 9/1988 | Wakatake et al. ............ 422/64 |
| 4,778,763 A | 10/1988 | Makiguchi et al. ........... 436/47 |
| 4,859,609 A | 8/1989 | Dull et al. ................... 436/501 |
| 4,880,750 A * | 11/1989 | Francoeur ................... 436/501 |
| 4,963,263 A | 10/1990 | Kauvar ....................... 210/635 |
| 5,096,807 A | 3/1992 | Leaback ........................ 435/6 |
| 5,133,866 A | 7/1992 | Kauvar ....................... 210/635 |
| 5,200,504 A | 4/1993 | Ghadiri ....................... 530/304 |
| 5,217,869 A | 6/1993 | Kauvar ....................... 435/7.9 |
| 5,255,976 A | 10/1993 | Connelly ..................... 374/31 |
| 5,260,207 A | 11/1993 | Pantoliano et al. ......... 435/221 |
| 5,290,513 A | 3/1994 | Berthold et al. .............. 422/52 |
| 5,300,425 A | 4/1994 | Kauvar ....................... 435/7.9 |
| 5,314,825 A | 5/1994 | Weyrauch et al. ............ 436/43 |
| 5,324,635 A | 6/1994 | Kawase et al. ............. 435/7.94 |
| 5,325,295 A | 6/1994 | Fratantoni et al. ..... 364/413.08 |
| 5,338,659 A | 8/1994 | Kauvar et al. ............... 435/2.1 |
| 5,340,474 A | 8/1994 | Kauvar ..................... 210/198.2 |
| 5,340,747 A | 8/1994 | Eden .......................... 435/172 |
| 5,355,215 A | 10/1994 | Schroeder et al. .......... 356/317 |
| 5,356,784 A | 10/1994 | Kauvar ....................... 435/7.9 |
| 5,383,023 A | 1/1995 | Walleczek ................... 356/417 |
| 5,409,611 A | 4/1995 | Kauvar ....................... 210/635 |
| 5,415,839 A | 5/1995 | Zaun et al. ................... 422/64 |
| 5,436,718 A | 7/1995 | Fernandes et al. ............ 356/73 |
| 5,463,564 A | 10/1995 | Agrafiotis et al. .......... 364/496 |
| 5,496,519 A | 3/1996 | Schacher ..................... 422/64 |
| 5,506,097 A | 4/1996 | Potter et al. ................... 435/4 |
| 5,525,300 A | 6/1996 | Danssaert et al. ............ 422/99 |
| 5,557,398 A | 9/1996 | Wechsler et al. ........... 356/318 |
| 5,567,317 A | 10/1996 | Kauvar ....................... 210/635 |
| 5,585,277 A | 12/1996 | Bowie et al. ................ 436/518 |
| 5,587,293 A | 12/1996 | Kauvar et al. ............. 435/7.21 |
| 5,589,351 A | 12/1996 | Harootunian ................ 435/29 |
| 5,599,504 A | 2/1997 | Hosoi et al. ............. 422/82.08 |
| 5,620,901 A | 4/1997 | Kauvar ....................... 436/518 |
| 5,631,734 A | 5/1997 | Stern et al. .................. 356/317 |
| 5,679,582 A | 10/1997 | Bowie et al. ................ 436/518 |
| 6,020,141 A | 2/2000 | Pantoliano et al. .......... 425/7.1 |
| 6,036,920 A | 3/2000 | Pantoliano et al. .......... 422/67 |
| 6,214,293 B1 | 4/2001 | Pantoliano et al. .......... 422/67 |
| 6,232,085 B1 | 5/2001 | Pantoliano et al. ......... 435/7.1 |
| 6,268,158 B1 | 7/2001 | Pantoliano et al. ......... 435/7.1 |

(Continued)

FOREIGN PATENT DOCUMENTS

EP          0 512 334 B1    11/1992

(Continued)

OTHER PUBLICATIONS

Websters's II New Riverside Dictionary (Riverside Publishing Col. 1994) p. 174 defintions: "biological" and "biology".*

(Continued)

*Primary Examiner*—Padmashri Ponnaluri
(74) *Attorney, Agent, or Firm*—Wison, Sonsini, Goodric & Rosati

(57) ABSTRACT

The present invention provides a method for functionally classifying a protein that is capable of unfolding due to a thermal change. The method comprises screening one or more of a multiplicity of different molecules for their ability to shift the thermal unfolding curve of the protein, wherein a shift in the thermal unfolding curve indicates that the molecule binds to the protein or affects the stability in a measurable way; generating an activity spectrum for the protein wherein the activity spectrum reflects a set of molecules, from the multiplicity of molecules, that shift the thermal unfolding curve, of the protein and therefore are ligands that bind to the protein, comparing the activity spectrum for the protein to one or more functional reference spectrum lists; and classifying the protein according to the set of molecules in the multiplicity of different molecules that shift the thermal unfolding curve of the protein.

13 Claims, 20 Drawing Sheets

U.S. PATENT DOCUMENTS

| | | | |
|---|---|---|---|
| 6,268,218 B1 | 7/2001 | Pantoliano et al. | 436/86 |
| 6,291,191 B1 | 9/2001 | Pantoliano et al. | 435/7.1 |
| 6,291,192 B1 | 9/2001 | Pantoliano et al. | 435/7.1 |
| 6,303,322 B1 | 10/2001 | Pantoliano et al. | 435/7.1 |
| 6,376,180 B1 | 4/2002 | Tomich et al. | |
| 2001/0003648 A1 | 6/2001 | Pantoliano et al. | |

FOREIGN PATENT DOCUMENTS

| | | |
|---|---|---|
| EP | 0 613 007 A2 | 8/1994 |
| EP | 0 640 828 A1 | 3/1995 |
| EP | 0 770 876 B1 | 4/2001 |
| WO | WO 92/03542 A1 | 3/1992 |
| WO | WO 93/14781 | 8/1993 |
| WO | WO 94/05394 | 3/1994 |
| WO | WO 95/18969 | 7/1995 |
| WO | WO 96/23879 | 8/1996 |
| WO | WO 97/09342 | 3/1997 |
| WO | WO 97/14038 | 4/1997 |
| WO | EP 0 770 876 A1 | 5/1997 |
| WO | WO 97/20952 | 6/1997 |
| WO | WO97/20952 A1 | 6/1997 |
| WO | WO 97/42500 | 11/1997 |
| WO | WO 98/15969 A2 | 4/1998 |
| WO | WO 98/39484 | 9/1998 |
| WO | WO 98/15969 A3 | 7/2000 |
| WO | WO 01/46693 A2 | 6/2001 |

OTHER PUBLICATIONS

Friguet, B., et al., "Immunochemical analysis of protein conformation," in: *Protein Structure: A Practical Approach*, Creighton, T.E., ed., IRL Press at Oxford University Press, Oxford, England, pp. 287-310 (1989).

Grant, S. K. et al., "Use of Protein Unfolding Studies to Determine the Conformational and Dimeric Stabilities of HIV-1 and SIV Proteases," *Biochemistry* 31:9491-9501, American Chemical Society (1992).

Hall, L. A., et al., "A High-Performance System for Automation of the Polymerase Chain Reaction," *BioTechniques* 10:102-103, 106-112, Eaton Publishing Co. (1991).

Harrington, J.F., "Spectroscopic Analysis of the Unfolding of Transition Metal-Ion Complexes of Human Lactoferrin and Transferrin," *Int. J. Biochem.* 24:275-280, Pergamon Press (1992).

Highuci, R., et al., "Simultaneous Amplification and Detection of Specific DNA Sequences," *Bio/Technology* 10:413-417, Nature Publishing Co. (1992).

Kennedy, M.W. et al., "The ABA-1 Allernen of the Parasitic Nematode Ascaris suum: Fatty Acid and Petinoid Binding Function and Structural: Characterization," *Biochemistry* 34:6700-6710, American Chemical Society (1995).

Kikuchi, T., et al., "Measurement of Chemiluminescence from Neutrophils in a 96-Well Microplate using Lumi Box U-800 II," *J. Biolum. Chemilum.* 12:149-153, John Wiley & Sons, Ltd. (May 1997).

Nilssen, B., "Proper and Improper Folding of Proteins in the Cellular Environment," *Annu. Rev. Microbiol.* 45:607-635, Annual Reviews, Inc. (1991).

Pan, P., "3.Sito Covalent Reactions Trigger Transitions between Open and Closed Conformations of the Trypuophan Synthase Bienzyme Complex," *Biochemistry* 35:5002-5013, American Chemical Society (1996).

Randall, L. L., "Peptide Binding by Chaperone SecB: Implications for Recognition of Nonnative Structure," *Science* 257:241-245, American Association for the Advancement of Science (1992).

Rosengart, T.K., et al., "Heparin Protects Heparin-Binding Growth Factor-I from Proteoiytic Inactivation *In Vitro*," *Biochem. Biophys. Res. Commun.* 152:432-440, Academic Press, Inc. (1988).

Sackett, D. L. et al., "Local Unfolding and the Stepwise Loss of the Functional Properties of Tubulin," *Biochemistry* 33:11868-11878, American Chemical Society (1994).

Tanigaki, N. et al., "Unfolded HLA Class I α Chains and Their Use in an Assay of HLA Class-I-Peptide Binding," *Hum. Immunol.* 36:119-127, Elsevier Science (1993).

Volkin, D. B. and Klibanov, A.M., "Mechanism of Thermoinactivation of Immobilized Glucose Isomerase," *Biotech. Bioengin.* 33:1104-1111, John Wiley & Sons, Inc. (1989).

Petreila, E., "A Miniaturized Thermal Shift Assay Technology for Directly Evaluating Targets Derived from Genomics," poste: presented at the Society for Biomolecular Screening Annual Meeting, Edinburgh, Scotland (Sep. 1999).

Molecular Probes, Inc. website search results for "dapoxyl," 11 pages (Mar. 1998).

Bagshaw, C. F. and D. A. Harris, "Chapter 4. Measurement of Ligand Binding t. Proteins," in *Spectrophotonetry & spectrofluorimetry: a practical approach*, Bashford, C. L. and D. A. Harris, eds., IRL Press, Washington, DC, pp. 91-11 (1987).

Barcelo, F. et al , "A Scanning Calorimetric Study of Natural DNA and Antitumoral Anthracycline Antibiotic-DNA Complexes," *Chem. -Biol. Interactions* 74:315-324, Elsevier Scientific Publishers Ireland Ltd. (1990).

Bell, J.E., "Chapter 4. Fluorescence: Solution Studies," in *Spectroscopy in Biochemistry*, vol. 1, J. E. Bell, ed., CPC Press, Inc., Boca Raton, FL, pp. 155-194 1981.

Bergdoll, M., et al., "All in the family: Structural and evolutionary relationships among three modular proteins with diverse functions and variable assembly," *Protein Sci.* 7:1661-1670, Cambridge University Press (Aug. 1998).

Blattner, F.R., et al., "The Complete Genome Sequence of *Escherichia coli* K-12," *Science* 277:1453-1462, American Association for the Advancement of Science (Sep. 1997).

Bouvier, M. and D. C. Wiley, "Importance of Peptide Amino and Carboxyl Termini to the Stability of MHC Class I Molecules," *Science* 165:398-402, American Association for the Advancement of Science (1994).

Brand, L. and J. R. Gohlke, "Fluorescence Probes for Structure," *Ann. Rev. Biochem.* 41:843-868, Annual Reviews Inc. (1972).

Brandts, J.F. and L. -N. Lin, "Study of Strong to Ultratight Protein Interactions Using Differential Scanning Calorimetry," *Biochemistry* 29:6927-6940, American Chemical Society (1990).

Chavan, A.J. and B.E. Haley, "Interaction of Nucleotides with Acidic Fibroblast Growth Factor FGF-1," *Biochemistry* 33:7193-7202, American Chemical Society (1994).

Clegg, R.M. et al., "Observing the helical geometry of double-stranded DNA in solution by fluorescence resonance energy transfer," *Proc. Natl. Acad. Sci. USA* 90:2994-2998, The National Academy of Science (1993).

Davidson, A.R. et al., "Cooperatively folded proteins in random sequence libraries," *Nature Structural Biol.* 2:856-864, Nature Publishing Group (1995).

Denessiouk, K.A. et al., "Enzyme-menonucleotide interactions: Three different folds share common structural elements for ATP recognition," *Protein Sci.* 7:1765-1771, Cambrdige University Press, Aug. 1998.

Dennis, S. et al., "Use of fragments of hirudin to investigate thrombin-hirudin interaction," *Eur. J. Biochem* 188:61-66, Springer International and the Federation of European Biochemical Societies (1990).

Diwu, Z. et al., "Fluorescent Molecular Probes. II. The Synthesis, Spectral Properties and Use of Fluorescent Solvatochromic Dapoxyl Dyes," *Photochem. & Photobiol.* 66:424-431, American Society for Photobiology (Oct. 1997).

Eftink, M.P. et al., "The Use of Fluorescence Methods to Monitor Unfolding Transitions in Proteins," *Biophys. J.* 66:482-501, The Biophysical Society (1994).

Fraser, C.M. et al., "Complete Genome Sequence of *Treponema pallidum*, the Syphilis Spirochete," *Science* 281:375-388, American Association for the Advancement of Science (Jul. 1998).

Hieter, P. and Boguski, M., "Functional Genomics: It's All How You Read It," *Science* 278:601-602, American Association for the Advancement of Science (Oct. 1997).

Hogg, P.J. and Jackson, C. M., "Fibrin monomer protects thrombin from inactivation by heparin-antithrombin III: Implications for heparin efficacy," *Proc. Natl. Acad. Sci. USA* 86:3619-3623, National Academy of Sciences (1989).

Hogg, P.J. and Jackson, C.M., "Formation of a Ternary Complex between Thrombin, Fibrin Monomer, and Heparin Influences the Action of Thrombin on Its Substrates," *J. Biol. Chem.* 265:248-255, American Society for Biochemistry and Molecular Biology, Inc. (1990).

Hotchkiss, K. A., et al., "Inhibition of Heparin Activity in Plasma by Soluble Fibrin: Evidence for Ternary Thrombin-Fibrin-Heparin Complex Formation," *Blood* 64:498-503, W.B. Saunders Company (1994).

Janknecht, P., et al., "Rapid and efficient purification of native histidine-tagged protein expressed by recombinant vaccinia virus," *Proc. Natl. Acad. Sci. USA* 88:8972-8976, National Academy of Sciences (1991).

Kan, M. et al., "An Essential Heparin-Binding Domain in the Fibroblast Growth Factor Receptor Kinase," *Science* 259:1918-1921, American Association for the Advancement of Science (1993).

Lewis, M. et al., "Crystal Structure of the Lactose Operon Repressor and Its Complexes with DNA and Inducer," *Science* 271:1247-1254, American Association for the Advancement of Science (1996).

Mersen, A. et al., "Energetic Origins of Specificity of Ligand Binding in an Interior Nonpolar Cavity of T4 Lysozyme," *Biochemistry* 34:8564-8575, American Chemical Society, (1995).

Nakatani, H., et al., "Temperature-jump Studies on Benzeneboronic Acid-Serine Protease Interactions," *J. Biochem.* 77:905-908, The Japanese Biochemical Society (1975).

Pantoliano, M.W., et al., "Multivalent Ligand-Receptor Binding Interactions in the Fibroblast Growth Factor System Produce a Cooperative Growth Factor and Heparin Mechanism for Receptor Dimerization," *Biochemistry* 33:10229-10248, American Chemical Society (1994).

Pennisi, E., "Laboratory Workhorse Decoded," *Science* 277:1432-1434, American Association for the Advancement of Science (Sep. 1997).

Qasba, P.K. and Kumar, S., "Molecular Divergence of Lysozymes and α-Lactalbumin," *Crit. Rev. Biochem. Mol. Biol.* 32:255-306, CRC Press LLC (Dec. 1997).

Rowen, L. et al., "Sequencing the Human Genome," *Science* 278:605-607, American Association for the Advancement of Science (Oct. 1997).

Schellman, J.A., "Macromolecular Binding," *Biopolymers* 14:999-1018, John Wiley & Sons, Inc. (1975).

Schellman, J.A., "Communications to the Editor. The Effect of Binding on the Melting Temperature of Biopolymers," *Biopolymers* 15:999-1000, John Wiley & Sons, Inc. (1976).

Schellman, J.A., "The relation between the free energy of interaction and binding," *Biophys. Chem.* 45:273-279, Elsevier Science Publishers B. V. (1993).

Tapparelli, C. et al., "*In Vitro* and *In Vivo* Characterization of a Neutral Boron-containing Thrombin Inhibitor," *J. Biol. Chem.* 268:4734-4741, American Society for Biochemistry and Molecular Biology, Inc. (1993).

Tatusov, R.L. et al., "A Genomic Perspective on Protein Families," *Science* 278:631-637, American Association for the Advancement of Science (Oct. 1997).

Tong, L. et al., "Conserved mode of peptidomimetic inhibition and substrate recognition of human cytomegalovirus protease," *Nature Structural Biol.* 5:819-826, Nature Publishing Co. (Sep. 1998).

Vijayalakshmi, J. et al., "The isomorphous structures of prethrombin2, hirugen-, and PPACF-thrombin: Changes accompanying activation and exosite binding to thrombin," *Protein Sci.* 3:2264-2271, Cambridge University Press and The Protein Society (1994).

Weber, P. C. et al., "Structure-Based Design of Synthetic Azobenzene Ligands for Streptavidin," *J. Am. Chem. Soc.* 116:2717-2724, American Chemical Society (1994).

Wiseman, T. et al., "Rapid Measurement of Binding Constants and Heats of Binding Using a New Titration Calorimeter," *Anal. Biochem.* 179:131-137, Academic Press Inc. (1989).

Pricelist of Products from BioProbes 25, New Products and Applications Catalog, Molecular Probes, Inc., Eugene, Oregon, pp. 8-9 (May 1997).

Becktel, W.J. and Schellman, J.A., "Protein Stability Curves," *Biopolymers* 26:1859-1877, John Wiley & Sons, Inc. (1987).

Belevitch, G.V. et al., "Calcium antagonists, Riodipine, Hiphedipine and Verapamil, Binding to Model and Biological Membranes: Fluorescence Analysis," *Biologicheskie Membrany* 5:768-776, Rossiiskaya Akademiya Nauk (1988).

Bone, R. et al., "Inhibition of Thymidine Kinase by $P^1$-(Adenosine-5')-P-(thymidine-5')-pentaphosphate," *J. Biol. Chem.* 261:5731-5735. The American Society of Biological Chemists, Inc. (1986).

Bowie, J.U. and Sauer, R.T., "Equilibrium Dissociation and Unfolding of the Arc Repressor Dimer," *Biochemistry* 28:7139-7143, American Chemical Society (1989).

Brandts, J.F. et al., "An instrument for rapid determination of binding constants for biomolecules," *Amer. Lab.* 22:30-41, International Scientific Communications, Inc. (1990).

Buchner, J. et al., "Alternatively Folded States of an Immunoglobulin," *Biochemistry* 30:6922-6929, American Chemical Society (1991).

Burke, C.J. et al., "Effect of Polyanions on the Unfolding of Acidic Fibroblast Growth Factor," *Biochemistry* 32:6419-6426, American Chemical Society (1993).

Butour, J.-L. et al., "Effect of the amine non-leaving group on the structure and stability of DNA complexes with cis-[Pt $(R-NH_1)_1$ $(NO_1)_1$]," *Eur. J. Biochem.* 202:975-980, Springer International and the Federation of European Biochemical Societies (1991).

Chen, L. et al., "Microtiter Plate Binding Assay for Cholinergic Compounds Utilizing the Nicotinic Acetylcholine Receptor," *Anal. Chem.* 64:3018-3023, American Chemical Society (1992).

Copeland, R.A. et al., "The Structure of Human Acidic Fibroblast Growth Factor and Its Interaction with Heparin," *Arch. Biochem. Biophys.* 289:53-61, Academic Press, Inc. (1991).

Cox, M.J. and Weber, P.C., "An Investigation of Protein Crystallization Parameters Using Successive Automated Grid Searches (SAGS)," *J. Crystal Growth* 90:318-324, Elsevier Science Publishers B.V. (1988).

Darzynkiewicz, Z. et al., "DNA Denaturation *In Situ*: Effect of Divalent Cations and Alcohols," *J. Cell Biol.* 68:1-10, Rockefeller University Press (1976).

Draper, D.E. and Gluick, T.C., "Melting Studies of RNA Unfolding and RNA-Ligand Interactions," *Meth. Enzymol.* 259:281-305. Academic Press, Inc. (1995).

Elwell, M. and Schellman, J., "Phage T4 Lysozyme Physical Properties and Reversible Unfolding," *Biochim. Biophys. Acta* 386:309-323, Elsevier Scientific Publishing Company (1975).

Elwell, M.L. and Schellman, J.A., "Stability of Phage T4 Lysozymes. I. Native Properties and Thermal Stability of Wild Type and Two Mutant Lysozymes," *Biochim. Biophys. Acta.* 494:367-383, Elsevier/North-Holland Biomedical Press (1977).

Eriksson, A.E. et al., "Similar Hydrophobic Replacements of Leu99 and Phe153 within the Core of T4 Lysozyme Have Different Structural and Thermodynamic Consequences," *J. Mol. Biol.* 229:747-769, Academic Press, Inc. (1993).

Freire, E., "Thermal Denaturation Methods in the Study of Protein Folding," *Meth. Enzymol.* 259:144-168, Academic Press, Inc. (1995).

Fukada, H., "Calorimetry of the Ligand Binding to Proteins," *Tanpakushitsu Kakusan Koso* 33:328-336, Kyoritsu Shuppan Co. Ltd. (1988).

Gordon, E.M. et al., "Applications of Combinatorial Technologies to Drug Discovery. 2. Combinatorial Organic Synthesis, Library Screening Strategies, and Future Directions," *J. Med. Chem.* 37:1385-1401, American Chemical Society (1994).

Green, S M. et al., "Roles of Metal Ions in the Maintenance of the Tertiary and Quaternary Structure of Arginase from *Saccharomyces cerevisiae*," *J. Biol. Chem.* 266:21474-21481, American Society for Biochemistry and Molecular Biology (1991).

Hanna, M. and Szostak, J.W., "Suppression of mutations in the core of the *Tetrahymena ribozyme* by spermidine, ethanol and by substrate stabilization," *Nucl. Acids Res.* 22:5326-5331, Oxford University Press (1994).

Hei, D.J. and Clark, D.S., "Estimation of Melting Curves From Enzymatic Activity-Temperature Profiles," *Biotechnol. Bioeng.* 42:1245-1251, John Wiley & Sons, Inc. (1993).

Higuchi, R. et al., "Kinetic PCR Analysis: Real-time Monitoring of DNA Amplification Reactions," *Bio/Technology* 11:1026-1030, Nature Publishing Company (1993).

Hofmann, A. et al., "A Sparse Matrix Screen to Establish Initial Conditions for Protein Renaturation," *Anal. Biochem.* 230:8-15, Academic Press, Inc. (1995).

Hutton, J.R., "Renaturation kinetics and thermal stability of DNA in aqueous solutions of formamide and urea," *Nucl. Acids Res.* 4:3537-3555, Information Retrieval Limited (1977).

Iida, K., "Structure and biological activity of complement receptors CR1, CR2 and CR3," *Seikagaku* 58: 1471-1474, Nihon Seikagakkai (1986).

Jensen, D.E. and von Hippel, P.H., "DNA 'Melting' Proteins: I. Effects of Bovine Pancreatic Ribonuclease Binding on the Conformation and Stability of DNA," *J. Biol. Chem.* 251:7198-7214, American Society of Biological Chemists, Inc. (1976).

Johnson, C.M. et al., "Differential Scanning Calorimetry of Thermal Unfolding of the Methionine Repressor Protein (MetJ) from *Escherichia coli*," *Biochemistry* 31:9717-9724, American Chemical society (1992).

Kogtev, L.S. et al., "Use of Fluorescence-Labeled Lipid Probes for Analyzing Substance P and its Derivatives Binding to the Rat Brain Tachykinin Receptors," *Biologicheskie Membrany* 6:34-41, Rossiiskaya Akademiya Nauk (1989).

Kuroki, R. and Inaka, K., "Stabilization of a Protein by Constructing a Ligand Binding Side," *Tanpakushitsu Kakusan Koso* 37: 314-321, Kyoritsu Shuppan Co. Ltd. (1992).

Kuwajima, K., "Kinetic pathway of globular-protein folding," *Seikagaku* 62:117-121, Nihon Seikagakkai (1990).

Lapadat, M.A. and Spremulli, L.L., "Effect of Guanine Nucleotides on the Conformation and Stability of Chloroplast Elongation Factor Tu," *J. Biol. Chem.* 264:5510-5514, The American Society for Biochemistry and Molecular Biology, Inc. (1989).

Lee, M. et al., "In Vitro Cytotoxicity of GC Sequence Directed Alkylating Agents Related to Distamycin," *J. Med. Chem.* 36:863-870, American Chemical Society (1993).

Lennick, M. et al., "Changes in Protein Conformation and Stability Accompany Complex Formation between Human C1 Inhibitor C1s," *Biochemistry* 24:2561-2568, American Chemical Society (1985).

Lin, L.-N. et al., "Calorimetric Studies of Serum Transferrin and Ovotransferrin. Estimates of Domain Interactions, and Study of the Kinetic Complexities of Ferric Ion Binding," *Biochemistry* 33:1881-1888, American Chemical Society (1994).

Ma, C. -Y. and Harwalkar, v.R., "Effects of Medium and Chemical Modification on Thermal Characteristics of β-Lactoglobulin," *J. Thermal Analysis* 47:1513-1525, John Wiley & Sons, Ltd (Nov. 1996).

Mach, H. et al., "Effect of Polyanions on the Folding and Unfolding of Acidic Fibroblast Growth Factor," in *Harnessing Biotechnology for the 21st Century. Proceedings of the Ninth International Biotechnology Symposium and Exposition*, Ladisch, M. R. and Bose, A., Eds., American Chemical Society, Washington, DC, pp. 290-293 (1992).

Mach, H. et al., "Nature of the Interaction of Heparin with Acidic Fibroblast Growth Factor," *Biochem.* 32:5480-5489, American Chemical Society (1993).

Mach, H. et al., "Partially Structured Self-Associating States of Acidic Fibroblast Growth Factor," *Biochem.* 32:7703-7711, American Chemical Society (1993).

Manevich, E.M. et al., "The binding of the B-chain of ricin to Burkitt lymphoma cells," *FEBS Lett.* 194:313-316, Elsevier Science Publishers B.V. (1986).

Markovic-Housley, Z. and Garavito, R.M., "Effect of temperature and low pH on structure and stability of matrix porin and micellar detergent solutions," *Biochim. Biophys. Acta* 869:158-170, Elsevier Science Publishers B.V. (1986).

Marquis-Omer, D. et al., "Stabilization of the FK506 Binding Protein by Ligand Binding," *Biochem. Biophys. Res. Commun.* 179:741-748, Academic Press, Inc. (1991).

Merabet, E.K. et al., "Differential scanning calorimetric study of 5-enolpyruvoyl shikimate-3-phosphate synthase and its complexes with shikimate-3-phosphate and glyphosate: irreversible thermal transitions," *Biochim. Biophys. Acta* 1161:272-278. Elsevier Science Publishers B.V. (1993).

Middaugh, C.R. et al., "Nature of the Interaction of Growth Factors with Suramin," *Biochemistry* 31:9016-9024, American Chemical Society (1992).

Middaugh, C.R. et al., "Selected Problems in the Formulation of Protein Pharmaceuticals," *Book of Abstracts of the 205th ACS National Meeting*, Abstract No. 126, American Chemical Society (1993).

Molotkovskaya, I.M. et al., "Immunosuppressive Activity of Glycosphingolipids: A Study of the Interaction of Interleukin-2 with Gangliosides Using Cells and Model Systems," *Biologicheskie Membrany* 9:143-151, Rossiiskaya Akademiya Nauk (1992).

Molotkovskaya, I.M. et al., "The Concanavalin A Binding By Plasma Membranes of Young and Old Mouse Lymphocytes: A Fluorescent Probe Study," *Biologicheskie Membrany* 9:32-39, Rossiiskaya Akademiya Nauk (1992).

Muriana, F.J.G. et al., "Further thermal characterization of an aspartate aminotransferase from a halophilic organism," *Biochem. J.* 298:465-470, The Biochemical Society (1994).

Murry-Brelier, A. and Goldberg, M.E., "A physical-chemical and immunological comparison shows that native and renatured *Escherichia coli* tryptophan synthase $R^2$ subunits are identical," *Biochimie* 71:533-543, Société de Chimie biologique and Elsevier Science Publishers (1989).

Otto, A. and Seckler, R., "Characterization, stability and refolding of recombinant hirudin," *Eur. J. Biochem.* 202:67-73, Springer International and the Federation of European Biochemical Societies (1991).

Pace, C.N. and Grimsley, G.R., "Ribonuclease T. Is Stabilized by Cation and Anion Binding," *Biochemistry* 27:3242-3246, American Chemical Society (1988).

Pace, C.N. and Marshall, H.F., Jr., "A Comparison of the Effectiveness of Protein Denaturants for β- Lactoglobulin and Ribonuclease," *Arch. Biochem. Biophys.* 199:270-276, Academic Press, Inc. (1980).

Pakula, A.A. and Sauer, R.T., "Amino Acid Substitutions That Increase the Thermal Stability of the λ Cro Protein," *Proteins* 5:202-210, Alan R. Liss, Inc. (1989).

Pakula, A.A. and Sauer, R.T., "Genetic Analysis of Protein Stability and Function," *Annu. Rev. Genet.* 23:289-310, Annual Reviews Inc. (1989).

Pakula, A.A., "A Genetic and Biochemical Analysis of the Bacteriophage λ Cro Protein," Doctoral Thesis, Department of Biology, Massachusetts Institute of Technology (1988).

Pantoliano, M.W., "Automated Receptor Screening By Thermal Physical Assays," Department of Health and Human Services Small Business Research Program Phase I Grant Application (May 1995).

Pantoliano, M.W., "Automated Receptor Screening By Thermal Physical Assays," Department of Health and Human Services Small Business Research Program Phase II Grant Application (Sep. 1996).

Pilch, D.S. et al., "Characterization of a Triple Helix-specific Ligand: BePI <3-methody-7H-8-methyl-11-((3'-amino)propylamino>benzo[e]pyrido[4, 3-b]indole) Intercalates into Both Double-helical and Triple-helical DNA," *J. Mol. Biol.* 232:926-946, Academic Press, Inc. (1993).

Pilch, D.S. and Breslauer, K.J., "Ligand-induced formation of nucleic acid triple helices," *Proc. Natl. Acad. Sci. USA* 91:9332-9336, The National Academy of Sciences of the USA (1994).

Pörschke, D. and Jung, M., "Stability decrease of RNA double helices by phenylalanine-, tyrosine- and tryptophane-amides. Analysis in terms of site binding and relation to melting proteins," *Nucl. Acids Res.* 10:6163-6176, IRL Press Ltd (1982).

Porter, P.N. et al., "Stabilization of $SV_4$, transformed human fibroblast cytoplasmic thymidine kinase by ATP," *Mol. Cell. Biochem.* 35:59-64, Martinus Nijhoff/Dr. W. Junk Publishers b. v. (1980).

Privalov, P.L., "Thermal Investigations of Biopolymer Solutions and Scanning Microcalorimetry," *FEBS Lett.* 40(Suppl.) :S140-S153, North-Holland Publishing Company (1974).

Rakhaminova, A.B. et al., "Model for Auxin Receptor," *Biokhimiya* 43:806-823, Rossiiskaya Akademiya Nauk (1978).

Rakhaminova, A.B. et al., "Construction of a Model of the Auxin Receptor," *Biorak* 43:639-653, Plenum Publishing (1978).

Ramalingam, K. et al., "Conformational Studies of Anionic Melittin Analogues: Effect of Peptide Concentration, pH, Ionic Strength, and Temperature—Models for Protein Folding and Halophilic Proteins," *Biopolymers* 32:981-992, John Wiley & Sons, Inc. (1992).

Ramsay, G. and Eftink, M.R., "A Multidimensional Spectrophotometer for Monitoring Thermal Unfolding Transitions of Macromolecules," *Biophysical J.* 31:516-523, The Biophysical Society (1994).

Roy, K. B. et al., "Hairpin and Duplex Forms of a Self-Complementary Dodecamer, d-AGATCTAGATCT, and Interaction of the Duplex Form with the Peptide KGWGK: Can a Pentapeptide Destabilize DNA?," *Biochemistry* 31:6241-6245, American Chemical Society (1992).

Sagar, S.L. and Domach, M.M., "Thermostability of Drifted Oligomeric, Reduced, and Refolded Proteins," Chapter 5 in *ACS Symposium Series: Protein Refolding*, Georgiou, G. and De Bernardez-Clark, E., Eds., American Chemical Society, Washington, DC, pp. 64-78 (1991).

Schellman, J.A., "The Thermodynamics of Solvent Exchange," *Biopolymers* 34:1015-1026, John Wiley & Sons, Inc. (1994).

Schellman, J.A., "The Thermodynamic Stability of Proteins," *Ann. Rev. Biophys. Biophys. Chem.* 16:115-137, Annual Reviews, Inc. (1987).

Schellman, J.A., "A simple model for solvation in mixed solvents. Applications to the stabilization and destabilization of macromolecular structures," *Biophys. Chem.* 37:121-140, Elsevier Science Publishers B. V. (1990).

Schellman, J.A., "Fluctuation and Linkage Relations in Macromolecular Solution," *Biopolymers* 29:215-224, John Wiley & Sons, Inc. (1990).

Schwarz, F.P. et al., "Thermodynamics of the Binding of Galactopyranoside Derivatives to the Basic Lectin from Winged Bean (*Psophocarpus tetrogonolobus*)," *J. Biol. Chem.* 266:24344-24350, American Society for Biochemistry and Molecular Biology, Inc. (1991).

Shchyolkina, A.K. et al., "The R-Form of DNA does exist," *FEBS Lett.* 339:113-118, Elsevier Science Publishers B. V. (1994).

Shrake, A. et al., "Partial Unfolding of Dodecameric Glutamine Synthetase from *Escherichia coli*: Temperature-Induced, Reversible Transitions of Two Domains," *Biochemistry* 28:6281-6294, American Chemical Society (1989).

Smirnov, O.N. et al., "Study on the Interaction of the Cholera Toxin and Its B-Subunit with Liposomes Containing Ganglioside GM1 and Fluorescent-Labeled Gangliosides," *Biologicheskie Membrany* 12:174-184, Rossiiskaya Akademiya Nauk (1995).

Sominsky, V.N. et al., "Using a Fluorescent Probe for Investigating β-Adrenoreceptive Function of Human Blood Erythrocytes," *Biofizika* 30:642-645, Rossiiskaya Akademiya Nauk (1985).

Surin, A. M., et al., "A Study of the Interaction of Cholera Toxin B-Subunit with Liposomes Containing Ganglioside GM1 and Fluorescence-Labeled Lipids," *Biologicheskie Membrany* 9:495-508, Rossiiskaya Akademiya Nauk (1992).

Tachibana, H. et al., "Relationship between the Optimal Temperature for Oxidative Refolding and the Thermal Stability of Refolded State of Hen Lysozyme Three-Disulfide Derivatives," *Biochemistry* 33:15008-15016, American Chemical Society (1994).

Takahashi, N., "Cyclophilin and FK506-binding protein," *Seikagaku 64*: 325-331, Nihon Seikagakkai (1992).

Timasheff, S.N. and Arakawa, T., "Stabilization of protein structure by solvents," Chapter 14 in *Protein Structure, a practical approach*, Creighton, T. E., Ed., IRL Press, Oxford, England, pp. 331-345 (1994).

Timofeev, A. A. et al., "The Use of Spectral Characteristics of Ryodipine for the Study of Dihydropyridine Receptor Complex in Neuronal Membranes," *Byull. Eksp. Biol. Med. 114*: 29-32, Rossiiskaya Akademiya Meditsinskikh Nauk (1992).

Tsai, P.K. et al., "Formulation Design of Acidic Fibroblast Growth Factor," *Pharm. Res. 10*: 649-659, Plenum Press (1993).

Viguera, A.R. et al., "Thermodynamic and Kinetic Analysis of the SH3 Domain of Spectrin Shows a Two-State Folding Transition," *Biochemistry* 33:2142-2150, American Chemical Society (1994).

Volkin, D.B. and Klibanov, A.M., "Mechanism of Thermoinactivation of Immobilized Glucose Isomerase," *Biotech. Bioengin.* 33:1104-1111, John Wiley & Sons, Inc. (1989).

Volkin, D.B. et al., "The Effect of Polyanions on the Stabilization of Acidic Fibroblast Growth Factor," in *Harnessing Biotechnology for the 21st Century, Proceedings of the Ninth International Biotechnology Symposium and Exposition*, Ladisch, M.R. and Bose, A., Eds., American Chemical Society, Washington, DC, pp. 298-302 (1992).

Volkin, D.B. et al., "Physical Stabilization of Acidic Fibroblast Growth Factor by Polyanions," *Arch. Biochem. Biophys.* 300:30-41, Academic Press, Inc. (1993).

Volkin, D.B. et al., "Sucralfate and soluble sucrose octasulfate bind and stabilize acidic fibroblast growth factor," *Biochim. Biophys. Acta.* 1203:18-26, Elsevier Science Publishers B.V. (1993).

Wagenhöfer, M. et al., "Thermal Denaturation of Engineered Tet Repressor Proteins and Their Complexes with tet Operator and Tetracycline Studied by Temperature Gradient Gel Electrophoresis," *Anal. Biochem.* 175:422-432, Academic Press, Inc. (1988).

Walz, F.G. and Kitareewan, S., "Spermine Stabilization of a Folded Ribonuclease $T_1$," *J. Biol. Chem.* 265:7127-7137, The American Society for Biochemistry and Molecular Biology, Inc. (1990).

Waring, M.J. and Henley, S.M., "Stereochemical aspects of the interaction between steroidal diamines and DNA," *Nucl. Acids Res.* 2:567-586, IRL Press (1975).

Waring, M.J., "Stabilization of Two-Stranded Ribohomopolymer Helices and Destabilization of a Three-Stranded Helix by Ethidium Bromide," *Biochem. J.* 143:483-486, The Biochemical Society (1974).

Zahnley, J.C., "Effects of Manganese and Calcium on Conformational Stability of Concanavalin A: A Differential Scanning Calorimetric Study," *J. Inorg. Biochem.* 15:67-78, Elsevier North Holland (1981).

Zolkiewski, M. and Ginsburg, A., "Thermodynamic Effects of Active-Site Ligands on the Reversible, Partial Unfolding of Dodecameric Glutamine Synthetase from *Escherichia coli*: Calorimetric Studies," *Biochemistry* 31:11991-12000, American Chemical Society (1992).

Partial English translation of Fukada, H., "Calorimetry of the Ligand Binding to Proteins," *Tanpakushitsu Kakusan Koso* 33:328-336, Kyoritsu Shuppan Co. Ltd. (1988).

English translation of Kogtev, L.S. et al., "Use of Fluorescein-Labeled Lipid Probes for Analyzing Substance P and its Derivatives Binding to the Rat Brain Tachykinin Receptors," *Biologicheskie Membrany* 6:34-41, Rossiiskaya Akademiya Nauk (1989).

Partial English translation of Kuroki, R. and Inaka, K., "Stabilization of a Protein by Constructing a Ligand Binding Site," *Tanpakushitsu Kakusan Koso* 37:314-321, Kyoritsu Shuppan Co. Ltd. (1992).

Partial English translation of Kuwajima, K., "Kinetic pathway of globular-protein folding," *Seikagaku* 63:117-121, Nihon Seikagakkai (1990).

Pantoliano, M.W., "A Miniaturized Thermal Shift Assay Technology for Directly Evaluating Targets Derived from Genomics," poster presented at the Society For Biomolecular Screening Annual Meeting, Baltimore, MD (Sep. 1998).

Herrero, M.E. and Castell, J.V., "Fluorometric Microassay to Quantify Microsomal Epoxide Hydrolase in 96-Well Plates,"0 *Anal. Biochem.* 230:154-158, Academic Press, Inc. (1995).

Mansfield, E.S. et al., "Nucleic acid detection suing non-radioactive labeling methods," *Mol. Cell. Probes* 9:145-156, Academic Press Limited (1995).

Martin, C.S. and Bronstein. I., "Imaging of Chemiluminescent Signals with Cooled CCD Camera Systems," *J. Biolum. Chemilum.* 9:148-183, John Wiley & Sons, Ltd. (1994).

Milligan, G. et al., "$G_{16}$ as a universal G protein adapter: implications for agonist screening strategies," *Trends Pharm. Sci.* 17:235-237, Elsevier Science Ltd. (Jul. 1996), Ramm, P., "Imaging systems in assay screening, " *Drug Discovery Today* 4:401-410, Elsevier Science Ltd. (Sep. 1999).

* cited by examiner

|   | 1 | 2 | 3 | 4 | 5 | 6 |
|---|---|---|---|---|---|---|
| A | 1. 0.1 M Na IODIDE? | 2. 0.01 M L-CYSTEINE | 3. 0.01 M EDTA | 4. 0.01 M BETA-NICOTINAMIDE ADENOSINE DINUCLEOTIDE | 5. 0.01 M ADENOSINE-5'-TRIPHOSPHATE DISODIUM SALT | 6. 3% D(+)-GLUCOSE MONOHYDRATE |
| B | 13. 3% 1,6-DIAMINOHEXANE | 14. 3% 1,8-DIAMINOOCTANE | 15 0.1 M GLYCINE | 16. 0.01 M Glycyl-glycyl-glycin | 17. 0.01 M HEXAMINECOBALT TRICHLORIDE | 18. 0.01 M TAURINE |
| C | 25. 0.01 M Ba CHLORIDE | 26. 0.01 M Cd CHLORIDE | 27. 0.01 M CA CHLORIDE DIHYDRATE | 28. 0.01 M COBALTOUS CHLORIDE | 29. 0.01 M CUPRIC CHLORIDE DIHYDRATE | 30. 0.01 M Mg CHLORIDE HEXAHYDRATE |
| D | 37. 3% ETHELENE GLYCOL | 38. 3% GLYCEROL | 39. 3% 1,6 HEXANEDIOL | 40. 3% ISOPROPANOL | 41. 3% METHANOL | 42. 3% MPD |

|   | 7 | 8 | 9 | 10 | 11 | 12 |
|---|---|---|---|---|---|---|
| A | 7. 3% D(+)-SUCROSE | 8. 3% ZYLITOL | 9. 0.01 M SPERMIDINE | 10. 0.01 M SPERMINE TETRA-HCl | 11. 3% 6-AMINOCAPROIC ACID | 12. 3% 1,5-DIAMINOPENTAN di-HCl |
| B | 19. 0.01 M BETAINE MONOHYDRATE | 20. 0.5% POLYVINYLPYRROLIDONE | 21. 0.3 M NON-DETERGENT SULFO-BETAINE 195 | 22. 0.2 M NON-DETERGENT SULFO-BETAINE 201 | 23. 3% DIMETHYL SULFOXIDE | 24. 0.01 M PHENOL |
| C | 31. 0.01 M Mn (11) CHLORIDE TETRAHYDRATE | 32. 0.01 M STRONTIUM CHLORIDE I | 33. 0.01 M YTTRIUM CHLORIDE HE; | 34. 0.01 M ZINC CHLORIDE? | 35. 3% DIOXANE | 36 3% ETHANOL |
| D | 43. 5% PEG 400 | 44. 0.01 M TRIMETHYLAMINE HCl | 45. 0.1 M GUANIDINE HCl | 46. 0.01 M UREA | 47. 1.5% 1,2,3-HEPTANETRIOL | 48. 2% BENZAMIDINE HCl |

CONTINUED FROM FIG.5A

|   | 1 | 2 | 3 | 4 | 5 | 6 |
|---|---|---|---|---|---|---|
| E | 49. 0.1 M EGTA | 50. 0.1 M NH4 SULFATE | 51. 0.5 M NH4 SULFATE | 52. 0.1 M NH4 PHOSPHATE | 53. 0.1 M NH4 ACETATE | 54. 0.1 M MG SULFATE |
| F | 61. 0.5 M Li SULFATE | 62. 0.1 M Ni SULFATE | 63. 0.1 M K TARTATE | 64. 0.1 M K CHLORIDE | 65. 0.5 M K CHLORIDE | 66. 0.1 M K PHOSPHATE |
| G | 73. 0.1 M Na PHOSPHATE | 74. 0.5 M Na PHOSPHATE | 75. 0.1 M Na CACODYLATE | 76. 0.01 M di-Na PYROPHOSPHATE | 77. 0.1 M Na TRI-METAPHOSPHATE | 78. 0.1 M TRI-POLYPHOSPHATE |
| H | 85. 0.1 M ARGININE | 86. 0.01 M GLUTATHIONE | 87. 0.1 M 3-NITROBENZENESULF ACID | 88. 0.01 M DHDT | 89. 0.01 M CYCLOHEXYLAMINE | 90. 0.01 M PIPERIDINE |

CONTINUED FROM FIG.5A

| | 7 | 8 | 9 | 10 | 11 | 12 |
|---|---|---|---|---|---|---|
| E | 55. 0.5 M Mg SULFATE | 56. 0.1 M Mg CHLORIDE | 57. 0.1 M Mg ACETATE | 58. 0.1 M Li CHLORIDE | 59. 0.5 M Li CHLORIDE | 60. 0.1 M Li SULFATE |
| F | 67. 0.2 M K SULFATE | 68. 0.05 M K SULFATE | 69. 0.1 M Na FORMATE | 70. 0.1 M Na ACETATE | 71. 0.1 M Na CHLORIDE | 72. 0.1 M Na CITRATE |
| G | 79. 0.1 M OXALATE | 80. 0.1 M MALONATE | 81. 0.1 M SUCCINATE | 82. 0.1 M Zn ACETATE | 83. 0.1 M SORBITOL | 84. 0.1 M Ca CHLORIDE |
| H | 91 0.01 M MORPHOLINE | 92 0.005 M BENZOIC ACID | 93 0.01 M BENZENESULFONIC ACID | 94. 0.01 M SULFOBENZOIC ACID | 95. CONTROL? | 96. CONTROL? |

CONTINUED FROM FIG.5B
CONTINUED FROM FIG.5A

FIG.5D

SEQUENCE LISTING

```
<160> NUMBER OF SEQ ID NOS: 14

<210> SEQ ID NO 1
<211> LENGTH: 64
<212> TYPE: DNA
<213> ORGANISM: Artificial Sequence
<220> FEATURE:
<223> OTHER INFORMATION: AT-rich tract

<400> SEQUENCE: 1
tttttttttt tttttttttt tttttttttt ttaaaaaaaa aaaaaaaaaa aaaaaaaaaa      60
aaaa                                                                   64

<210> SEQ ID NO 2
<211> LENGTH: 64
<212> TYPE: DNA
<213> ORGANISM: Artificial Sequence
<220> FEATURE:
<223> OTHER INFORMATION: AT-rich tract

<400> SEQUENCE: 2
atatatatat atatatatat atatatatat attatatata tatatatata tatatatata      60
tata                                                                   64

<210> SEQ ID NO 3
<211> LENGTH: 64
<212> TYPE: DNA
<213> ORGANISM: Artificial Sequence
<220> FEATURE:
<223> OTHER INFORMATION: AT-rich tract

<400> SEQUENCE: 3
aaataaataa ataaataaat aaataaataa attttatttta tttattttatt tatttattta    60 ttta                                                                   64

<210> SEQ ID NO 4
```

```
<211> LENGTH: 60
<212> TYPE: DNA
<213> ORGANISM: Artificial Sequence
<220> FEATURE:
<223> OTHER INFORMATION: AT-rich tract

<400> SEQUENCE: 4
aaattaaatt aaattaaatt aaattaaatt tttaatttaa tttaatttaa tttaatttaa    60

<210> SEQ ID NO 5
<211> LENGTH: 72
<212> TYPE: DNA
<213> ORGANISM: Artificial Sequence
<220> FEATURE:
<223> OTHER INFORMATION: AT-rich tract

<400> SEQUENCE: 5
aaatttaaat ttaaatttaa atttaaattt aaattttta aatttaaatt taaatttaaa    60
tttaaattta aa                                                       72

<210> SEQ ID NO 6
<211> LENGTH: 64
<212> TYPE: DNA
<213> ORGANISM: Artificial Sequence
<220> FEATURE:
<223> OTHER INFORMATION: AT-rich tract

<400> SEQUENCE: 6
aaaattttaa aattttaaaa ttttaaaatt tttttaaaa ttttaaaatt ttaaaatttt    60
aaaa                                                                64

<210> SEQ ID NO 7
<211> LENGTH: 64
<212> TYPE: DNA
<213> ORGANISM: Artificial Sequence
<220> FEATURE:
<223> OTHER INFORMATION: GC-rich tract

<400> SEQUENCE: 7
cccccccccc cccccccccc cccccccccc ccgggggggg gggggggggg gggggggggg    60
gggg                                                                64

<210> SEQ ID NO 8
<211> LENGTH: 64
<212> TYPE: DNA
<213> ORGANISM: Artificial Sequence
<220> FEATURE:
<223> OTHER INFORMATION: GC-rich tract

<400> SEQUENCE: 8
gcgcgcgcgc gcgcgcgcgc gcgcgcgcgc gccgcgcgcg cgcgcgcgcg cgcgcgcgcg    60
cgcg                                                                64

<210> SEQ ID NO 9
<211> LENGTH: 72
<212> TYPE: DNA
<213> ORGANISM: Artificial Sequence
<220> FEATURE:
<223> OTHER INFORMATION: GC-rich tract

<400> SEQUENCE: 9
gggcccgggc ccgggcccgg gcccgggccc gggccccccg gcccgggcc cgggcccggg    60 cccgggcccg gg                                                       72
```

```
<210> SEQ ID NO 10
<211> LENGTH: 64
<212> TYPE: DNA
<213> ORGANISM: Artificial Sequence
<220> FEATURE:
<223> OTHER INFORMATION: GC-rich tract

<400> SEQUENCE: 10 ggggcccgg ggccccgggg ccccggggcc cccccgggg ccccggggcc ccggggcccc      60
gggg                                                                64

<210> SEQ ID NO 11
<211> LENGTH: 128
<212> TYPE: DNA
<213> ORGANISM: Artificial Sequence
<220> FEATURE:
<223> OTHER INFORMATION: CA- and GT-rich tract

<400> SEQUENCE: 11
cacacacaca cacacacaca cacacacaca cacacacaca cacacacaca cacacacaca     60
cacagtgtgt gtgtgtgtgt gtgtgtgtgt gtgtgtgtgt gtgtgtgtgt gtgtgtgtgt    120
gtgtgtgt                                                            128

<210> SEQ ID NO 12
<211> LENGTH: 128
<212> TYPE: DNA
<213> ORGANISM: Artificial Sequence
<220> FEATURE:
<223> OTHER INFORMATION: CT- and GA-rich tract

<400> SEQUENCE: 12
ctctctctct ctctctctct ctctctctct ctctctctct ctctctctct ctctctctct     60
ctctgagaga gagagagaga gagagagaga gagagagaga gagagagaga gagagagaga    120
gagagaga                                                            128

<210> SEQ ID NO 13
<211> LENGTH: 128
<212> TYPE: DNA
<213> ORGANISM: Artificial Sequence
<220> FEATURE:
<223> OTHER INFORMATION: AG- and TC-rich tract

<400> SEQUENCE: 13
agagagagag agagagagag agagagagag agagagagag agagagagag agagagagag     60
agagtctctc tctctctctc tctctctctc tctctctctc tctctctctc tctctctctc    120
tctctctc                                                            128

<210> SEQ ID NO 14
<211> LENGTH: 60
<212> TYPE: DNA
<213> ORGANISM: Artificial Sequence
<220> FEATURE:
<223> OTHER INFORMATION: T- and A-rich tract with single-stranded and
      duplex DNA

<400> SEQUENCE: 14
tttttttttt tttttttttt tttttttttt tttttttttt aaaaaaaaaa aaaaaaaaaa     60
```

HIGH THROUGHPUT METHOD FOR FUNCTIONALLY CLASSIFYING PROTEINS IDENTIFIED USING A GENOMICS APPROACH

CROSS-REFERENCE TO RELATED APPLICATION

The present invention claims priority benefit of U.S. nonprovisional application Ser. No. 09/190,128, filed Nov. 12, 1998 now abandoned, and U.S. provisional Appl. No. 60/065,129, filed Nov. 12, 1997, both of which are hereby incorporated by reference in their entirety.

BACKGROUND OF THE INVENTION

1. Field of the Invention

The present invention relates generally to a method of classifying a protein based on the ability of one or more ligands to modify the stability, and particularly the thermal stability, of the protein, such that the modification of the stability denotes an interaction between the ligand and the protein.

2. Related Art

The $\sim 3 \times 10^9$ nucleotide base pairs contained within the human genome code for approximately 60,000 to 100,000 essential proteins (Alberts, et al., In: "*Molecular Biology of the Cell*", 3rd Ed., Alberts, B. D. et al., Eds. (1994); Rowen, L. et al., *Science* 278:605 (1997)). Human Genome Project researchers are rapidly identifying all the genes in the 23 pairs of human chromosomes. The products of these genes are-widely recognized as the future pool of therapeutic targets for development of pharmaceuticals in the coming decades. While the sequencing of the human genome will be largely completed within a few years, elucidation of the function of these genes will lag far behind. Therefore, new technologies are required to understand the functional organization of the human genome and make the transition from "structural genomics," or sequence information, to "functional genomics," or gene function, and the association with normal and pathological phenotypes (Hieter & Boguski, *Science* 278:601 (1997)).

The difficulty of this task has been clearly illustrated by the recent discovery that of the 4288 genes in the elementary *E. coli* genome, the function of about 40% of the proteins encoded by these genes are completely unknown (Blattner et al., *Science* 277:1453 (1997)). Indeed, of the 12 simple organisms for which complete genomic information is available, with *S. cerevisiae* being the largest at 12.1 megabases (6034 genes), only 44% to 69% of the genes have been identified using current state-of-the-art computational sequence comparisons (Pennisi, E., *Science* 277:1433 (1997)). Moreover, the spirochete that causes syphilis has 1,014 genes, 45% of which have no known function (Fraser et al., *Science* 281:375–388 (1998)). As a result, there is a functional information gap that presents a challenge to traditional methodologies, and at the same time an opportunity for discovery of new targets for therapeutic intervention.

However, classification of proteins of unknown function based on nucleotide or amino acid homology with proteins of known function is inaccurate and unreliable. Proteins that have structural homology can have dissimilar functions. For example, lysozyme and α-lactalbumin have 40% sequence homology, but divergent functions. Lysozyme is a hydrolase and α-lactalbumin is a calcium binding protein involved in lactose synthesis for secretion into milk of lactating mammals (Qasba and Kumar, *Crit. Rev. Biochem. Mol. Biol.* 32: 255–306(1997)).

Some proteins have similar function, yet have no sequence homology. For example, the serine proteases trypsin and subtilisin exhibit similar function, but exhibit neither sequence homology nor structural homology (Tong et al., *Nature Structural Biology* 9: 819–826 (1998)). Cyclic AMP-dependent protein kinases from the kinase fold family, and D-Ala:D-Ala ligase, from the "ATP Grasp" fold family, have no sequence homology, yet share common structural elements for ATP recognition and are both ATP-dependent enzymes (Denessiouk et al., *Protein Science* 7: 1768–1771 (1998)). Some proteins exhibit no sequence homology, exhibit some structural homology, yet have dissimilar functions. Examples of such proteins are bleomycin resistance protein, biphenyl 1,2-dioxygenase, and human glyoxalase (Bergdoll et a., *Protein Science* 7: 1661–1670 (1998)).

Thus, there is a need for an accurate, reliable technology that facilitates the rapid, high-throughput classification of proteins of unknown function.

SUMMARY OF THE INVENTION

The present invention provides methods for functionally classifying a protein. The methods are related to the ability of molecules in a multiplicity of different molecules to modify the stability of a protein, and therefore bind to the protein. Three of the methods do not involve a determination of whether the molecules that bind to the protein shift the thermal unfolding curve of the protein. Three alternative and distinct methods involve determining whether molecules that bind to a protein shift the thermal unfolding curve of the protein.

A. Methods that Do Not Involve Determining Whether Molecules that Bind Shift the Thermal Unfolding Curve of the Protein The present invention provides a method for functionally classifying a protein, the method comprising screening one or more of a multiplicity of different molecules for their ability to modify the stability of the protein, wherein modification of the stability of the protein indicates that the molecule binds to the protein; generating an activity spectrum for the protein from the screening, wherein the activity spectrum reflects a subset of molecules, from the multiplicity of different molecules, that modify the stability of the protein and therefore are ligands that bind to the protein; comparing the activity spectrum for the protein to one or more functional reference spectrum lists; and classifying the protein according to the set of molecules in the multiplicity of different molecules that modify the stability of the protein.

The present invention also provides a method for functionally classifying a protein, the method comprising screening one or more of a multiplicity of different molecules known to bind to a particular class of proteins for their ability to modify the stability of the protein, wherein modification of the stability of the protein indicates that the molecule binds to the protein; generating an activity spectrum for the protein from the screening, wherein the activity spectrum reflects a subset of molecules, from the multiplicity of different molecules, that modify the stability of the protein and therefore are ligands that bind to the protein; and classifying the protein as a member of the class of proteins if the one or more of the multiplicity of different molecules modify the stability of the protein.

The present invention also provides a method for functionally classifying a protein, the method comprising classifying the protein according to the set of molecules in a multiplicity of different molecules that modify the stability of the protein.

B. Alternative and Distinct Methods that Involve Determining Whether Molecules that Bind Shift the Thermal Unfolding Curve of the Protein The present invention provides a method for functionally classifying a protein that is capable of unfolding due to a thermal change, the method comprising screening one or more of a multiplicity of different molecules for their ability to shift the thermal unfolding curve of the protein, wherein a shift in the thermal unfolding curve of the protein indicates that the molecule binds to the protein; generating an activity spectrum for the protein from the screening, wherein the activity spectrum reflects a subset of molecules, from the multiplicity of different molecules, that shift the thermal unfolding curve of the protein and therefore are ligands that bind to the protein; comparing the activity spectrum for the protein to one or more functional reference spectrum lists; and classifying the protein according to the set of molecules in the multiplicity of different molecules that shift the thermal unfolding curve of the protein.

The present invention also provides a method for functionally classifying a protein that is capable of unfolding due to a thermal change, the method to bind to a particular class of proteins for their ability to shift the thermal unfolding curve of the protein, wherein a shift in the thermal unfolding curve of the protein indicates that the molecule binds to the protein; generating an activity spectrum for the protein from the screening, wherein the activity spectrum reflects a subset of molecules, from the multiplicity of different molecules, that shift the thermal unfolding curve of the protein and therefore are ligands that bind to the protein; and classifying the protein as a member of the class of proteins if the one or more of the multiplicity of different molecules shift the thermal unfolding curve of the protein.

The present invention also provides a method for functionally classifying a protein capable of unfolding due to a thermal change, the method comprising classifying the protein according to the set of molecules in a multiplicity of different molecules that shift the thermal unfolding curve of the protein.

There are several advantages of methods of the present invention for the drug discovery process, especially with regard to functional genomics. For example, the methods of the present invention afford widespread cross-target utility because it is based on thermodynamic properties common to all ligand/receptor complexes. Further, the methods of the present invention facilitate the direct evaluation of protein targets derived from genomic studies because no knowledge of specific target function is necessary.

A further advantage provided by the methods of the present invention is that it can be applied universally to any receptor that is a drug target. It is not necessary to invent a new assay every time a new receptor becomes available for testing. Thus, screening of compound libraries begin immediately upon the preparation of the protein target. When the receptor under study is an enzyme, researchers can determine the rank order of affinity of a series of compounds more quickly and more easily than they can using conventional kinetic methods. In addition, researchers can detect ligand binding to an enzyme, regardless of whether binding occurs at the active site, at an allosteric cofactor binding site, or at a receptor subunit interface. The present invention is equally applicable to non-enzyme receptors.

Yet a further advantage provided by the methods of the present invention is that the methods can be practiced using miniaturized assay volumes (e.g., 1–5 µL), which facilitates the use of high density microplate assay arrays of 16×24 (384 well), 32×48 (1536 well), or further customized arrays. Only about 5 to 40 picomole of protein are required (0.1 µg to 1.0 µg for a 25 kDa protein) per assay well, for a final protein concentration of about 1 to 4 µM. Thus, 1.0 mg of protein can be used to conduct $10^3$ to $10^4$ assays in the miniaturized format.

Yet a further advantage provided by the present invention is that the methods of the present invention facilitate the ultra high throughput screening of compound libraries (e.g., functional probe libraries). Thus the methods of the present invention make it possible to screen 10,000 to 30,000 compounds per day per workstation. At that rate, at least 2.5 to 6 target proteins can be screened per day, per workstation, against a functional probe library of 4000 compounds. At least 500 to 1200 therapeutic targets can be screened per year, per workstation, against a 4000 compound functional probe library. In five years, one could sample about 3 to 7.5% of the proteins encoded by the human genome per workstation.

Yet a further advantage provided by the methods of the present invention is that the wide dynamic range of binding affinities that can be assayed in the single well assay spans twelve orders of magnitude (i.e., from femtomolar ($10^{-15}$ M) to millimolar ($10^{-3}$ M) affinities).

Yet a further advantage provided by the methods of the present invention is that multi-ligand binding interactions can be monitored through the near additivity of the free energy of ligand binding for individual ligands.

Moreover, the methods of the present invention provide information that is more accurate and reliable than information provided by conventional sequence homology methodologies, such as those reported in Tatusov, R. L. et al., *Science* 278: 631–637 (1997); and Heiter, P. and M. Boguski, *Science* 278: 601–602 (1997).

Moreover, different enzyme classes may be identified and differentiated based on binding of different sets of transition state analogs. For example, benzeneboronic acid derivatives (BBA) have been found to reversibly bind to diverse serine proteases such as subtilisins, from bacterial sources, and α-chymotrypsin, from eukaryotic sources (Nakatani, H., et al., *J. Biochem.* (Tokyo) 77:905–8 (1975)). Similarly, boro-arginine transition state analogs, which have an arginine group in the P1 position for this synthetic peptide mimic, were found to be more specific inhibitors for the serine proteases, thrombin, trypsin, and plasmin (Tapparelli et al., *J. Biol. Chem.* 268:4734–41 (1993)) with the observed specificity: $K_d$~10 nM (thrombin), $K_d$~1,000 nm (trypsin), $K_d$~10,000 nM (plasmin). This illustrates an important advantage that the methods of the present invention provide, relative to the sequence comparison approach to classifying proteins: the $\Delta T_m$ shift expected from the binding of aboronic acid transition state analog should be much more characteristic of a serine protease (regardless of bacterial or eukaryotic source) than the information provided by sequence comparisons alone. Serine proteases from bacterial and eukaryotic sources are textbook examples of convergent evolution, and therefore have very little sequence homology, despite the fact that they share catalytic function.

Further features and advantages of the present invention are described in detail below with reference to the accompanying drawings.

BRIEF DESCRIPTION OF THE FIGURES

FIGS. 5A–5D show the compounds present in plate 1 of the functional probe library.

DETAILED DESCRIPTION OF THE PREFERRED EMBODIMENTS

Figure 1A:
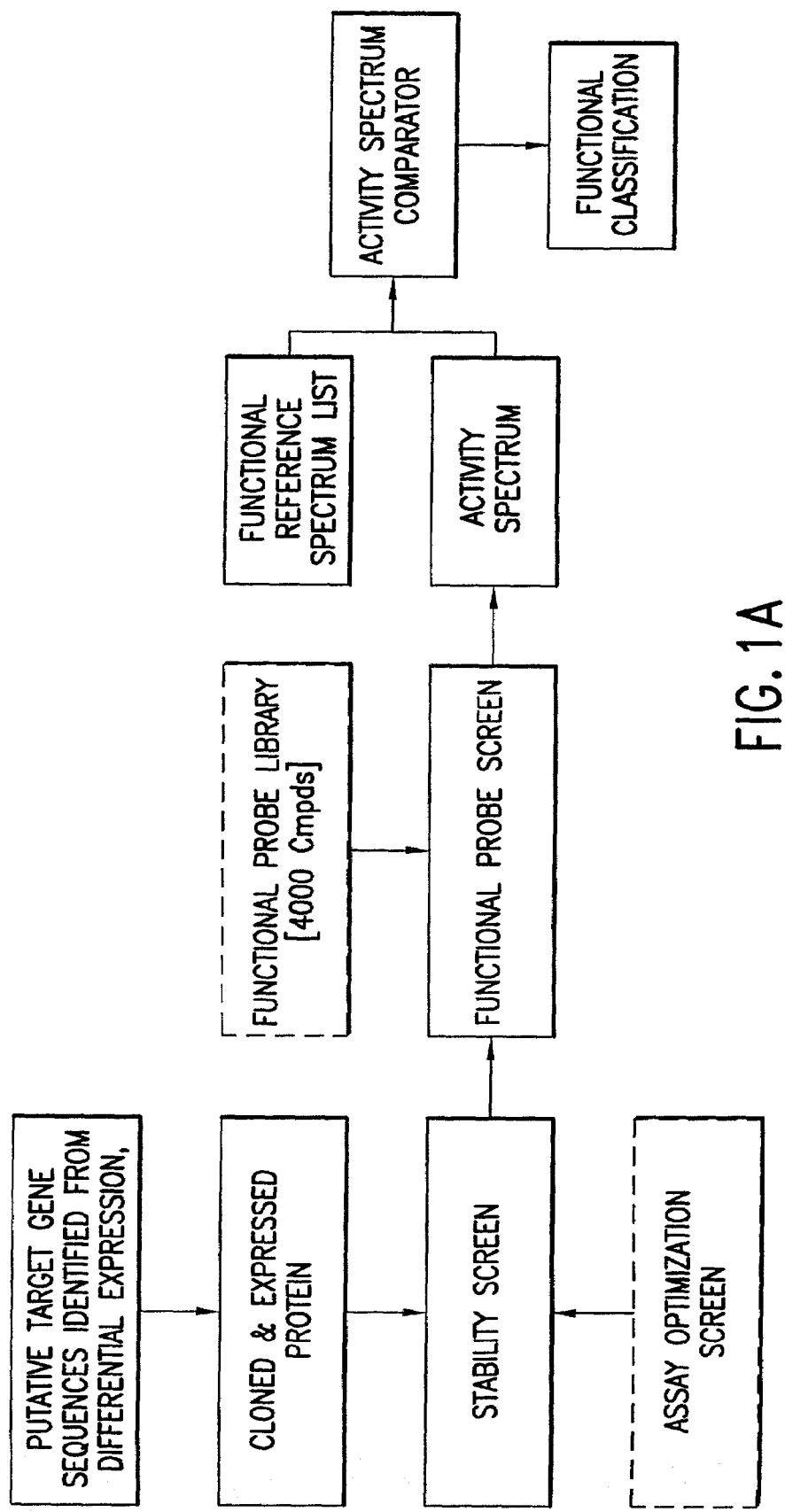
FIG. 1A shows a flow diagram illustrating a method of the present invention.

In the following description, reference will be made to various terms and methodologies known to those of skill in the biochemical and pharmacological arts. Publications and other materials setting forth such known terms and methodologies are incorporated herein by reference in their entireties as though set forth in full.

The present invention provides methods for functionally classifying a protein, which is capable of unfolding, according to the set of molecules in a multiplicity of different molecules that modify the stability of the protein. A protein can be caused to unfold by treatment with a denaturing agent (such as urea, guanidinium hydrochloride, guanidinium thiosuccinate, etc.), a detergent, by treating the protein with pressure, by heating the protein, etc.

The present invention provides methods for functionally classifying a protein that involve determining whether the thermal unfolding curve of the protein is shifted. Only molecules that shift the thermal unfolding curve are deemed to be ligands that bind to the protein. Preferably, the microplate thermal shift assay is used to determine whether the thermal unfolding curve of the protein is shifted. The microplate thermal shift assay involves determining whether molecules that are tested for binding shift the thermal unfolding curve. The microplate thermal shift assay is described in international patent Appl. No. PCT/US97/ 08154 (published Nov. 13, 1997 as publication no. WO 97/42500); U.S. patent application Ser. No. 08/853,464, filed May 9, 1997; and U.S. patent application Ser. No. 08/853,459, filed May 9, 1997.

In a preferred embodiment, the present invention provides a method for classifying a target protein that is capable of unfolding due to a thermal change. In one this embodiment, the target protein is contacted with one molecule of a multiplicity of different molecules in each of a multiplicity of containers. The containers are then heated, in intervals, over a range of temperatures. Preferably, the multiplicity of containers is heated simultaneously. After each heating interval, a physical change associated with the thermal unfolding of the target molecule is measured. In an alternate embodiment of this method, the containers are heated in a continuous fashion. A thermal unfolding curve is plotted as a function of temperature for the target molecule in each of the containers. Preferably, the temperature midpoint, $T_m$, of each thermal unfolding curve is identified and is then compared to the $T_m$ of the thermal unfolding curve obtained for the target molecule in the absence of any of the molecules in the containers. Alternatively, an entire thermal unfolding curve can be compared to other entire thermal unfolding curves using computer analytical tools.

The methods of the present invention that involve determining whether molecules shift the thermal unfolding curve of a protein are distinct from methods that do not involve determining whether molecules shift the thermal unfolding curve of a protein, such as assays of susceptibility to proteolysis, surface binding by protein, antibody binding by protein, molecular chaperone binding of protein, differential binding to immobilized ligand, and protein aggregation. Such assays are well-known to those of ordinary skill in the art. For example, see U.S. Pat. No. 5,585,277; and U.S. Pat. No. 5,679,582. These approaches disclosed in U.S. Pat. Nos. 5,585,277 and 5,679,582 involve comparing the extent of folding and/or unfolding of the protein in the presence and in the absence of a molecule being tested for binding. These approaches do not involve a determination of whether any of the molecules that bind to the protein shift the thermal unfolding curve of the protein.

The term "functionally classifying proteins" refers to classifying a protein according to a biological, biochemical, physical or chemical function, such as the ability to hydrolyze a phosphate moiety (a phosphatase), to add a phosphate moiety (a kinase), etc. Proteins can be classified as having one or more of numerous different functions, and the methods of the present invention are not limited to classifying proteins as phosphatases, kinases, or other types of enzymes.

The terms "multiplicity of molecules," "multiplicity of compounds," or "multiplicity of containers" refer to at least two molecules, compounds, or containers.

The term "subset of molecules" in a multiplicity of different molecules refers to a set of molecules smaller than the multiplicity of different molecules.

The term "multi-variable" refers to more than one experimental variable.

The term "screening" refers to the testing of a multiplicity of molecules or compounds for their ability to bind to a target molecule which is capable of unfolding when heated. The screening process is a repetitive, or iterative, process, in which molecules are tested for binding to a protein in an assay of unfolding, and particularly in a thermal shift assay. For example, if a subset of molecules within a functional probe library that is screened for binding to a protein do not bind, then the screening is repeated with another subset of molecules. If the entire library fails to contain any molecules that bind to the protein, then the screening is repeated using molecules from another functional probe library.

As used herein, a "functional probe screen" is an assessment (e.g., an assay) of the ability of a multiplicity of different molecules in a functional probe library to bind to the target protein and modify the stability of the target protein.

As used herein, a "functional probe library" refers to one or more different molecules that are tested for their ability to bind to a target protein and modify the stability, and particularly the thermal stability, of the protein in response to unfolding (e.g., thermal unfolding). By performing a stability test, and preferably a using the microplate thermal shift assay technology, on the protein in the presence of each member of the functional probe library, compounds may be incubated with the target protein individually and/or in groups to determine which ligands individually or in combination bind tightly and specifically to the target protein.

A functional probe library can be any kind of library of molecules, including a library of proteins, a library of protein subunits, a library of peptides, a library of vitamins & co-factors, an enzyme inhibitor library, a nucleic acid library, a carbohydrate library, a generic drug library, a natural product library, or a combinatorial library. For molecules in the functional probe library that bind to the target protein, the biological effect can be assessed in in vitro and in vivo assays.

If the functional probe library is a combinatorial library, then preferably the it is a combinatorial library created using the DirectedDiversity® system. The DirectedDiversity® system is disclosed in U.S. Pat. No. 5,463,564.

As used herein, the term "activity spectrum" refers to the list of compounds (i.e., ligands) that bind to the target protein and modify the stability (e.g., the thermal stability) of the target protein, and the respective affinities of the ligands for the target protein. The terms "functional probe binding profile" and "activity spectrum" are synonymous. A decrease in $T_m$ suggests that the compound or molecule blocks the binding of another molecule that would stabilize the protein. For example, if a metal chelator decreases the $T_m$, that suggests that the protein binds to a metal (e.g., an interaction between calcium and α-lactalbumin). If a reducing agent decreases the $T_m$, that suggests that the protein contains one or more disulfide bonds.

As used herein, the "functional reference spectrum list" refers to a list of target protein classes (including references to appropriate electronic databases), associated ligands, and corresponding binding constants, that can be used to functionally classify a target protein. Alternatively, the functional reference spectrum list can be a set of one or more activity spectra for one or more known proteins. Thus, an activity spectrum for a given protein can serve as a "fingerprint" for that protein and for the functional class of proteins to which the protein belongs.

A "functional reference list" is a list of proteins that share one or more common features, such as binding to a particular ligand, or exhibiting a common activity.

As used herein, an "activity spectrum comparator" is either a computational or a graphical means by which one can compare the activity spectrum, derived from observing the effects of the functional probe library on the target protein, with the functional reference spectrum list. For example, the activity spectrum comparator can be spreadsheet software that is readily available to those of ordinary skill in the art. For example, MicroSoft Excel (MicroSoft Inc., Redmond, Wash.) can be used.

In may cases, a function of a gene may be tentatively assigned through homology to sequences of known function (a "functional hypothesis" derived from sequence homology). The thermal shift assay can be employed to validate such a functional hypothesis, or to identify the correct function from a list of possible functions implied by sequence homology. For example, there are proteins that hydrolyze ATP and convert the energy of hydrolysis into mechanical energy, known as "molecular motors." These proteins include DNA and RNA helicases, kinesins, chaperonins for refolding proteins, and the protein complexes in the base of bacterial flagella. These proteins all share sequence homology in the ATP-hydrolyzing domain, whereas their other functions are different. In one application of the methods of the present invention, the known sequence homology for a portion of a protein target (e.g., an ATPase domain) may be used to design thermal shift assays using special functional probe libraries directed at different possible functions of the target protein (e.g., libraries containing molecules for probing the special activities of chaperonins, helicases, kinesins, and other molecular motors). Alternatively, a target protein may be identified via sequence homology as a tyrosine kinase, and the present invention could then be used to screen this target against a peptide library containing many possible substrate phosphorylation sites. These examples illustrate that the present invention is highly complementary to the process of assigning function using sequence homology, because the present invention can be used to confirm, reject, or elaborate the hypothetical functions indicated by sequence homology.

Accordingly, the present invention also provides a method for functionally classifying a protein, the method comprising (a) screening one or more of a multiplicity of different molecules known to bind to a particular class of proteins for their ability to modify the stability of said protein, wherein modification of the stability of the protein indicates that the molecule binds to the protein, (b) generating an activity spectrum for the protein from the screening step, wherein the activity spectrum reflects a subset of molecules, from the multiplicity of different molecules, that modify the stability of said protein, and (c) classifying the protein as a member of said class of proteins if the one or more of the multiplicity of different molecules modify the stability of the protein.

It should be noted that the above process for elaborating or specifying protein function using a thermal shift assay can also be applied to functional hypotheses generated using other methods of assigning protein function (e.g., three-dimensional structures of proteins and nucleic acids, patterns of cellular expression of mRNA or a protein encoded by a target gene, and phenotypic effects of altering a target gene to change its function at the organismal level).

Further, using the methods of the present invention, one can assess the binding of more than one ligand to more than one site on a protein, and classify the protein according to the subset of molecules that bind to the protein. For example, a protein of unknown function that is found to bind to DNA and to adenosine triphosphate (ATP) can be classified as a protein that affects DNA structure. Thus, using information concerning the binding of multiple ligands, the large number of possible protein classifications can be narrowed to only a few likely classifications.

Moreover, using the methods of the present invention, one can also screen a protein of known function for an additional, previously unknown, function. Preferably, the microplate thermal shift assay is used to screen the functional probe library of molecules against the proteins.

The term "function" refers to the biological function of a protein, peptide or polypeptide. For example, a kinase is a protein for which the function is catalyzing the covalent addition of a phosphate group to another protein.

The term "molecule" refers to the compound which is tested for binding affinity for the target molecule. This term encompasses chemical compounds of any structure, including, but not limited to nucleic acids, such as DNA and RNA, and peptides. More specifically, the term "molecule" encompasses compounds in a compound or a combinatorial library. The terms "molecule" and "ligand" are synonymous.

The term "contacting a target protein" refers broadly to placing the target protein in solution with the molecule to be screened for binding. Less broadly, contacting refers to the turning, swirling, shaking or vibrating of a solution of the target protein and the molecule to be screened for binding. More specifically, contacting refers to the mixing of the target protein with the molecule to be tested for binding. Mixing can be accomplished, for example, by repeated uptake and discharge through a pipette tip. Preferably, contacting refers to the equilibration of binding between the target protein and the molecule to be tested for binding. Contacting can occur in the container or before the target protein and the molecule to be screened are placed in the container.

The term "container" refers to any vessel or chamber in which the receptor and molecule to be tested for binding can be placed. The term "container" encompasses reaction tubes (e.g., test tubes, microtubes, vials, etc.). Preferably, the term "container" refers to a well in a multiwell microplate or microtiter plate.

The term "sample" refers to the contents of a container.

The terms "spectral emission," "thermal change" and "physical change" encompass the release of energy in the form of light or heat, the absorption of energy in the form or light or heat, changes in turbidity and changes in the polar properties of light. Specifically, the terms refer to fluorescent emission, fluorescent energy transfer, absorption of ultraviolet or visible light, changes in the polarization properties of light, changes in the polarization properties of fluorescent emission, changes in the rate of change of fluorescence over time (i.e., fluorescence lifetime), changes in fluorescence anisotropy, changes in fluorescence resonance energy transfer, changes in turbidity, and changes in enzyme activity. Preferably, the terms refer to fluorescence, and more preferably to fluorescence emission. Fluorescence emission can be intrinsic to a protein or can be due to a fluorescence reporter molecule. The use of fluorescence techniques to monitor protein unfolding is well known to those of ordinary skill in the art. For example, see Eftink, M. R., *Biophysical J.* 66:482–501 (1994).

The term "unfolding" refers to the loss of structure, such as crystalline ordering of amino acid side-chains, secondary, tertiary, or quaternary protein structure.

The terms "folding," "refolding," and "renaturing" refer to the acquisition of the correct amino acid side-chain ordering, secondary, tertiary, or quaternary structure, of a protein, which affords the full chemical and biological function of the biomolecule.

The term "denatured protein" refers to a protein which has been treated to remove native amino acid side-chain ordering, secondary, tertiary, or quaternary structure. The term "native protein" refers to a protein which possesses the degree of amino acid side-chain ordering, secondary, tertiary or quaternary structure that provides the protein with full chemical and biological function. A native protein is one which has not been heated and has not been treated with unfolding agents or chemicals such as urea.

As used herein, the terms "protein" and "polypeptide" are synonymous.

An "unfolding curve" is a plot of the physical change associated with the unfolding of a protein as a function temperature, denaturant concentration, pressure, etc. A "denaturation curve" is a plot of the physical change associated with the denaturation of a protein or a nucleic acid as a function of temperature, denaturant concentration, pressure, etc A "thermal unfolding curve" is a plot of the physical change associated with the unfolding of a protein or a nucleic acid as a function of temperature. A "thermal denaturation curve" is a plot of the physical change associated with the denaturation of a protein or a nucleic acid as a function of temperature. See, for example, Davidson et al., *Nature Structure Biology* 2:859 (1995); and Clegg, R. M. et al., *Proc. Natl. Acad. Sci. U.S.A.* 90:2994–2998 (1993).

The term "shift in the thermal unfolding curve" refers to a shift in the thermal unfolding curve for a protein that is bound to a ligand, relative to the thermal unfolding curve of the protein in the absence of the ligand.

The term "modification of stability" refers to the change in the amount of pressure, the amount of heat, the concentration of detergent, or the concentration of denaturant that is required to cause a given degree of physical change in a target protein that is bound by one or more ligands, relative to the amount of pressure, the amount of heat, the concentration of detergent, or the concentration of denaturant that is required to cause the same degree of physical change in the target protein in the absence of any ligand. Modification of stability can be exhibited as an increase or a decrease in stability. Modification of the stability of a protein by a ligand indicates that the ligand binds to the protein. Modification of the stability of a protein by more than one ligand indicates that the ligands bind to the protein.

The term "modification of thermal stability" refers to the change in the amount of thermal energy that is required to cause a given degree of physical change in a target protein that is bound by one or more ligands, relative to the amount of thermal energy that is required to cause the same degree of physical change in the target protein in the absence of any ligand. Modification of thermal stability can be exhibited as an increase or a decrease in thermal stability. Modification of the thermal stability of a protein by a ligand indicates that the ligand binds to the protein. Modification of the thermal stability of a protein by more than one ligand indicates that the ligands bind to the protein.

The "midpoint temperature, $T_m$" is the temperature midpoint of a thermal unfolding curve. The $T_m$ can be readily determined using methods well known to those skilled in the art. See, for example, Weber, P. C. et al., *J. Am. Chem. Soc.* 116:2717–2724 (1994); and Clegg, R. M. et al., *Proc. Natl. Acad. Sci. U.S.A.* 90:2994–2998 (1993).

As discussed above, it is preferable to determine the effect of one or more molecules on the thermal stability of a target protein according to a change in the $T_m$ of the thermal unfolding curve for the protein. Alternatively the effect of one or more molecules on the thermal stability of a target protein can be determined according to the change in entire thermal unfolding curve for the target protein.

The term "fluorescence probe molecule" refers to an extrinsic fluorophore, which is a fluorescent molecule or a compound which is capable of associating with an unfolded or denatured receptor and, after excitement by light of a defined wavelength, emits fluorescent energy. The term fluorescence probe molecule encompasses all fluorophores. More specifically, for proteins, the term encompasses fluorophores such as thioinosine, and N-ethenoadenosine, formycin, dansyl, dansyl derivatives, fluorescein derivatives, 6-propionyl-2-(dimethylamino)-napthalene (PRODAN), 2-anilinonapthalene, and N-arylamino-naphthalene sulfonate derivatives such as 1-anilinonaphthalene-8-sulfonate (1,8-ANS), 2-anilinonaphthalene-6-sulfonate (2,6-ANS), 2-amino-naphthalene-6-sulfonate, N,N-dimethyl-2-aminonaphthalene-6-sulfonate, N-phenyl-2- aminonaphthal-ene, N-cyclohexyl-2-aminonaphthalene-6-sulfonate, N-phenyl-2-amino-naphthalene-6-sulfonate, N-phenyl-N-methyl-2-aminonaphthalene-6-sulfonate, N-(o-toluyl)-2-amino-naphthalene-6-sulfonate, N-(m-toluyl)-2-amino-naphthalene-6-sulfonate, N-(p-toluyl)-2-aminonaphthalene-6-sulfonate, 2-(p-toluidinyl)-naphthalene-6-sulfonic acid (2,6-TNS), 4-(dicyanovinyl) julolidine (DCVJ), 6-dodecanoyl-2-dimethylaminonaphthalene (LAURDAN), 6-hexadecanoyl-2-(((2-(trimethylammonium)ethyl)methyl)-amino)naphthalene chloride (PATMAN), nile red, N-phenyl-1-naphthylamine, 1,1-dicyano-2-[6-(dimethylamino) naphthalen-2-yl]propene (DDNP), 4,4'-dianilino-1,1-binaphthyl-5,5-disulfonic acid (bis-ANS), and 5-(4"-dimethylaminophenyl)-2-(4'-phenyl)oxazole derivative dyes, sold under the trademark DAPOXYL™ (Molecular-Probes, Inc., Eugene, Oreg.), including the 5-(4"-dimethylaminophenyl)-2-(4'-phenyl)oxazole dyes provided in Diwu, Z. et al., *Photochemistry and Photobiology* 66(4): 424–431 (1997), and in *BioProbes* 25: pp. 8–9, Molecular Probes, Inc., Eugene, Oreg. (1997).

Examples of 5-(4"-dimethylaminophenyl)-2-(4'-phenyl) oxazole derivative dyes, and the corresponding Molecular Probes catalogue number, include 5-(4"-dimethylaminophenyl)-2-(4'-phenyl)oxazole butylsulfonamide (D-12801), 5-(4"-dimethylaminophenyl)-2-(4'-phenyl)oxazole-(2-aminoethyl)sulfonamide (D-10460), 5-(4"-dimethylaminophenyl)-2-(4'-phenyl)oxazolebutylsulfonamide (D-12801), 5-(4"-dimethylaminophenyl)-2-(4'-phenyl)oxazole-3-sulfonamidophyenylboronic acid (D-10402), 5-(4"-dimethylaminophenyl)-2-(4'-phenyl)oxazole sulfonic acid, sodium salt (D-12800), 5-(4"-dimethylaminophenyl)-2-(4'-phenyl) oxazole sulfonyl hydrazine (D-10430), 5-(4"-dimethylaminophenyl)-2-(4'-phenyl)oxazole-(2-bromoacetamidoethyl) sulfonamide (D-10300), 5-(4"-dimethylaminophenyl)-2-(4'-phenyl)oxazole-2-(3-(2-pyridyldithio)propionamidoethyl) sulfonamide (D-10301), 5-(4"-dimethylaminophenyl)-2-(4'-phenyl)oxazole sulfonyl chloride (D-10160), 5-(4"-dimethylaminophenyl)-2-(4'-phenyl)oxazole-3-sulfonamidopropionic acid, succinimidyl ester(D-10162), 5-(4"-dimethylaminophenyl)-2-(4'-phenyl)oxazole carboxylic acid, succinimidyl ester (D-10161).

Preferably the term "fluorescence probe molecule" refers to 1,8-ANS or 2,6-TNS, and 5-(4"-dimethylaminophenyl)-2-(4'-phenyl)oxazole derivative dyes, sold under the trademark DAPOXYL™, such as those provided in Diwu, Z. et al., *Photochemistry and Photobiology* 66(4): 424–431 (1997). Still more preferably, the term refers to 5-(4"-dimethylaminophenyl)-2-(4'-phenyl)oxazole derivative dyes, sold under the trademark DAPOXYL™, such as those provided in Diwu, Z. et al., *Photochemistry and Photobiology* 66(4): 424–431 (1997). Most preferably, the term refers to 5-(4"-dimethylaminophenyl)-2-(4'-phenyl)oxazole sulfonic acid, sodium salt (D-12800).

The term "carrier" encompasses a platform or other object, of any shape, which itself is capable of supporting at least two containers. The carrier can be made of any material, including, but not limited to glass, plastic, or metal. Preferably, the carrier is a multiwell microplate. The terms microplate and microtiter plate are synonymous. The carrier can be removed from the heating element. In the present invention, a plurality of carriers are used. Each carrier holds a plurality of containers.

The terms "spectral measurement" and "spectrophotometric measurement" are synonymous and refer to measurements of changes in the absorption of light. Turbidity measurements, measurements of visible light absorption, and measurement of ultraviolet light absorption are examples of spectral measurements. Measurement of the intrinsic fluorescence of a target protein, and the fluorescence of an extrinsic fluorophore that is complexed with or bound to a target protein are also examples of spectral measurement and spectrophotometric measurement.

The term "polarimetric measurement" relates to measurements of changes in the polarization properties of light and fluorescent emission. Circular dichroism and optical rotation are examples of polarization properties of light which can be measured polarimetrically. Measurements of circular dichroism and optical rotation are taken using a spectropolarimeter. "Nonpolarimetric" measurements are those that are not obtained using a spectropolarimeter.

Knowledge of the cellular and/or biological function of proteins can be a valuable asset in drug discovery, where it can be useful in developing a detailed understanding of the therapeutic hypothesis for drug function, in designing specific strategies for drug design, and in revealing potential drug side effects.

There are tens of thousands of different enzymes and receptors that constitute potential drug targets, and more are constantly being discovered through genome sequencing studies. These proteins and cellular receptors have specific functions in the biological system, which are practically defined by the molecular ligands with which they form specific interactions. Typical interactions that have functional significance include enzyme interactions with molecular ligands like substrates or substrate analogs, cofactors, adaptor domains, nucleic acids, etc., and receptor interactions with specific ligands, other receptors, cell surface structural components, nucleic acids, polysaccharides, etc.

While it will be broadly possible to isolate, or to clone and express proteins that are putative drug targets, in many cases there will be no functional knowledge base about the protein that can assist in succeeding stages of the drug discovery process. However, a substantial fraction of known protein molecules fall into mechanistic classes which share important characteristics, including their ability to bind specific types of molecular ligands, including enzyme cofactors, enzyme substrates or substrate analogs, etc. Consequently, it is possible to classify many proteins of otherwise unknown function by their ability to specifically bind various kinds of ligands, either alone or in combination.

When a protein binds to a biological ligand in a functionally significant way, there is an effect on the physical state of the protein that is reflected in its stability relative to its unliganded state. Consequently, one can classify functionally a protein of previously unknown function by incubating it with a probe panel of biological ligands and cofactors (a functional probe library), and measuring which ligands have effects on the stability of the protein. Alternatively, one can determine a previously unknown function of a protein of previously known function by incubating it with a probe panel of biological ligands and cofactors (a functional probe library), and measuring which ligands have effects on the stability of the protein.

As has been established from thermodynamic studies of protein-ligand interactions, when two molecules associate to form a favorable and specific interaction complex, the binding interactions are associated with a reduction in the total free energy of the complex and a net stabilization of the protein-ligand complex relative to the unliganded protein. In practical terms, this means that when an enzyme or receptor interacts with its specific cofactors, or analogs of cofactors, the enzyme or receptor will be stabilized by the interactions. However, it is possible that special situations may exist in which ligand binding may destabilize the target protein. For example, some proteins contain more than one domains or allosteric sites to which one or more ligands can bind.

Overview of the Methods of the Present Invention

Figure 1B:
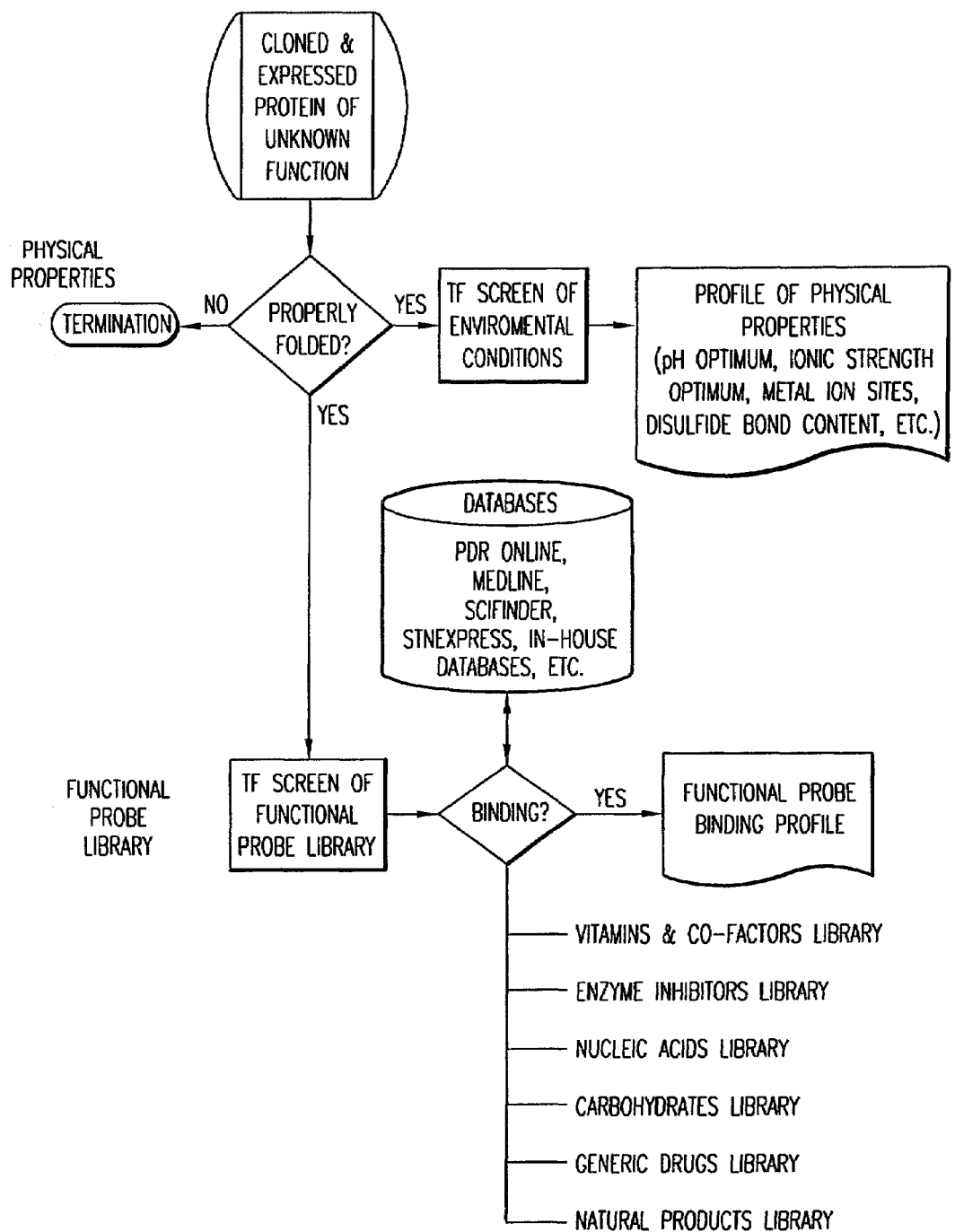
FIG. 1B shows another flow diagram illustrating a method of the present invention.

The methods of the present invention, as well as other information, are depicted in FIGS. 1A and 1B.

A. Identification of a Putative Target Gene

Target proteins are proteins for which binding to a drug may have therapeutic potential and whose functional characterization may be useful in the drug discovery process. Many genes that are potential targets for therapeutic intervention are identified through a phenomenological correlation that relates a genetic defect to a disease state (e.g., when an inherited disease is correlated with a genetic defect in a specific enzyme or receptor) or through differences in protein expression patterns in diseased vs. normal tissues.

In many cases it is possible to determine some "function" of a gene product through sequence homology with a homologous protein about which functional or structural data known. However, in a substantial fraction of cases, sequence homology may not be sufficient to establish functional relationships, and an alternative means is needed to establish function in a way that can directly facilitate the drug discovery process.

B. Clone and Express the Protein

To practice the methods of the present invention, it is necessary to obtain the target protein in sufficient quantities for a biological assay. Proteins that are potential new therapeutic targets and/or require functional characterization may be isolated directly from a natural source using a variety of established biochemical isolation procedures.

The availability of complete gene sequences from genome sequence data facilitates the cloning and expression of protein targets identified via genomic methods. For example, the known target DNA sequence may be used to design oligonucleotide probes to select full-length cDNA clones containing the entire cDNA coding for the gene of interest from a representative library of many such cDNA clones. In another example, the known target DNA sequence may be used to design PCR primers fro selective amplification and cloning of the gene of interest from total genomic DNA. These and other methods for high-throughput cloning and expression are well-known to those of ordinary skill in the art. Thus, full-length gene sequence data automatically provides the direct means for high-throughput, parallel production of protein targets, an necessary first step in any molecule-based, high-throughput functional screening strategy.

C. Thermal Stability Screen

In order to perform a microplate thermal shift assay of a target protein, is necessary to determine assay conditions that are optimal for carrying out the assay. Proteins are linear polymers of amino acids that spontaneously fold into stable, highly organized 3-dimensional structures. The biological activity and functions of a target protein, including virtually all of the specific binding and catalytic properties that characterize the protein, depends on its three-dimensional structure.

Virtually all folded, active protein domains behave thermally as organic crystals that melt with a cooperative, well defined, pseudo first order phase transition: i.e., melt into a partially disordered, organic liquid-like state, with a well defined melting temperature ($T_m$) that reflects the free energy of stabilization of the protein three-dimensional structure in the experimental solvent conditions. The microplate thermal shift technology uses environment-sensitive fluorescent dyes to sensitively detect the thermal unfolding process and to directly monitor effects on protein stability that arise from perturbations of the solvent environment or through ligand binding to the protein.

The stability of the three-dimensional folded state of a protein can potentially be perturbed in several ways. One way is to alter the aqueous solvent environment in which the protein molecules initially fold from a disorganized polymer into the 3-dimensionally organized state. By changing the bulk solvent properties around the protein, the stability of the folded state can be altered relative to the stability of the unfolded state. This can provide a useful strategy for finding optimal conditions for measuring ligand binding and is the principle behind the stability screen.

D. Microplate Thermal Shift Assay Optimization Screen

The assay optimization screen is a set of solvent conditions and fluorescent dyes that are used with the target protein to determine optimal conditions for performing the microplate thermal shift assay. The protein is subjected to a variety of solution conditions and or fluorescent dyes in order to evaluate the behavior of the protein and/or the assay readout.

Examples of variations in conditions could include the addition of organic solvents, variations in pH, salts, etc. that have the potential to alter the relative stability of the folded and unfolded states of the protein. Examples in variations in dyes could include those whose differences in charge, polarity, excitation wavelength, emission wavelength, background signal intensity, or other properties that offer advantages in precision of measurement, miniaturization or optimization of signal to noise under specific assay conditions. The optimization of conditions that facilitate the stability screen is an empirical process and can readily be practiced by one of ordinary skill in the art.

E. Functional Probe Library

A substantial fraction of protein molecules that can serve as potential drug targets fall into mechanistic classes which share important characteristics. For example, many enzymes use ATP as an energetic cofactor, others use pyridine nucleotides as cofactors, some use both as cofactors, etc.

By examining the scientific literature or through experimental means, it is possible to compile a set of enzyme substrates, substrate analogs, cofactors, adaptor protein domains, nucleic acid analogs, polysaccharides, fatty acids, nucleic acids, effector peptides, or other molecules which have been determined to specifically bind to a defined class of protein molecules, or where functional significance has been attached to tight binding to a functionally known class of molecules.

As used herein, a "functional probe library" refers to one or more different molecules that are tested for their ability to bind to a target protein and modify the thermal stability of the protein in response to thermal unfolding. By performing a thermal stability test (preferably by using the microplate thermal shift assay technology) on the protein in the presence of each member the functional probe library, compounds may be incubated with the target protein individually and/or in groups to determine which ligands individually or in combination bind tightly and specifically to the target protein.

Examples of molecules that can comprise a functional probe library include, but are not limited to the following.

1. Vitamins and Coenzymes

NADH/NAD, NADPH/NADP, ATP/ADP, ATP-γ-S, acetyl-CoA, biotin, S-adenosyl-methionine, thiamine pyrophosphate (TPP), sulfated oligosaccharides, heparin-like oligosaccharides, GTP, GTP-γ-S, gamma-S, pyridoxal-5-phosphate, flavin mononucleotide (FMN), flavin adenine dinucleotide (FAD), folic acid, tetrahydrofolic acid, methotrexate, vitamin $K_1$, vitamin E succinate salt, vitamin $D_3$, vitamin $D_{3-25}$-hydroxy, vitamin $D_3$-1-α-25-dihydroxy, vitamin $B_{12}$, vitamin C, vitamin $B_6$, coenzyme A, coenzyme A-n-butyryl, transretinoic acid, and heme.

2. Amino Acid Residue Functional Groups and their Mimics

Building Blocks:
Guanidino groups
Imidazole groups
Phenyl groups
Phenolic groups
Indole groups
Aliphatic chains
Single Amino acids and blocked derivatives
Higher Order Structures:
Peptide hormones
   Vasopressin
   Insulin
   TRH
   Corticotropin
   Glucagon
      $SH_2$ domains, $SH_3$ domains, plextrin domains, etc.
Bioactive Peptides
Lectins

3. Metal Chelators

Calcium Chelators (Calbiochem, San Diego, Calif.)
Iron Chelators

4. Metal Ions

Transition Metals
Calcium, Magnesium

5. Carbohydrates

Building Blocks
Glucose
Galactose
Xylose
Higher Order Biomolecules:
Cellulose
Starch
Fructose
Mannose
Sucrose
Lactose
Bioactive Carbohydrates (Available from Sigma Chemical Co., St. Louis, Mo.)

6. Nucleic Acids

Building Blocks:
Uracil
Thymidine
Cytosine
Adenine
Guanine
Higher Order Structures:
Oligonucleotides
Deoxyribonucleic acid (DNA)
Ribonucleic acid (RNA)

The methods of the present invention can also be used to screen proteins against libraries of synthetic and naturally-occurring nucleic acids (for example, oligonucleotides) to probe for different classes of nucleic acid-binding proteins. For example, there are many DNA-binding proteins that can be identified by their ability to bind to particular classes of DNA sequences. Large libraries containing many different nucleic acid sequences (for example, the 4096 different possible synthetic hexamers, can be purchased or synthesized. At high concentrations, all or part of the cognate binding site of site-specific nucleic acid binding proteins can be detected. In the event that a protein appears to bind several different sequences, binding sites can be reconstructed by synthesizing various combinations of nucleic acid sequences, and then the microplate thermal shift assay, or another assay, can be used to measure binding affinities.

There are many DNA-binding proteins that can be identified by their ability to bind to particular classes of DNA sequences with lower specificity. For example, it is well-known that some transcription factors bind a variety of A/T-rich sequences in preference to G/C-rich sequences. Telomerases are known to recognize G/C-rich sequences. Helicases are known to bind short fragments of single-stranded DNA with low specificity. A smaller, more generic library could contain the following components for detecting these and other DNA-binding proteins:

AT-rich tracts:
      $d(T)_{32}/d(A)_{32}$ (SEQ ID NO: 1)
      $d(ATAT)_8/d(TATA)_8$ (SEQ ID NO: 2)
      $d(AAAT)_8/d(TTTA)_8$ (SEQ ID NO: 3)
      $d(AAATT)_6/d(TTTAA)_6$ (SEQ ID NO: 4)
      $d(AAATTT)_6/d(TTTAAA)_6$ (SEQ ID NO: 5)
      $d(AAAATTTT)_4/d(TTTTAAAA)_4$ (SEQ ID NO: 6)
   GC-rich tracts:
      $d(C)_{32}/d(G)_{32}$ (SEQ ID NO: 7)
      $d(GCGC)_8/d(CGCG)_8$ (SEQ ID NO: 8)
      $d(GGGCCC)_6/d(CCCGGG)_6$ (SEQ ID NO: 9)
      $d(GGGGCCCC)_4/d(CCCCGGGG)_4$ (SEQ ID NO: 10)
   other
      $d(CA)_{32}/d(GT)_{32}$ (SEQ ID NO: 11)
      $d(CT)_{32}/d(GA)_{32}$ (SEQ ID NO: 12)
      $d(AG)_{32}/d(TC)_{32}$ (SEQ ID NO: 13)
   Single-stranded components of the above duplex sequences.
   $d(T)_{40}d(A)_{20}$ (SEQ ID NO: 14) (an example of a fragment containing both single-stranded and duplex DNA)
   Sheared human chromosomal DNA
   "whole genome amplification" applied to different human chromosomes
   Sheared salmon-sperm DNA
   Sheared microbial DNA
   Supercoiled plasmid DNA
   PCR-amplification products from specific chromosomal regions (e.g. telomeres and centromeres)

Other known recognition sites for transcription, RNA processing, transposition

7. Lipids

Building Blocks:
Choline
Phosphoric acid
Glycerol
Palmitic acid
Oleic acid
Cholesterol
Higher Order Structures:
Phosphatidyl choline 8. Enzyme Inhibitors Protease Inhibitors (Sigma Chemical Co., St. Louis, Mo.)
PMSF
Leupeptin
Pepstatin A
Bestatin
Peptide aldehyde Cystatin (Cysteine protease inhibitors)
Protein Tyrosine Kinase inhibitors (Calbiochem, San Diego, Calif.)
Protein Phosphatase inhibitors (Calbiochem, San Diego, Calif.)
Protein Kinase inhibitors (Calbiochem, San Diego, Calif.)
Protein Kinase Activators (Calbiochem, San Diego, Calif.)
Phosphodiesterase inhibitors (Calbiochem, San Diego, Calif.)
Phospholipase Inhibitors
Transition State Analogs Similarly, zinc metalloproteases, such as angiotensin converting enzyme, and carboxypeptidase, would be identifiable (a) by destabilization by EDTA or orthophenanthroline ($Zn^{2+}$ chelation) and (b) by stabilization in the presence of hydroxamates and phosphoramidates that mimic the transition state for $Zn^{2+}$ catalyzed peptide bond hydrolysis.

The functional probe library can also include steroid compounds amine hormones, and alkaloid compounds.

The functional probe library can be a library of generic drugs. Alternatively, the functional probe library can be a natural product library. For example, see the *Encyclopedia of Common Natural Ingredients Used in Foods, Drugs and Cosmetics*, 2nd Edition, Leung and Foster, Eds., Wiley Interscience (1996).

F. Functional Probe Screen

In addition to optimizing conditions that modify protein stability, another way to affect the stability of a folded protein is to specifically bind molecules to either the unfolded or folded state of the protein. Since virtually all biologically active proteins are folded with organized three-dimensional structures, most interest attaches to ligand molecules that bind to and stabilize the folded state of a protein.

As discussed above, a functional probe screen is an assay of the ability of a multiplicity of different molecules in the functional probe library to bind to the target protein and modify the stability of the target protein in response to thermal unfolding. Using the technology, one can directly measure the binding affinity of a small or large molecule ligand to a target protein through its effect on the unfolding midpoint temperature $T_m$ (or thermal unfolding profile) of the protein. For molecules that bind to the folded state of the protein, which include most ligands of biological interest, there is a quantitative relationship between the affinity of ligand binding and the extent to which the $T_m$ of the protein in the liganded state is shifted relative to the $T_m$ of the protein in unliganded state.

Most proteins have functions that are reflected by their ability to bind either large or small molecule ligands with high specificity and high affinity. Many proteins belong to functional classes (e.g. kinases, phosphatases, pyridine nucleotide dependent oxidoreductases, etc.) that bind specific cofactors or catalyze specific reactions using a limited set of catalytic mechanisms. Consequently, molecules in a given functional class like kinases, which use ATP as a cofactor, will generally bind an non-hydrolyzable ATP cofactor analog like AMPPNP, a property that will be detectable using the methods of the present invention.

Moreover, many proteins will bind a combination of ligands or make multiple sets of interactions with biological adaptor domains. To the extent that these interactions are independent, they will generally produce additive perturbations on the stability of the unliganded form of the protein.

When the a protein has been tentatively assigned to a particular protein class, one can rescreen the protein using a library of compounds or molecules known to bind to that class of proteins.

G. Activity Spectrum

After performing a thermal stability test (preferably by using the microplate thermal shift assay technology) on the protein in the presence of each member the functional probe library, one can determine which ligands bind tightly and specifically to the target protein and modify the thermal stability of the target protein. The list of compounds (i.e., ligands) that bind to the target protein and modify the thermal stability of the target protein, and the respective affinities of the ligands for the target protein comprise the activity spectrum of the target protein.

H. Functional Reference Spectrum List

As discussed above, a "functional reference spectrum list" is a list of target protein classes (including references to appropriate electronic databases), associated ligands, and corresponding binding constants, that can be used to functionally classify a target protein. Alternatively, the functional reference spectrum list can be a set of one or more activity spectra for one or more known proteins.

As discussed above, a "functional reference list" is a list of proteins that share one or more common features, such as binding to a particular ligand, or exhibiting a common activity. An example of a functional reference list is given in Table 1. The features shared by the proteins listed in Table 1 is that they bind NAD and exhibit dehydrogenase activity. The list of proteins in Table 1 illustrates how a functionally related class of proteins can be discriminated according to their ability to bind different sets of ligands. For example, a protein that binds nicotinamide adenine dinucleotide (NAD), NADPH, or NADH, and malate, as shown by the ability of these compounds to modify the thermal stability of the protein, could be classified as a malate dehydrogenase. As another example, a protein for which thermal stability is modified by ethanol and NAD could be classified as an alcohol dehydrogenase.

TABLE 1

Functional Reference List

Class 3 Aldehyde Dehydrogenase
Human δ Alcohol Dehydrogenase
α-hydroxysteroid Dehydrogenase

TABLE 1-continued

Functional Reference List

Malate Dehydrogenase
Horse Liver Alcohol Dehydrogenase
Alcohol Dehydrogenase
Glyceraldehyde-3-Phosphate Dehydrogenase
Human β-Alcohol Dehydrogenase
Dihydropteridine Reductase
D-2-Hydroxyisocaproate Dehydrogenase
Brassica Napus Enoyl Acp Reductase
7-α-hydroxysteroid Dehydrogenase
Holo-D-Glyceraldehyde-3-Phosphate Dehydrogenase
Glutathione Reductase
D-Glyceraldehyde-3-Phosphate Dehydrogenase
Glutathione Reductase
3-Isopropylmalate Dehydrogenase
Human β-3 Alcohol Dehydrogenase
Isocitrate Dehydrogenase
Horse Liver Alcohol Dehydrogenase
M4 Lactate Dehydrogenase
Dihydrolipoamide Dehydrogenase
Udp-Gal 4-Epimerase
D-3-Phosphoglycerate Dehydrogenase
Human Liver χχ Alcohol Dehydrogenase
Alpha, 20 β-hydroxysteroid Dehydrogenase
L-Lactate Dehydrogenase
NADH Peroxidase I. Activity Spectrum Comparator As used herein, an "activity spectrum comparator" is either a computational or a graphical means by which one can compare the activity spectrum, derived from observing the effects of the functional probe library on the target protein, with the functional reference spectrum list. For example, the activity spectrum comparator can be spreadsheet software that is readily available to those of ordinary skill in the art. For example, MicroSoft Excel (MicroSoft Inc., Redmond, Wash.) can be used.

J. Functional Classification

In the methods of the present invention, protein function is indicated by the pattern of ligands that bind to the protein. By using the activity spectrum comparator to compare the observed target activity spectrum with the functional reference spectrum list, the target protein can be functionally classified according to relational data obtained for known proteins. For example, the protein can be classified according to the set of ligands that stabilize the protein against thermal unfolding.

Thus, by comparing a plot of the degree to which each of a multiplicity of molecules or compounds modify the thermal stability of a protein (and therefore bind to the protein) to a plot of the degree to which the same molecules modify the thermal stability of a known protein (and therefore bind to the protein), the class of proteins to which the protein belongs can be deduced.

Alternatively, the protein can be classified by comparing the activity spectrum of the target protein to the activity spectra of known, classified proteins. For example, one can consult databases such as PDR online, Medline, SciFinder, STNExpress, in-house databases, NAPRALERT Online, the *Encyclopedia of Common Natural Ingredients Used in Foods, Drugs and Cosmetics*, 2$^{nd}$ Edition, Leung and Foster, Eds., Wiley Interscience (1996), and the *Handbook of Enzyme Inhibitors, Part A and B*, 2$^{nd}$ Edition, Ellner, Ed., ECH (1990).

The Microplate Thermal Shift Assay and Apparatus

In principle, any means of measuring the effects of incubating a protein in the presence of a panel of probe ligands to determine which probe ligands can affect the stability of the target protein will suffice as a means of functionally classifying proteins. Preferably, the microplate thermal shift assay is used to determine the effect of one or more molecules or ligands on the thermal stability of a target protein. The microplate thermal shift assay is a direct and quantitative technology for assaying the effect of one or more molecules on the thermal stability of a target protein.

The thermal shift assay is based on the ligand-dependent change in the thermal unfolding curve of a receptor, such as a protein or a nucleic acid. When heated over a range of temperatures, a receptor will unfold. By plotting the degree of unfolding as a function of temperature, one obtains a thermal unfolding curve for the receptor. A useful point of reference in the thermal unfolding curve is the temperature midpoint ($T_m$), the temperature at which half of the receptor molecules are unfolded.

Thermal shift assays are based on the ligand-dependent change in the midpoint for thermally induced unfolding curves, $\Delta T_m$, for the ligand-receptor complex (relative to the un-complexed receptor) as an experimental observable that directly relates to the ligand binding affinity, $K_d$, due to the coupling of the ligand binding and receptor unfolding free energy functions (Schellman, J. A., *Biopolymers* 15: 999–1000 (1976); Brandts, J. F., *Biochemistry* 29:6927–6940 (1990)). This thermal physical screening strategy utilizes the thermal stability of ligand-receptor mixtures as an indicator of the binding affinity for the ligand-receptor interactions. These assays have been traditionally carried out one at a time in differential scanning calorimeters (DSC) that monitor the change in heat capacity as proteins undergo temperature induced unfolding transitions (Brandts et al., *Biochemistry* 29:6927–6940 (1990); and Weber, P. et al., *J. Am. Chem. Soc.* 116:2717–2724 (1994)). Alternatively, thermal shift assays can be performed, again one at a time, by employing temperature-regulated optical instruments that monitor the absorbance (Chavan, A. J. et al., *Biochemistry* 33:7193–7202 (1994)); fluorescence (Chavan, A. J. et al., *Biochemistry* 33:7193–7202 (1994); or circular dichroism (Bouvier, M. et al., *Science* 265:398–402 (1994); Morton, A. et al., *Biochemistry* 34:8564–8575 (1995)) changes that occur for the thermally induced unfolding transitions of proteins.

There are many advantages to using the thermal shift assay since it does not require radioactively labeled compounds, nor fluorescent or other chromophobic labels to assist in monitoring binding. The assay takes advantage of thermal unfolding of biomolecules, a general physical chemical process intrinsic to many, if not all, drug target biomolecules. General applicability is an important aspect of this assay since it obviates the necessity to invent a new assay every time a new therapeutic receptor protein becomes available. The assay is particularly well suited for measuring the binding of ligands to non-enzymatic targets, for example growth factor/receptor interactions, where no spectrophotometric assay is usually possible. However, the single assay configuration of the thermal shift methods, as conventionally performed, has limited the utility of this technique, especially for the high throughput screening of compound libraries.

We have been able to greatly accelerate the protein/ligand screening process by developing a generally applicable high throughput ligand-receptor screening strategy in a 96 well plate (or higher density) format that will identify and rank lead compounds based on the thermodynamic stabilization of ligand-receptor complexes.

Ligand binding stabilizes the receptor (Schellman, *J. Biopolymers* 14:999–1018 (1975)). The extent of binding and the free energy of interaction follow parallel courses as a function of ligand concentration (Schellman, J., *Biophysical Chemistry* 45:273–279 (1993); Barcelo, F. et al., *Chem. Biol. Interactions* 74:315–324 (1990)). As a result of stabilization by ligand, more energy (heat) is required to unfold the receptor. Thus, ligand binding shifts the thermal unfolding curve. That is, ligand binding increases the thermal stability of the protein. This property can be exploited to determine whether a ligand binds to a receptor: a change, or "shift", in the thermal unfolding curve, and thus in the $T_m$, suggests that a ligand binds to the receptor.

The thermodynamic basis for the thermal shift assay has been described by Schellman, J. A. (*Biopolymers* 15:999–1000 (1976)), and also by Brandts et al. (*Biochemistry* 29:6927–6940 (1990)). Differential scanning calorimetry studies by Brandts et al. (*Biochemistry* 29:6927–6940 (1990)) have shown that for tight binding systems of 1:1 stoichiometry, in which there is one unfolding transition, one can estimate the binding affinity at $T_m$ from the following expression:

$$K_L^{T_m} = \frac{\exp\left\{-\frac{\Delta H_u^{T_0}}{R}\left[\frac{1}{T_m} - \frac{1}{T_0}\right] + \frac{\Delta C_{pu}}{R}\left[\ln\left(\frac{T_m}{T_0}\right) + \frac{T_0}{T_m} - 1\right]\right\}}{L_{T_m}}$$ (equation 1)

where
$K_L^{T_m}$=the ligand association constant at $T_m$;
$T_m$=the midpoint for the protein unfolding transition in the presence of ligand;
$T_0$=the midpoint for the unfolding transition in the absence of ligand;
$\Delta H_u^{T_0}$=the enthalpy of protein unfolding in the absence of ligand at $T_0$;
$\Delta C_{pu}$=the change in heat capacity upon protein unfolding in the absence of ligand;
$[L_{T_m}]$=the free ligand concentration at $T_m$; and
R=the gas constant.

This expression was found to be useful for the structure based design of azobenzene ligands for streptavidin where DSC scans of various ligand/streptavidin mixtures facilitated the measurement of binding affinity at $T_m$ (Weber, P. et al., *J. Am. Chem. Soc.* 116:2717–2724 (1994)). These measurements were checked further by performing mixing or isothermal titrating calorimetry experiments which yielded binding affinities consistent with those determined by DSC. The ease and reproducibility of using protein thermal unfolding to estimate ligand binding affinity impressed upon us the potential of further extending this approach for becoming a more general drug discovery tool.

The parameters $\Delta H_u$ and $\Delta C_{pu}$ are usually observed from DSC experiments and are specific for each protein. Calorimetric measurements of $\Delta H_u$ and $\Delta C p_u$ are the most accurate estimates of these parameters because calorimeters typically collect unfolding data every 0.1° C. However, the parameters, $\Delta H_u$ and $\Delta C_{pu}$ can also be estimated in the microplate thermal shift assay, in which case the $\Delta H_u$ will not be a calorimetric enthalpy but a comparable van't Hoff enthalpy based on unfolding data collected at every 2.0° C. using the current protocol. Moreover, even in the absence of optimum data for $\Delta H_u$ and $\Delta C_{pu}$, these parameters are constants specific to the protein involved in the compound screening and will therefore be unchanged from well to well, resulting in no influence on calculations of the relative values of binding affinities, i.e., $K_L$ at $T_m$.

Besides the parameters $\Delta H_u$ and $\Delta C_{pu}$, it is also necessary to obtain estimates of $T_m$ and $T_0$ to solve for $K^{T_m}_L$ in equation 1. This is accomplished through the use of non-linear least squares computer fits of the unfolding data for each individual well using the following equation:

$$y(T) = y_u + \frac{(y_f - y_u)}{1 + \exp\left(\left[\frac{-\Delta H_u}{R}\right]\left[\frac{1}{T} - \frac{1}{T_m}\right] + \left[\frac{\Delta C_{pu}}{R}\right]\left[\left(\frac{T_m}{T} - 1\right) + \ln\left(\frac{T}{T_m}\right)\right]\right)}$$ Equation 2

Equation 2 employs five fitting parameters, $\Delta H_u$, $\Delta C_{pu}$, $T_m$, $y_f$ and $y_u$, where $y_f$ and $y_u$ are the pre-transitional and post-transitional fluorescence levels, respectively. The computer fits are determined by floating these parameters to arrive at the minimum of the sum of the squares of the residuals by employing the Levenberg-Marquardt algorithm. The $T_0$ values are obtained for wells that contain no added ligand and are set as the reference. Commercially available curve-fitting software is readily available to one of ordinary skill in the art. For example, Kaleidograph 3.0 (Synergy, Reading, Pa.) can be used.

It is also possible to calculate the ligand association equilibrium constant at any temperature, $K_L$ at T, the ligand association equilibrium constant at $T_m$, using equation 3, if mixing calorimetry data for the binding enthalpy at T, $\Delta H_L$, and the change in heat capacity upon ligand binding, $\Delta C_{pL}$, are known (Brandts & Lin, 1990).

$$K_L^T = K_L^{T_m}\exp\left\{-\frac{\Delta H_L^T}{R}\left[\frac{1}{T} - \frac{1}{T_m}\right] + \frac{\Delta C_{pL}}{R}\left[\ln\left(\frac{T}{T_m}\right) - \frac{T}{T_m} + 1\right]\right\}$$ Equation 3 where
K=the ligand association constant at any temperature, T.
$K_L^{T_m}$=the ligand association constant at $T_m$.
$T_m$=the midpoint for the protein unfolding transition in the presence of ligand.
$\Delta H_L^T$=the enthalpy of ligand binding at temperature, T.
$\Delta C_{pL}$=the change in heat capacity upon binding of ligand.
R=gas constant The second exponential term of equation 3 is usually small enough to be ignored so that approximate values of $K_L$ at T can be obtained using just the first exponential term, and equation 3 reduces to equation 4:

$$K_L^T = K_L^{T_m}\exp\left[-\frac{\Delta H_L^T}{R}\left[\frac{1}{T} - \frac{1}{T_m}\right]\right]$$ Equation 4

The parameter $\Delta H_L^T$ can be measured using a isothermal titrating calorimetry, using a calorimetric device such as the Omega (MicroCal; Northampton, Mass.). When calorimetric data are not available, $\Delta H_L^T$ can be estimated to be about −10.0 kcal/mol, which is an average binding enthalpy (Wiseman et al., *Anal. Biochem.* 179:131–137 (1989)).

Preferably, fluorescence spectrometry is used to monitor thermal unfolding. The fluorescence methodology is more sensitive than the absorption methodology. The use of intrinsic protein fluorescence and fluorescence probe molecules in fluorescence spectroscopy experiments is well known to those skilled in the art. See, for example, Bashford, C. L. et al., *Spectrophotometry and Spectrofluorometry: A Practical Approach*, IRL Press Ltd., pub., pp. 91–114 (1987); Bell, J. E., *Spectroscopy in Biochemistry, Vol. I*, CRC Press, pub., pp. 155–194 (1981); Brandts, L. et al., *Ann. Rev. Biochem.* 41:843 (1972).

The microplate thermal shift assay is further described in U.S. patent Appl. No. 08/853,464, filed May 9, 1997, and in international patent Appl. No. PCT/US97/08154 (published Nov. 13, 1997 as publication no. WO 97/42500), which are hereby incorporated by reference in their entirety.

Spectral readings, preferably fluorescence readings, can be taken on all of the samples on a carrier simultaneously. Alternatively, readings can be taken on samples in groups of at least two at a time.

A fluorescence imaging system, for example, a fluorescence emission imaging system, can be used to monitor the thermal unfolding of a target molecule or a receptor. Fluorescence imaging systems are well known to those skilled in the art. For example, the ALPHAIMAGER™ Gel Documentation and Analysis System (Alpha Innotech, San Leandro, Calif.) employs a high performance charge coupled device (CCD) camera with 768×494 pixel resolution. The charge coupled device camera is interfaced with a computer and images are analyzed with Image analysis software™. The CHEMIIMAGER™ (Alpha Innotech) is a cooled charge coupled device that performs all of the functions of the ALPHAIMAGER™ and in addition captures images of chemiluminescent samples and other low intensity samples. The CHEMIIMAGER™ charge coupled device includes a Pentium processor (1.2 Gb hard drive, 16 Mb RAM), AlphaEase™ analysis software, a light tight cabinet, and a UV and white light trans-illuminator. For example, the MRC-1024 UV/Visible Laser Confocal Imaging System (BioRad, Richmond, Calif.) facilitates the simultaneous imaging of more than one fluorophore across a wide range of illumination wavelengths (350 to 700 nm). The Gel Doc 1000 Fluorescent Gel Documentation System (BioRad, Richmond, Calif.) can clearly display sample areas as large as 20×20 cm, or as small as 5×4 cm. At least two 96 well microplates can fit into a 20×20 cm area. The Gel Doc 1000 system also facilitates the performance of time-based experiments.

A fluorescence imaging system, for example, a fluorescence emission imaging system, can be used to monitor receptor unfolding in a microplate thermal shift assay. In this embodiment, a plurality of samples is heated simultaneously between 25 to 110° C. A fluorescence emission reading is taken for each of the plurality of samples simultaneously. For example, the fluorescence in each well of a 96 or a 384 well microplate can be monitored simultaneously. Alternatively, fluorescence readings can be taken continuously and simultaneously for each sample. At lower temperatures, all samples display a low level of fluorescence. As the temperature is increased, the fluorescence in each sample increases. Wells which contain ligands which bind to the target molecule with high affinity shift the thermal unfolding curve to higher temperatures. As a result, wells which contain ligands which bind to the target molecule with high affinity fluoresce less, at a given temperature above the $T_m$ of the target molecule in the absence of any ligands, than wells which do not contain high-affinity ligands. If the samples are heated in incremental steps, the fluorescence of all of the plurality of samples is simultaneously imaged at each heating step. If the samples are heated continuously, the fluorescent emission of all of the plurality of samples is simultaneously imaged during heating.

A thermal shift assay can be performed in a volume of 100 µL volumes. For the following reasons, however, it is preferable to perform a thermal shift assay in a volume of 1–10 µL. First, approximately 10- to 100-fold less protein is required for the miniaturized assay. Thus, only ~4 to 40 pmole of protein are required (0.1 µg to 1.0 µg for a 25 kDa protein) for the assay (i.e. 1 to 10 µL working volume with a target molecule concentration of about 1 to about 4 µM). Thus, 1 mg of protein can be used to conduct 1,000 to 10,000 assays in the miniaturized format. This is particularly advantageous when the target molecule is available in minute quantities.

Second, approximately 10- to 100-fold less ligand is required for the miniaturized assay. This advantage is very important to researchers when screening valuable combinatorial libraries for which library compounds are synthesized in minute quantities. In the case of human a-thrombin, the ideal ligand concentration is about 50 µM, which translates into 25–250 pmoles of ligand, or 10–100 ng (assuming a MW of 500 Da) of ligand per assay in the miniaturized format.

Third, the smaller working volume allows the potential of using larger arrays of assays because the miniaturized assay can fit into a much smaller area. For example, 384 well (16×24 array) or 864 well (24×36 array) plates have the same dimensions as the 96 well plates (8.5×12.5 cm). The 384 well plate and the 864 well plate allows the user to perform 4 and 9 times as many assays, respectively, as can be performed using a 96 well plate. Alternatively, plates with more wells, such as 1536 well plates (32×48 arrays; Matrix Technologies Corp.), can be used. A 1536 well plate will facilitate sixteen times the throughput afforded by a 96 well plate.

Thus, using the 1536 well plate configuration, assay speed can be increased by about 16 times, relative to the speed at which the assay can be performed using the 96 well format. The 8×12 assay array arrangement (in a 96-well plate) facilitates the performance of 96 assays/hr, or about 2300 assays/24 hours. The 32×48 array assay arrangement facilitates the performance of about 1536 assays hr., or about 37,000 assays/24 hours can be performed using a 32×48 assay array configuration.

The assay volume can be 1–100 µL. Preferably, the assay volume is 1–50 µL. More preferably, the assay volume is 1–25 µL. More preferably still, the assay volume is 1–10 µL. More preferably still, the assay volume is 1–5 µL. More preferably still, the assay volume is 5 µL. Most preferably, the assay volume is 1 µL or 2 µL.

Alternatively, the assay is performed in V-bottom polycarbonate, polystyrene, or polyproplene plates or dimple plates. A dimple plate is a plate that contains a plurality of round-bottom wells that hold a total volume of 15 µL.

The microplate thermal shift assay is performed by (a) contacting a protein with one or more of a multiplicity of different molecules in each of a multiplicity of containers; (b) heating the multiplicity of containers from step(a), preferably simultaneously; (c) measuring in each of the containers a physical change associated with the thermal unfolding of the target molecule resulting from heating; (d) generating a thermal unfolding curve for the target molecule as a function of temperature for each of the containers; and (e) comparing each of the unfolding curves in step (d) to (1) each of the other thermal unfolding curves and to (2) the thermal unfolding curve obtained for the protein in the absence of any of the multiplicity of different molecules; and (f) determining whether any of the multiplicity of different molecules modifies the thermal stability of the protein, wherein a modification in thermal stability is indicated by a shift in the thermal unfolding curve.

Step (d) may further comprise determining a midpoint temperature ($T_m$) from the thermal unfolding curve. Step (e) may further comprise comparing the $T_m$ of each of the unfolding curves in step (d) to (1) the $T_m$ of each of the other thermal unfolding curves and to (2) the $T_m$ of the thermal unfolding curve obtained for the target protein in the absence of any of the different molecules.

To practice the methods of the present invention using fluorescence spectroscopy or imaging, step (a) comprises contacting the target protein with a fluorescence probe molecule present in each of the multiplicity of containers and step (c) comprises (c1): exciting the fluorescence probe molecule, in each of the multiplicity of containers, with light; and (c2) measuring the fluorescence from each of the multiplicity of containers. Fluorescence, for example, fluorescence emission, can be measured from each of the multiplicity of containers one container at a time, from a subset of the multiplicity of containers simultaneously, or from each of the multiplicity of containers simultaneously.

To generate an activity spectrum, molecules are ranked according to the degree to which they stabilize the target protein against thermal unfolding. After the molecules are ranked, the activity spectrum of the target protein for the molecules in the functional probe library is compared to one or more functional reference spectrum lists.

Suitable heating apparatuses for practicing the methods of the present invention are well known to those of ordinary skill in the art. For example, the ROBOCYCLER® Gradient Temperature Cycler (Stratagene, La Jolla, Calif.) (see U.S. Pat. No. 5,525,300) can be used. Alternatively, a temperature gradient heat block can be used (see U.S. Pat. No. 5,255,976). Fluorescence can be read using any suitable fluorescence spectroscopy device. For example, the CytoFluor II apparatus (PerSeptive Biosystems, Framingham, Mass.) can be used.

The element upon which the sample carrier is heated can be any element capable of heating samples rapidly and in a reproducible fashion. In the present invention, a plurality of samples is heated simultaneously. The plurality of samples can be heated on a single heating element. Alternatively, the plurality of samples can be heated to a given temperature on one heating element, and then moved to another heating element for heating to another temperature. Heating can be accomplished in regular or irregular intervals. To generate a smooth unfolding curve, the samples should be heated evenly, in intervals of 1 or 2° C. The temperature range across which the samples can be heated is from 4 to 110° C. Spectral readings, and particularly fluorescence readings, are taken after each heating step. Samples can be heated and read by the spectral device, for example, a fluorescence imaging camera, in a continuous fashion. Alternatively, after each heating step, the samples may be cooled to a lower temperature prior to taking the spectral readings. Preferably, the samples are heated continuously and spectral readings are taken while the samples are being heated.

Spectral, e.g., fluorescence, readings can be taken on all of the samples in the carrier simultaneously. Alternatively, readings can be taken on samples in groups of at least two at a time. Finally, the readings can be taken one sample at a time.

Preferably, the instrument used to perform the microplate thermal shift assay consists of a scanner and a control software system. Fluorescence, for example, fluorescence emission, can be detected by a photomultiplier tube in a light-proof detection chamber. The software runs on a personal computer and the action of the scanner is controlled through the software.

Figure 2:
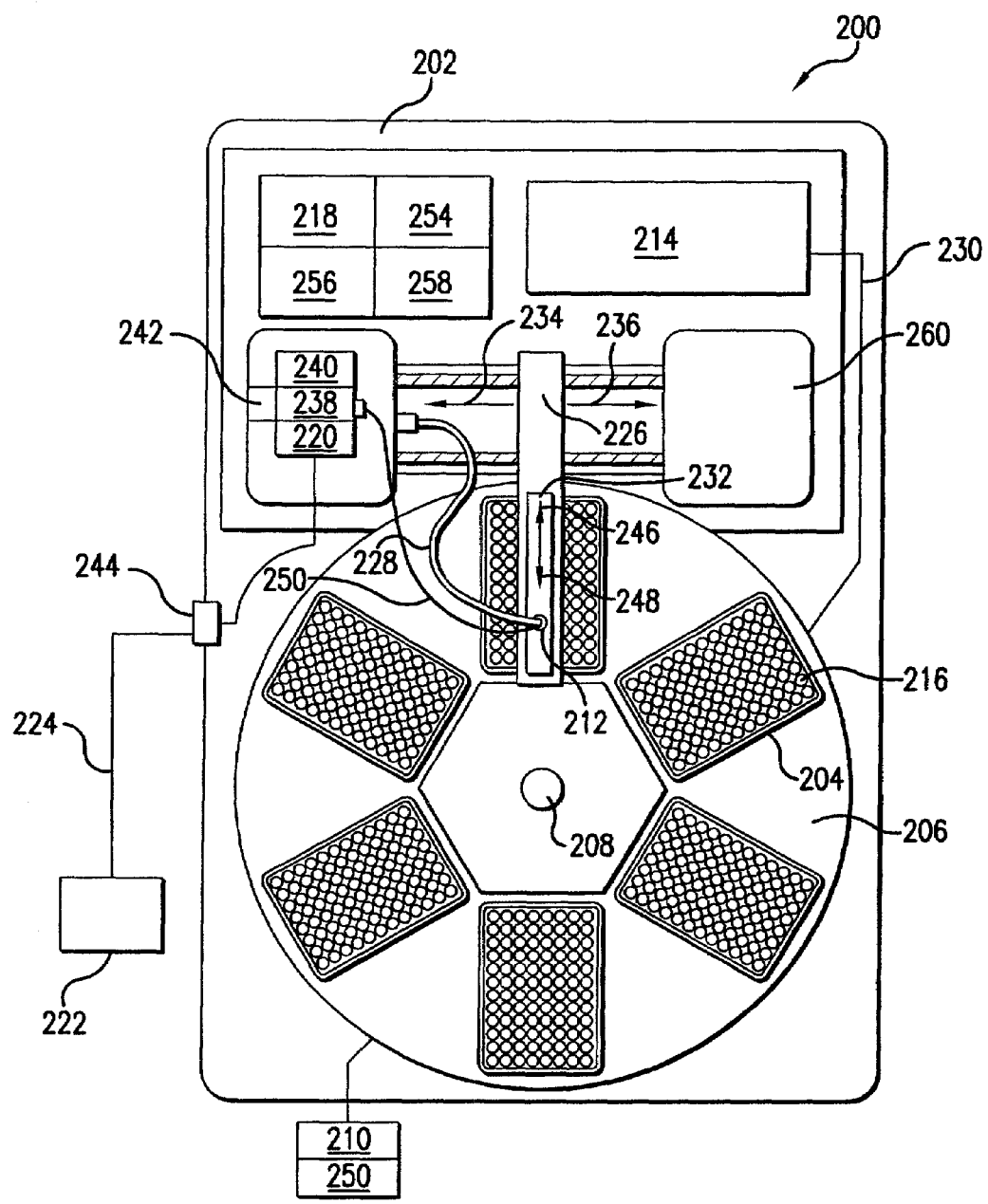
FIG. 2 is a schematic diagram illustrating a top view of an assay apparatus that can be used to practice the microplate thermal shift assay.

An exemplary apparatus 200 is shown in FIG. 2. A precision X-Y mechanism scans the microplate with a sensitive fiber-optic probe to quantify the fluorescence in each well. The microplate and samples can remain stationary during the scanning of each row of the samples, and the fiber-optic probe is then moved to the next row. Alternatively, the microplate and samples can be moved to position a new row of samples under the fiber-optic probe. The scanning system is capable of scanning 96 samples in under one minute. The scanner is capable of holding a plurality of excitation filters and a plurality of emission filters to measure the most common fluorophores. Thus, fluorescence emission readings can be taken one sample at a time, or on a subset of samples simultaneously.

The heat conducting element or block upon which the sample carrier is heated can be any element capable of heating samples rapidly and reproducibly. The plurality of samples can be heated on a single heating element. Alternatively, the plurality of samples can be heated to a given temperature on one heating element, and then moved to another heating element for heating to another temperature. Heating can be accomplished in regular or irregular intervals. To generate a smooth unfolding curve, the samples should be heated evenly, in intervals of 1 or 2° C. The temperature range across which the samples can be heated is from 4 to 110° C.

Preferably, a plurality of samples is heated simultaneously. If samples are heated in discrete temperature intervals, in a stairstep fashion, spectral readings are taken after each heating step. Alternatively, after each heating step, the samples may be cooled to a lower temperature prior to taking the spectral readings. Alternatively, samples can be heated in a continuous fashion and spectral readings are taken during heating.

The assay apparatus can be configured so that it contains a single heat conducting block. Alternatively, the assay apparatus can be configured so that it contains a plurality of heat conducting blocks upon a movable platform. The platform may be a translatable platform that can be translated, for example, by a servo driven linear slide device. An exemplary linear slide device is model SA A5M400 (IAI America, Torrance, Calif.). In this embodiment, the sensor receives spectral emissions from each of the samples on a given heat conducting block. The platform is then translated to place another heat conducting block and its accompanying samples under the sensor so that it receives spectral emissions from each of the samples on that heating block. The platform is translated until spectral emissions are received from the samples on all heat conducting blocks Alternatively, the platform may by a rotatable platform, as shown in FIG. 2, that may be rotated, for example, by a servo driven axle. In the latter embodiment, the sensor receives spectral emissions from each of the samples on a given heat conducting block. The platform is then rotated to place another heat conducting block and its accompanying samples under the sensor so that it receives spectral emissions from each of the samples on that heating block. The platform is rotated until spectral emissions are received from the samples on all heat conducting blocks.

In apparatus 200, a plurality of heat conducting blocks 204, each of which includes a plurality of wells for a plurality of samples 210, is mounted on a rotatable platform or carousel 206. Platform or carousel 206 can be composed of a heat conducting material, such as the material that heat conducting block 204 is composed of. Axle 208 is rotatably connected to base 202. Rotatable platform 206 is axially mounted to rotate about axle 208. Rotation of axle 208 is controlled by a servo controller 210. Servo controller 210 is controlled by a computer controller 250 in a manner well known to one of skill in the relevant arts. Computer controller 250 causes servo controller 210 to rotate axle 208 thereby rotating rotatable platform 206. In this manner, heat conducting blocks 204 are sequentially placed under fiber optic probe 212.

Each of the plurality of heat conducting blocks 204 can be controlled independently by temperature controller 214. Thus, the temperature of a first heat conducting block 204 can be higher or lower than the temperature of a second heat conducting block 204. Similarly, the temperature of a third heat conducting block 204 can be higher or lower than the temperature of either first or second heat conducting block 204.

Temperature controller 214 is connected to heat conducting block 204 by a thermoelectric connection 230. Under the action of temperature controller 214, the temperature of heat conducting block 204 can be increased, decreased, or held constant. Temperature controller 214 can be configured to adjust the temperature of rotatable platform 206. In such a configuration, when rotatable platform 206 is heated, heat conducting blocks 204 are also heated. Alternatively, the temperature of each of heat conducting blocks 204 can be controlled by a circulating water system such as that noted above. Particularly, the temperature of heat conducting block 204 can be changed by temperature controller 214 in accordance with a pre-determined temperature profile. Preferably, temperature computer controller 214 is implemented using a computer system.

As used herein, the term "temperature profile" refers to a change in temperature over time. The term "temperature profile" encompasses continuous upward or downward changes in temperature, both linear and non-linear changes. The term also encompasses any stepwise temperature change protocols, including protocols characterized by incremental increases or decreases in temperature during which temperature increases or decreases are interrupted by periods during which temperature is maintained constant. In the apparatus shown in FIG. 2, the temperature profile can be pre-determined by programming temperature computer controller 214. For example, temperature profiles can be stored in a memory device of temperature controller 214, or input to temperature controller 214 by an operator.

Assay apparatus 200 also includes a light source 218 for emitting an excitatory wavelength of light. Excitatory light from light source 218 excites samples 216 with excitatory light. Any suitable light source can be used. Excitatory light causes a spectral emission from samples 216. The spectral emission can be electromagnetic radiation of any wavelength in the electromagnetic spectrum. Preferably, the spectral emission is fluorescent, ultraviolet, or visible light. Most preferably, the spectral emission is fluorescence emission.

A sensor is removably attached to a sensor armature 226. An exemplary sensor is a fiber optic probe 212. Fiber optic probe 212 includes a fiber optic cable capable of transmitting excitatory light to samples 216, and a fiber optic cable capable of receiving a spectral emission from samples 216. Electromagnetic radiation is transmitted from excitatory light source 218 to fiber optic probe 212 by excitatory light input fiber optic cable 228.

An excitatory light filter servo controller 258 controls the aperture of excitatory light filter 256. Excitatory light source 218 and excitatory light filter servo controller 258 are communicatively and operatively connected to excitatory light computer controller 254. Computer controller 254 controls the wavelength of excitatory light transmitted to samples 216 by controlling excitatory light filter servo controller 258. Excitatory light is transmitted through excitatory light input fiber optic cable 228 to fiber optic probe 212 for transmission to samples 216.

The spectral emission from samples 216 is received by fiber optic probe 212 and is transmitted to a spectral emission filter 238 by output fiber optic cable 250. A spectral emission servo controller 240 controls the aperture of spectral emission filter 238, thereby controlling the wavelength of the spectral emission that is transmitted to photomultiplier tube 220. Spectral emission servo controller 240 is controlled by a computer controller 242.

The spectral emission from samples 216 is transmitted from photomultiplier tube 220. Electrical output 244 connects photomultiplier tube 220 to electric connection 224. Electric connection 224 connects electrical output 244 to computer 222. Driven by suitable software, computer 222 processes the spectral emission signal from samples 216. Exemplary software is a graphical interface that automatically analyzes fluorescence data obtained from samples 216. Such software is well known to those of ordinary skill in the art. For example, the CytoFluor™II fluorescence multi-well plate reader (PerSeptive Biosystems, Framingham, Mass.) utilizes the Cytocalc™ Data Analysis System (PerSeptive Biosystems, Framingham, Mass.). Other suitable software includes, MicroSoft Excel or any comparable software.

A sensor armature relative movement means 260 moves sensor armature 226 in directions 234 and 236. A second relative movement means 232 moves sensor armature 226 in directions 246 and 248 so that fiber optic probe 212 can be moved to detect spectral emissions from samples 216.

As discussed above, the spectral receiving means or sensor of the assay apparatus of the present invention can comprise a photomultiplier tube. Alternatively, the spectral receiving means or sensor can include a charge coupled device (CCD). In still another alternative, the spectral receiving means or sensor can include a diode array. A CCD is made of semi-conducting silicon. When photons of light fall on it, free electrons are released.

Further, a CCD camera can be used to image fluorescence, such as fluorescence emission. High resolution CCD cameras can detect very small amounts of electromagnetic energy, whether it originates from distance stars, is diffracted by crystals, or is emitted by fluorophores. As an electronic imaging device, a CCD camera is particularly suitable for fluorescence emission imaging because it can detect very faint objects, affords sensitive detection over a broad spectrum range, affords low levels of electromagnetic noise, and detects signals over a wide dynamic range—that is, a charge coupled device can simultaneously detect bright objects and faint objects. Further, the output is linear so that the amount of electrons collected is directly proportional to the number of photons received. This means that the image brightness is a measure of the real brightness of the object, a property not afforded by, for example, photographic emulsions. Suitable CCD cameras are available from Alpha-Innotech (San Leandro, Calif.), Stratagene (La Jolla, Calif.), and BioRad (Richmond, Calif.).

Apparatuses useful for practicing the microplate thermal shift assay are further described in U.S. patent application Ser. No. 08/853,459, filed May 9, 1997, and in international patent Appl. No. PCT/US97/08154 (published Nov. 13, 1997 as publication no. WO 97/42500), which are hereby incorporated by reference in their entirety.

Having now generally described the invention, the same will become more readily understood by reference to the following specific examples which are included herein for purposes of illustration only and are not intended to be limiting unless otherwise specified.

EXAMPLE 1

Wide Cross Target Utility of Microplate Thermal Shift Assay

A number of different therapeutic protein targets have been tested in the microplate thermal shift assay, to date, and are listed in Table 2. They include a variety of different proteins, with a wide diversity of in vivo function. Included here are various serine proteases, a DNA binding protein (lac repressor), two growth factors (basic fibroblast growth factor (bFGF) and acidic fibroblast growth factor (aFGF)), and a growth factor receptor (domain II of the fibroblast growth factor receptor 1 (D(II)FGFR1)).

TABLE 2

Therapeutic Targets Analyzed by the Microplate Thermal Shift Assay

| Targets | MW | Assays/mg (in 10 uL format) |
|---|---|---|
| α-Thrombin | 37.0 kDa | 1430 0.7 ug/assay (20 pmol) |
| Factor D | 25.0 kDa | 1000 1.0 ug/assay (40 pmol) |
| Factor Xa | 45.0 kDa | 1667 0.6 ug/assay (7 pmol) |
| bFGF | 17.5 kDa | 2000 0.5 ug/assay (29 pmol) |
| D(II)FGFR1 | 13.5 kDa | 588 1.7 ug/assay (126 pmol) |
| lac Repressor | 77.0 kDa | 1200 0.8 ug/assay (10 pmol) |
| Urokinase | 28.0 kDa | 714 1.4 ug/assay (50 pmol) |
| NFkB protein | 65.0 kDa | 3030 0.33 ug/assay (5 pmol) |
| GLP1 receptor | 26.0 kDa | |
| MHC II | 45.0 kDa | |
| von Willebrand Factor | 500 kDa | 400 2.5 ug/assay |
| aFGF | 18.0 kDa | |

The molecular weights of the target proteins range from 13.5 kDa to about 500 kDa. On average, it was possible to conduct 1322 assays per 1.0 mg of protein using a 10 μL assay volume. The number of assays that can be conducted can be doubled if the 5 μL assay format is employed.

All microplate thermal shift assays were performed in polycarbonate V-bottom 96 well plates using 200 μM 1,8-ANS as the fluorescent probe for monitoring the thermal unfolding transitions for the protein/ligand mixtures. Changes in fluorescence emission at 460 μm were monitored with a CytoFluor II (PerSeptive Biosystems) fluorescence plate reader (excitation at 360 μm), and the temperature was raised in 2° C. increments with the RoboCycler® Gradient Temperature Cycler (Stratagene, La Jolla, Calif.).

A number of other proteins have been assayed using the microplate thermal shift assay, including the following proteins from the following classes: serine proteases (thrombin, Factor Xa, Factor D, urokinase, trypsin, chymotrypsin, subtilisin); cell surface receptors (FGF receptor 1, MHC Class II, GLP 1 receptor, β-2 adrenergic receptor, fibronectin receptor (IibIIIa)); growth factors (aFGF, bFGF); DNA binding proteins (lac repressor, NF-κ-B, helicase); motor proteins (myosin, helicase); oxido-reductases (horseradish peroxidase, cytochrome c, lactate dehydrogenase, lactoperoxidase, malate dehydrogenasease, cholesterol oxidase, glyceraldehyde 3-phosphate dehydrogenasee, phosphoenolpyruvate carboxylase, dihydrofolate reductase); carbohydrate modifications (cellulase, α-amylase, hyaluronidase, β-glucosidase, invertase); immunoglobulins(IgGFab, IgG-Fc); DNAses (DNase I, DNase II) RNAses (RNase A); intracellular calcium receptors (calmodulin, S100 protein); neurotransmitter hydrolase (acetylcholinesterase); free radical scavenger (superoxide dismutase); biotin binding protein (streptavidin); oxygen binding protein (myoglobin); and protease inhibitor (trypsin inhibitor).

EXAMPLE 2

Multi-ligand Binding Interactions with a Single Target Protein

The near universal utility of the microplate thermal shift assay technology is also illustrated for multi-ligand binding interactions that many times occur within a single protein molecule. The ability to assess the binding of many different kinds of ligands to a single protein without re-tooling the assay is a great advantage of this technology and easily lends itself to the task of assigning function to a protein for which nothing is known other than the primary sequence. Knowledge for the binding of different ligands will help in the evaluation of the function of a sample protein derived from genomics information.

As previously demonstrated, the microplate thermal shift assay can be used to screen ligands for binding to single sites on target proteins. However, based upon the near additivity of the free energy of ligand binding and protein unfolding, it is also possible to employ the microplate thermal shift assay to analyzing multi-ligand binding interactions on a target protein. In principle, if the free energy of binding of different ligands binding to the same protein are nearly additive then one can analyze multi-ligand binding systems either non-cooperative or cooperative (positive or negative).

In this regard, human thrombin is an ideal system to test the utility of the assay for analysis of multi-ligand binding interactions because it has at least four different binding sites: (1) the catalytic binding site; (2) the fibrin binding site (exosite I); (3) the heparin binding site (exosite II); (4) the Na+ binding site, located about 15 Å from the catalytic site.

First, the binding of individual ligands was determined. 3DP4660, Hirugen (hirudin 53–64) (Sigma), and heparin 5000 (CalBiochem), bind to the catalytic site, the fibrin binding site and the heparin binding site, respectively of thrombin.

A stock thrombin solution was diluted to 1 μM in 50 mM Hepes, pH 7.5, 0.1 M NaCl, 1 mM CaCl$_2$, and 100 μM 1,8-ANS. Each thrombin ligand was included singly and in various combinations to 1 μM thrombin solutions at final concentrations of 50 μM each, except for heparin 5000, which was 200 μM. 100 μL of thrombin or thrombin/ligand(s) solution was dispensed into wells of a 96-well V-bottom polycarbonate microtiter plate. The contents were mixed by repeated uptake and discharge in a 100 μL pipette tip. Finally, one drop of mineral oil (Sigma, St. Lois, Mo.) was added on top of each reaction well to reduce evaporation from samples at elevated temperatures. The plate was subjected to 3 minutes of heating in a RoboCycler® Gradient Temperature Cycler (Stratagene, La Jolla, Calif.) thermal block, with which a temperature gradient was created across the microplate, followed by 30 seconds cooling at 25° C., and subsequent reading in a fluorescence plate reader. Data were analyzed by non-linear least squares fitting.

Figure 3:
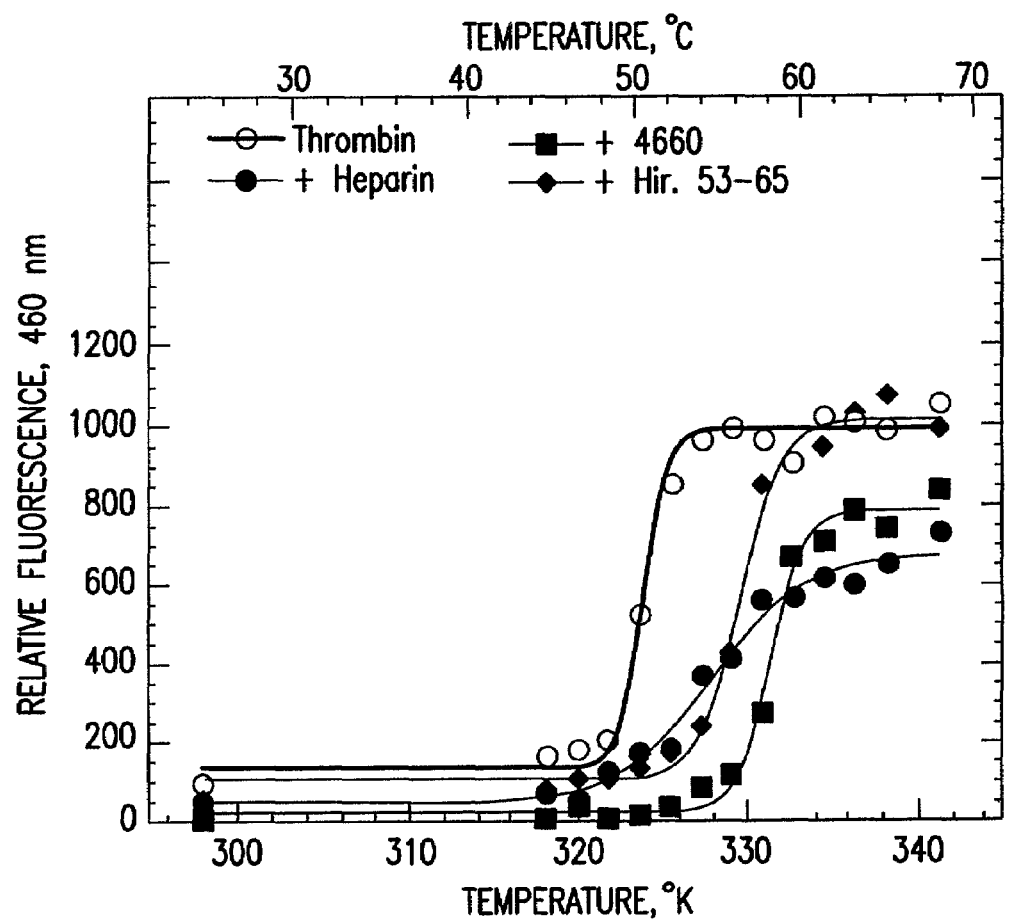
FIG. 3 shows the results of microplate thermal shift assays of single ligand binding interactions to three different classes of binding sites for human α-thrombin.

The results of these individual binding reactions are shown in FIG. 3. The rank order of binding affinity was 3DP-4660>hirugen>heparin 5000, corresponding to $K_d$ of 15 nM, 185 nM and 3434 nM, respectively, for the ligands binding at each $T_m$ (see Equation (1)).

Figure 4:
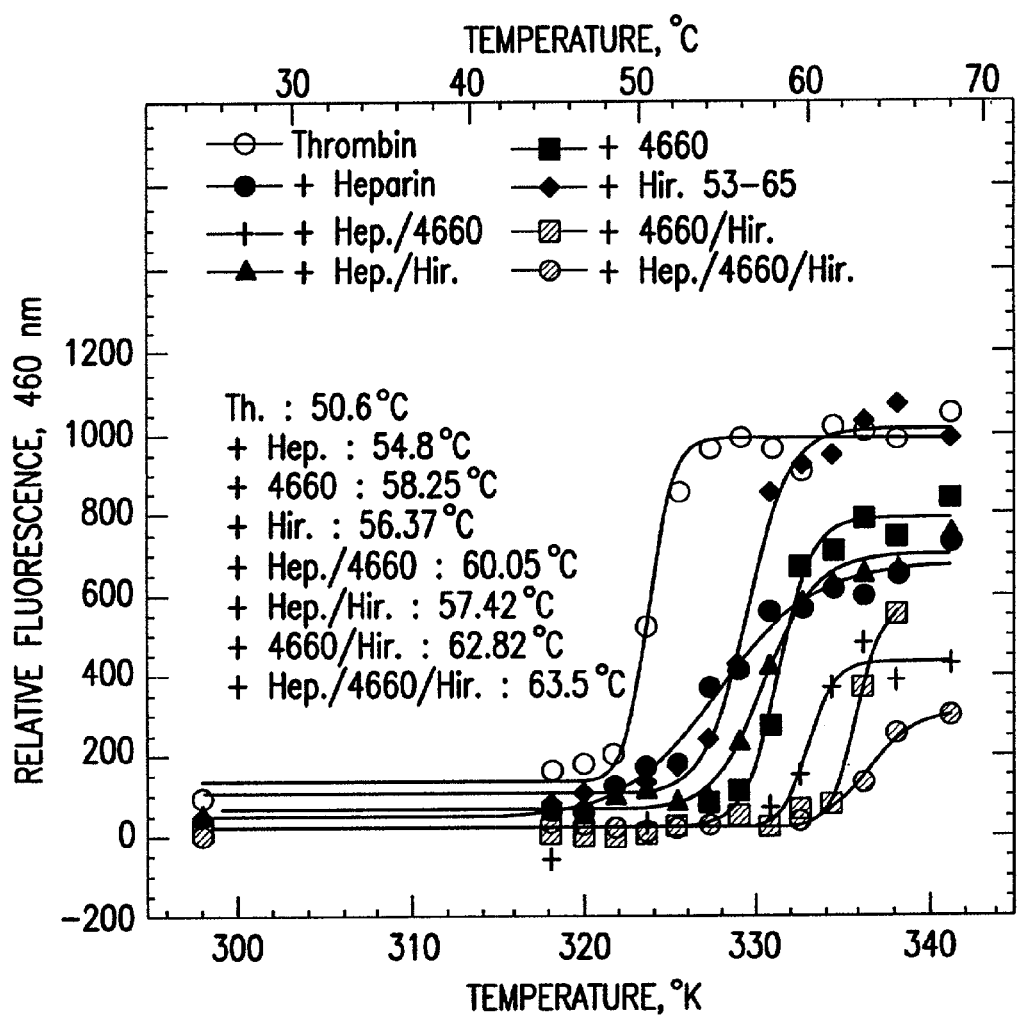
FIG. 4 shows the results of microplate thermal shift assays of multi-ligand binding interactions for human α-thrombin.
Figure 6A:
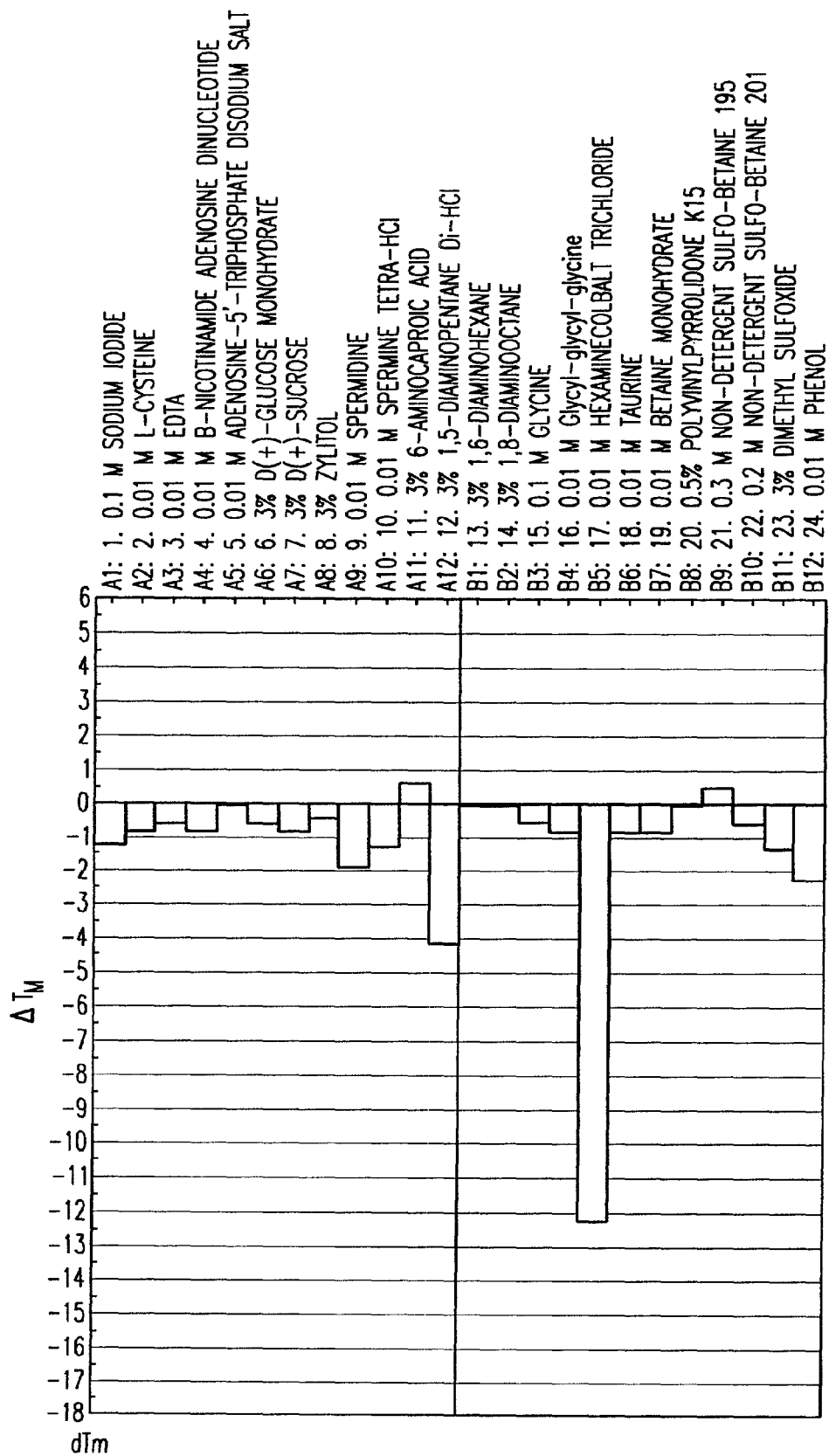
FIGS. 6A–6D show the activity spectrum for Factor Xa that was generated using the compounds in plate 1 of the functional probe library.
Figure 6B:
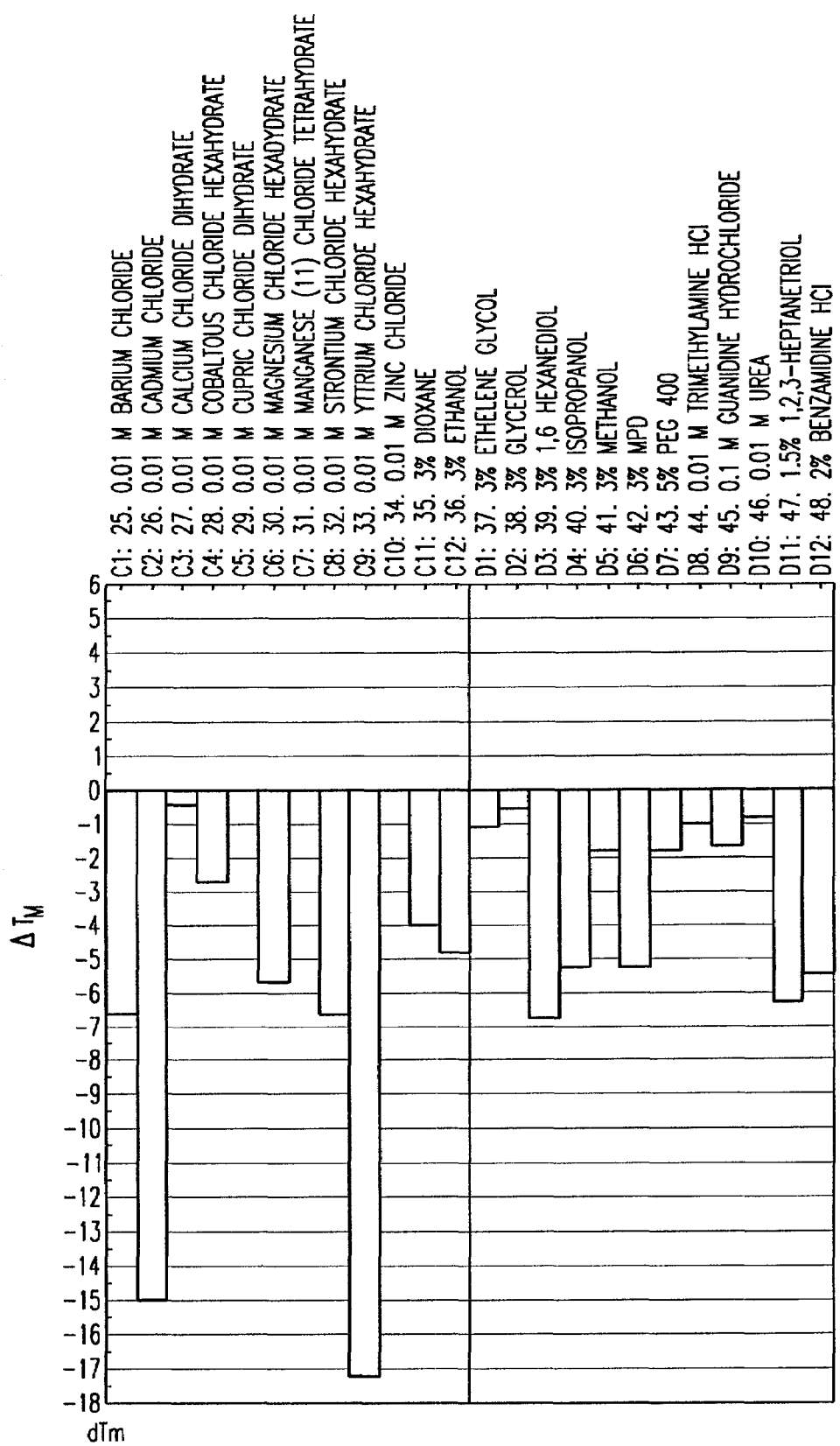
Figure 6C:
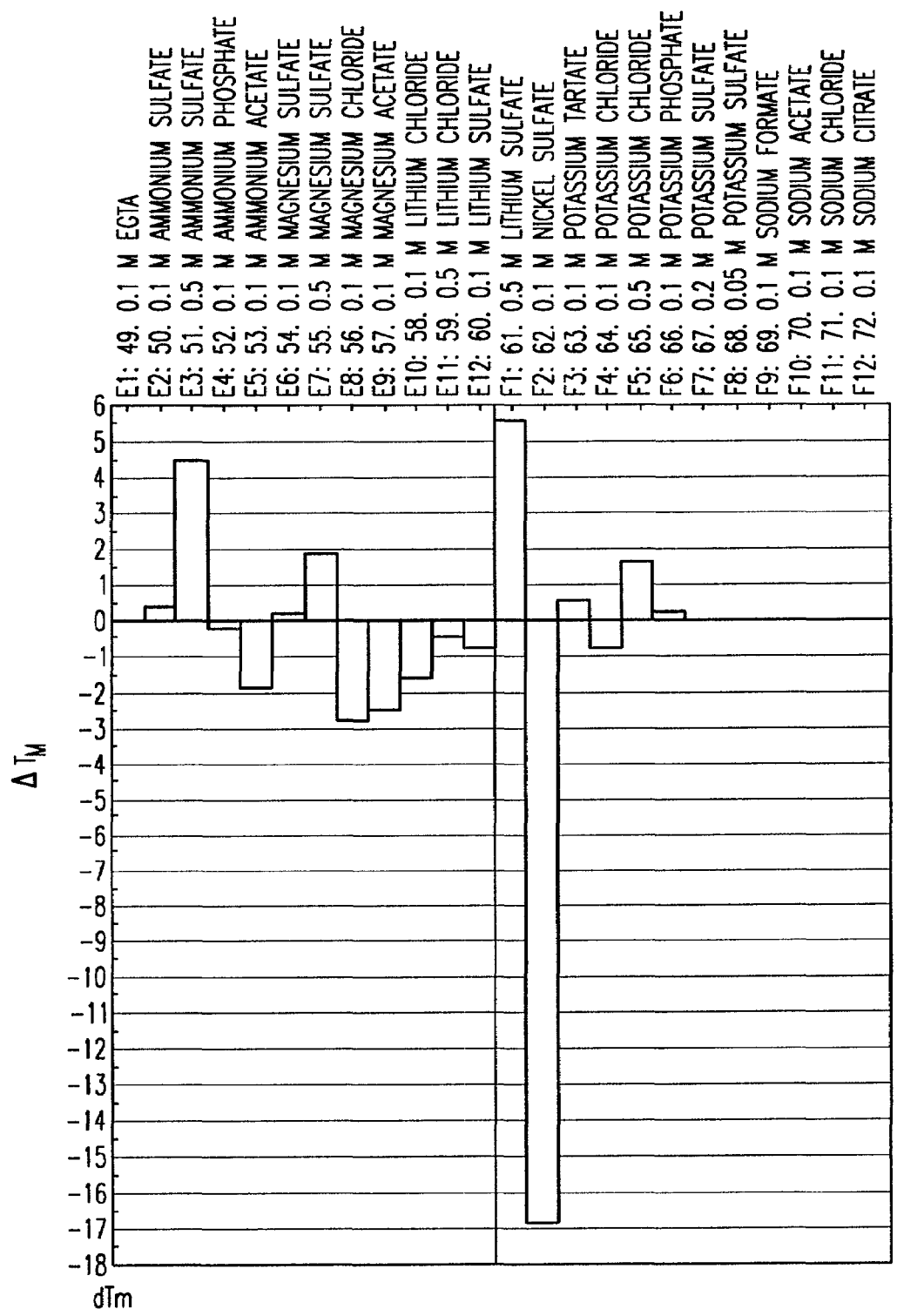
Figure 6D:
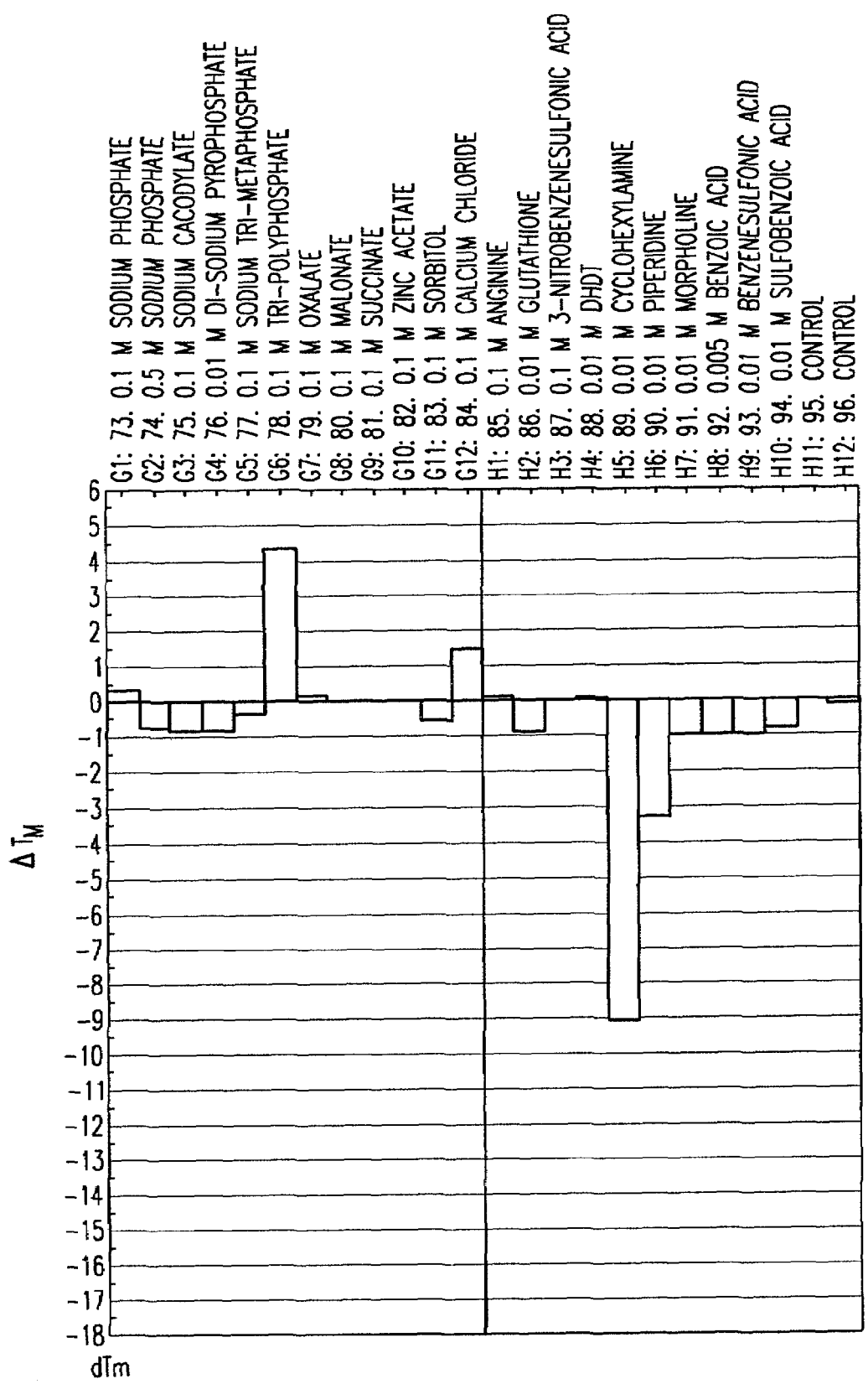
Figure 7A:
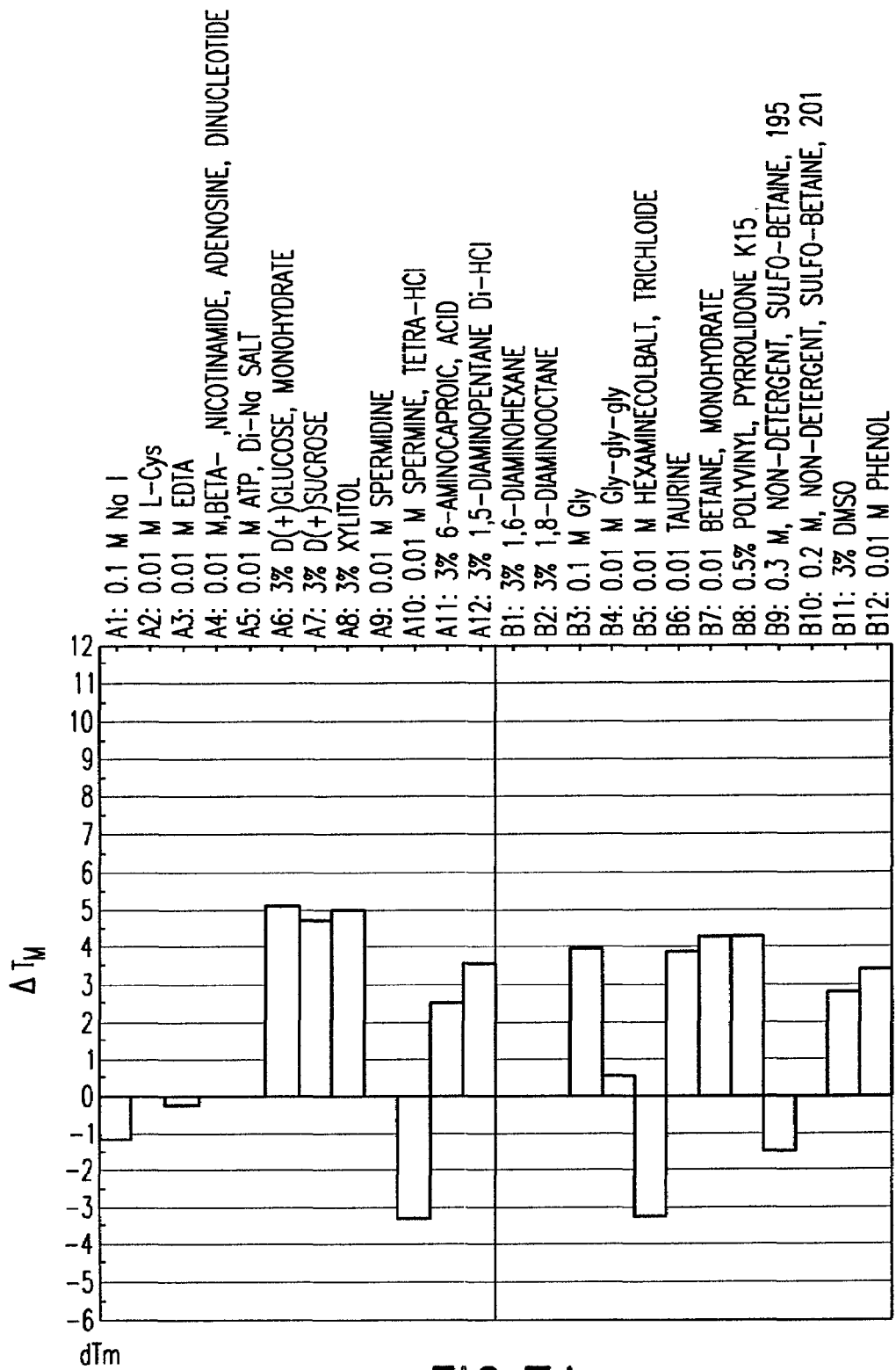
FIGS. 7A–7D show the activity spectrum for fibroblast growth factor receptor 1 (FGFR1) that was generated using the compounds in plate 1 of the functional probe library.
Figure 7B:
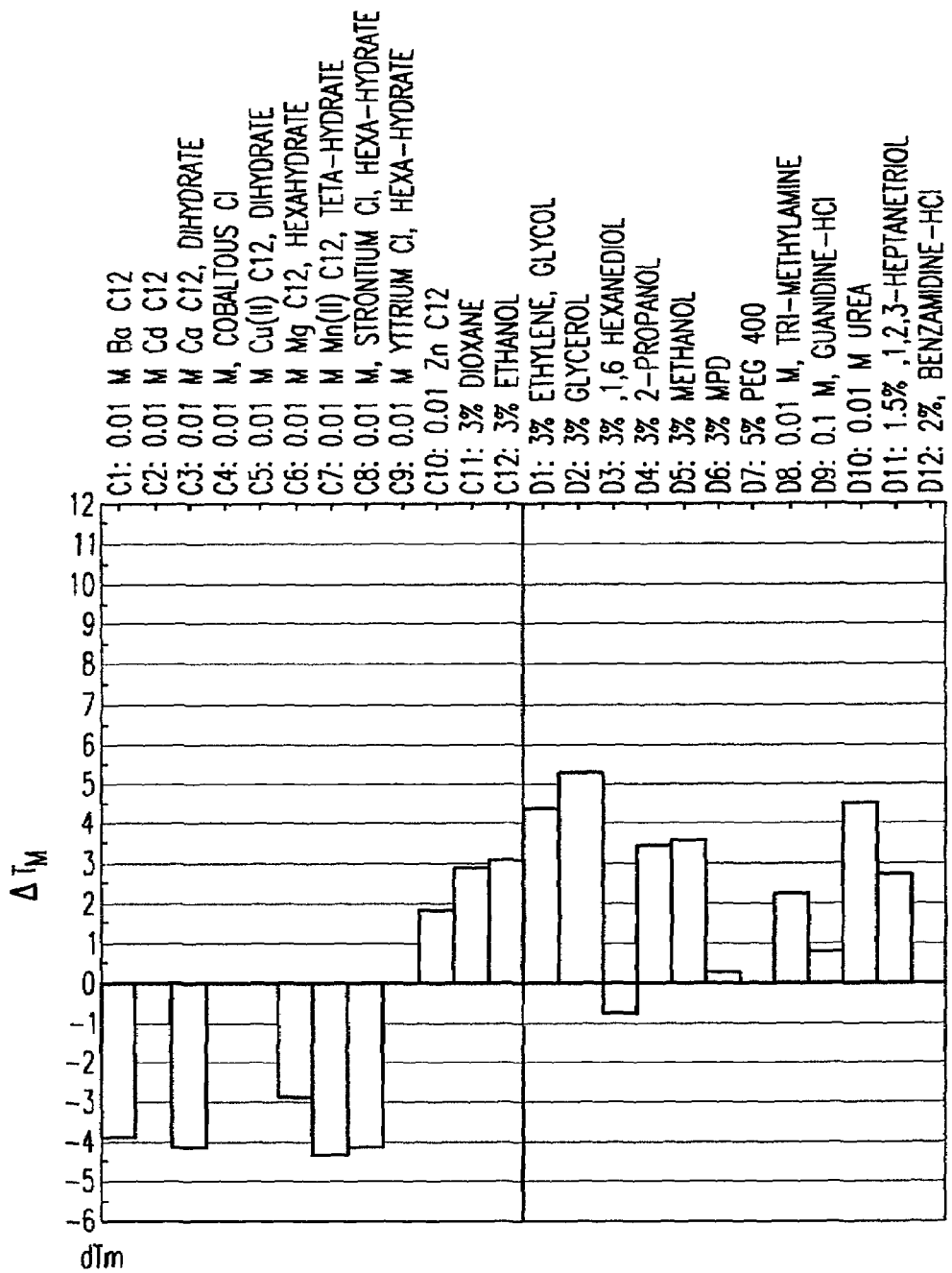
Figure 7C:
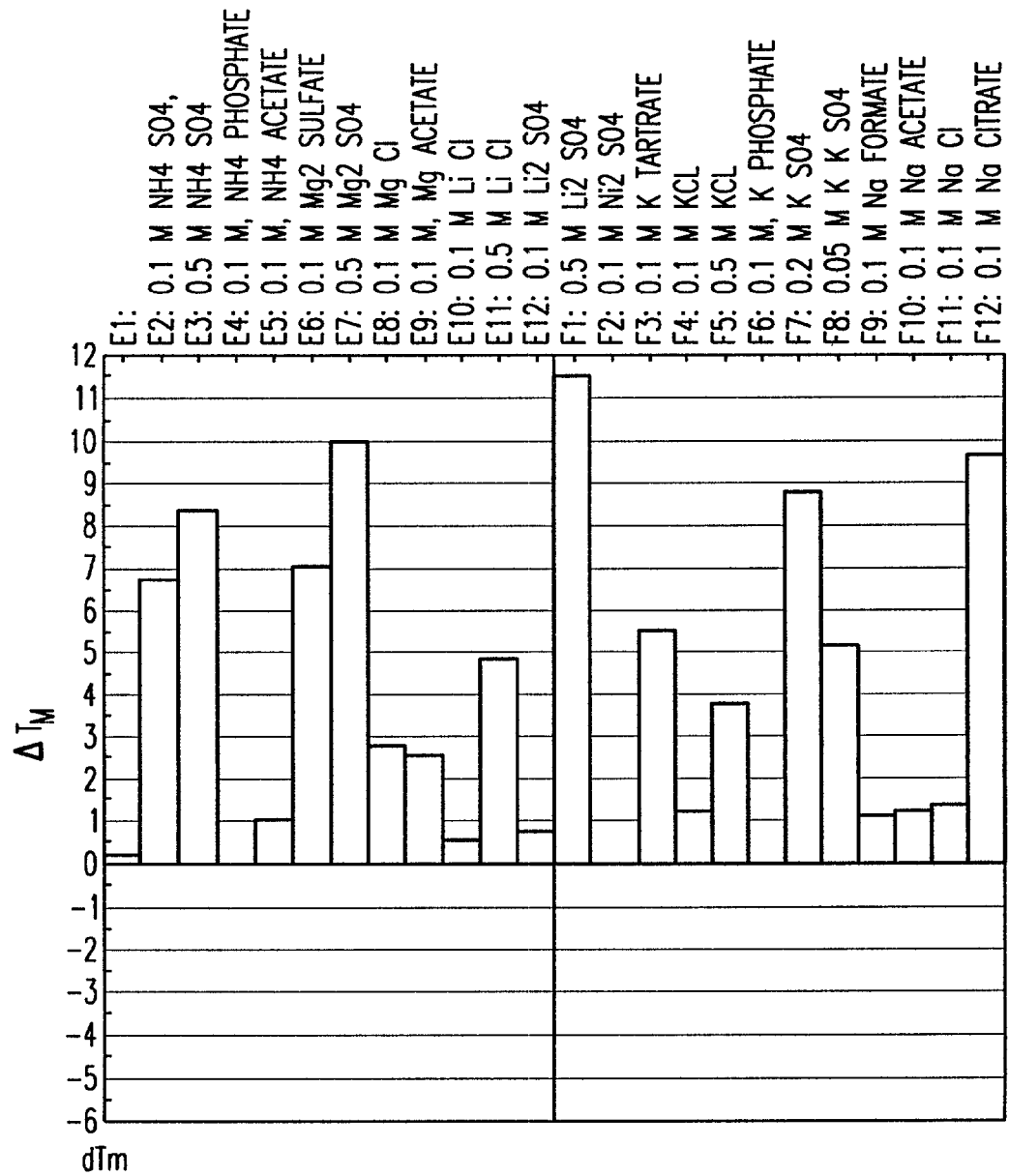
Figure 7D:
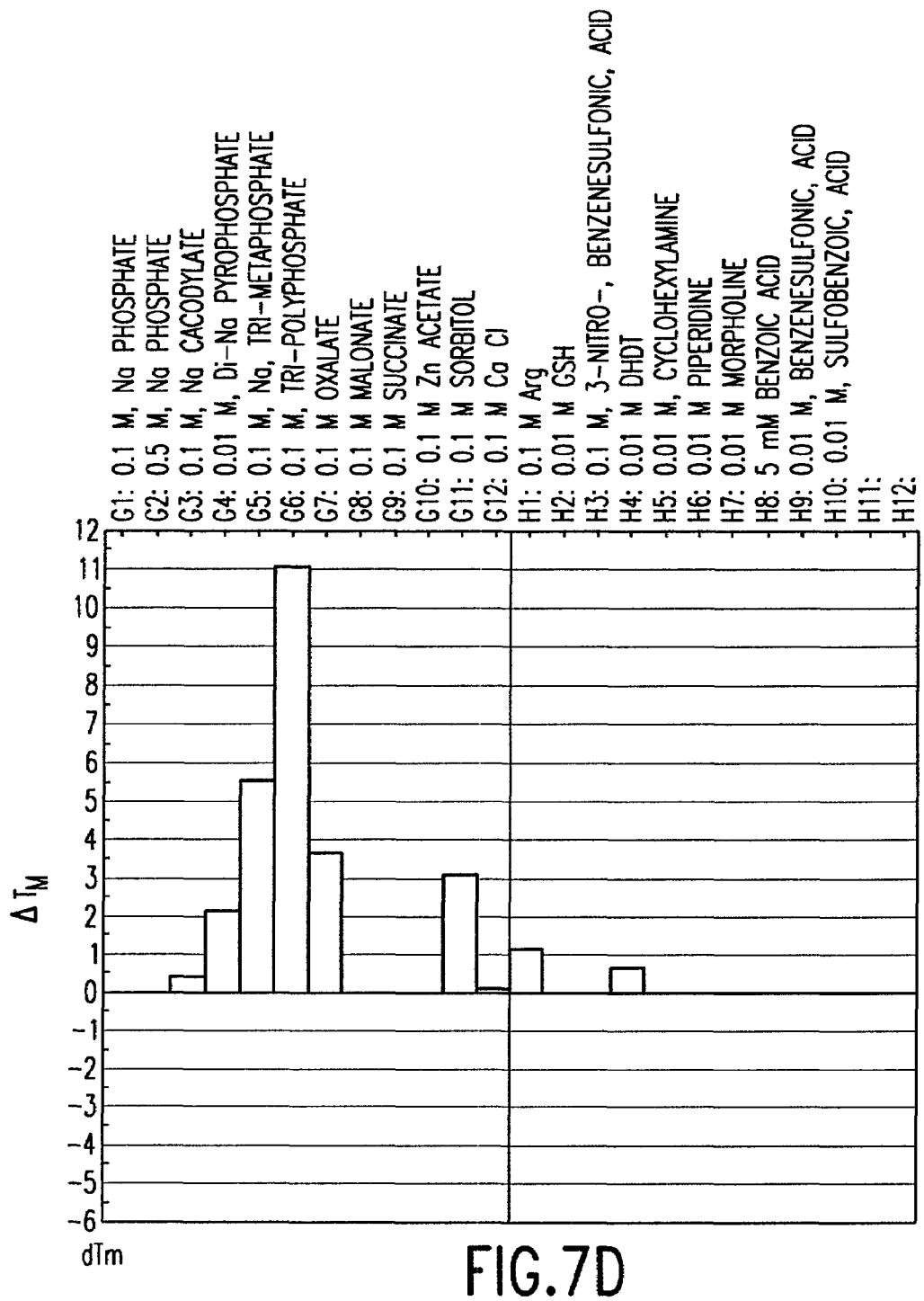

Next, the binding of combinations of two ligands was studied. The data are shown in FIG. 4. The results in FIG. 4 reveal thermal unfolding shifts that are slightly smaller than that expected for full additivity. For example, Hirugen alone gave a $\Delta T_m$ of 5.8.° C., and 3DP-4660 alone gave a $\Delta T_m$ of 7.7° C., but together they gave a $\Delta T_m$ of 12.2° C., and not the 13.5° C. shift that would be expected if the binding energies were fully additive. This result could mean that the binding affinity of one or both ligands is diminished when both ligands are bound to thrombin, and would be an example of negative cooperativity between the fibrin binding site and the catalytic binding site. Such a result is consistent with the thrombin literature, in which the kinetics of hydrolysis of various chromogenic substrates has been found to depend upon ligands binding to exosite I. Indeed, a 60% decrease in $K_m$ for the hydrolysis of D-phenylalanylpipecolyl arginyl-p-nitroanilide was observed when Hirugen was present (Dennis et al., *Eur. J Biochem.* 188: 61–66 (1990)). Moreover, there is also structural evidence for cooperativity between the catalytic site and exosite I. A comparison of the isomorphous structures of PPACK-bound thrombin (PPACK is a thrombin catalytic site inhibitor) and hirugen-bound thrombin revealed conformational changes that occur at the active site as a result of hirugen binding at the exosite I (Vijayalakshmi et al., *Protein Science* 3:2254–2271 (1994)). Thus, the apparent cooperativity observed by between the catalytic center and the exosite I are consistent with functional and structural data in the literature.

One would expect that if the energies of binding of all three ligands were fully additive, a $\Delta T_m$ of 17.7° C. would be seen. However, when all three ligands were present together, the $\Delta T_m$ was 12.9° C. This result implies further negative cooperativity that involves ligand binding at all three protein binding sites. There is some evidence in the literature that is consistent with this supposition. For example, thrombin, in a ternary complex with heparin and fibrin monomer, has decreased activity toward tri-peptide chromogenic substrates and pro-thrombin (Hogg & Jackson, *J. Biol. Chem.* 265:248–255 (1990)), and markedly reduced reactivity with anti-thrombin (Hogg & Jackson, *Proc. Natl. Acad. Sci. USA* 86:3619–3623 (1989)). Also, recent observations by Hotchkiss et al. (*Blood* 84:498–503 (1994)) indicate that ternary complexes also form in plasma and markedly compromise heparin anticoagulant activity.

A summary of the thrombin multi-ligand binding results is shown in Table 3. From the results in FIGS. 3 and 4 and in Table 3, the following conclusions were made. First, in the presence of heparin 5000, hirudin 53–65 bound thrombin about 21 times less tightly than in the absence of heparin; and in the presence of heparin 5000, 3DP-4660 bound thrombin about 10 times less tightly than in the absence of heparin.

Second, in the presence of hirudin 53–65, heparin bound thrombin about 18 times less tightly than in the absence of hirudin 53–65; and in the presence of hirudin 53–65, 3DP-4660 bound thrombin about 3 times less tightly than in the absence of hirudin 53–65.

Third, in the presence of 3DP-4660, heparin bound thrombin about 25% more tightly than in the absence of 3DP-4660; and in the presence of 3DP-4660, hirudin bound thrombin about 2.3 times less tightly than in the absence of 3DP-4660.

TABLE 3

Assay for Ligands Binding to the Active Site, Exosite, and Heparin binding Site of Thrombin

| Protein/Ligand | [Ligand] (µM) | $T_m$ (° K.) | $\Delta T_m$ (° K.) | $K_d$ at $T_m^a$ (nM) | $K_d$ at 298° K.[b] (nM) |
|---|---|---|---|---|---|
| Thrombin (TH) | none | 323.75 | 0.0 | | |
| TH/Heparin 5000 | 200 | 327.95 | 4.2 | 3434 | 470 |
| TH/Hirudin 53-65 | 50 | 329.52 | 5.8 | 185 | 23 |
| TH/3dp-4660 | 50 | 331.40 | 7.7 | 29 | 3 |
| TH/Heparin 5000 | 200 | 327.95 | | | |
| TH/Hep./Hir. | 50 | 330.57 | 2.6 | 4254 | 478 |
| TH/Heparin 5000 | 200 | 327.95 | | | |
| TH/Hep./3dp 4660 | 50 | 333.20 | 5.3 | 350 | 32 |
| TH/Hirudin 53-65 | 50 | 329.52 | | | |
| TH/Hir./Hep. | 200 | 330.57 | 1.1 | 75422 | 8467 |
| TH/Hirudin 53-65 | 50 | 329.52 | | | |
| TH/Hir./3dp-4660 | 50 | 335.97 | 6.5 | 117 | 9 |
| TH/3dp-4660 | 50 | 331.40 | | | |
| TH/3dp-4660/ Hep. | 200 | 333.20 | 1.8 | 38205 | 351 |
| TH/dp-4660 | 50 | 331.40 | | | |
| TH/3dp-4660/ Hir. | 50 | 335.97 | 4.6 | 731 | 54 |

[a] Calculations for $K_d$ at $T_m$ were made using equation (1) with $\Delta H_a^{T_0}$ = 200.0 kcal/mole, as observed for pre-thrombin 1 by Leintz et al., Biochemistry 33:5460-5468 (1994), and an estimated $\Delta C_{pM}$ = 2.0 kcal/mole - ° K.; and $K_d$ = 1/$K_a$.
[b] Estimates for $K_d$ at T = 298° K. were made using the equation (3), where $\Delta H_L^T$ is estimated to be −10.0 kcal/mole.

Thus, the microplate thermal shift assay offers many advantages for analyzing multi-ligand binding interactions in functional genomics classification studies. For example, the same assay can simultaneously detect the binding of different kinds of ligands that bind at multiple binding sites on a target protein. Each ligand binding interaction identified aids the user in assigning a function to a protein. When the functions are summed up, one obtains a response curve that is characteristic of a particular class of proteins.

For example, if one considers the information obtained here for thrombin, and for the moment forget what is known about this protein, the heparin binding data might suggest an extracellular role for this protein since heparin and other sulfated oligosaccharide are important components of the extracellular matrix of the tissues of higher organisms. The catalytic binding site ligand, 3DP-4660, is a non-peptide mimic of a peptide that has an arginyl side chain at the PI position, characteristic of substrates and inhibitors of trypsin-like serine proteases. Similarly, boroarginine transition state analogs, which have an arginine group in the PI position for this synthetic peptide mimic, were found to be specific inhibitors for the serine proteases, thrombin, trypsin, and plasmin (Tapparelli et al., *J. Biol. Chem.* 268:4734–4741 (1993)) with the observed specificity: $K_d$~10 nM (thrombin), $K_d$~1,000 nM (trypsin), $K_d$~10,000 nM (plasmin). Thus, the combined knowledge of heparin binding with the observed binding to boroarginine transition state analogs would quickly focus the assignment of this protein to an extracellular proteolytic function in the absence of any other information.

Further, the microplate thermal shift assay can be used, in a high throughput fashion, to detect cooperativity in ligand binding. Information about ligand binding cooperativity can be collected and analyzed very quickly, over a few hours, rather than over several months, as is required when conventional methods are used to classify protein function.

EXAMPLE 3

Functional Probe Library Screen Against Human Factor Xa

A functional probe library is shown in FIGS. 5A–5D. A 96 well plate (Plate 1) contained 94 compounds (and two control wells) and included many compounds that are considered useful for providing information about the ligand binding preferences, and thus probable function, of proteins. For example, cofactors such as NAD and ATP are found in wells A4 and A5, respectively. This particular plate also contained a great many metal ion binding conditions to help probe a target protein for metal ion cofactors.

In order to validate the functional probe screen, two known proteins were incubated with the compounds of Plate 1 and were then assayed using the microplate thermal shift assay. For example, the activity spectrum obtained for Factor Xa (Enzyme Research Labs) is shown in FIGS. 6A–6D.

Factor Xa was purchased from Enzyme research Labs (South Bend, Ind.). Reactions were prepared in 96-well polycarbonate microtitre plate v-bottom wells. The final concentration of Factor Xa was 1.4 µM (55 ng/mL) in 200 mM Tris.HCl, pH 8. The final concentration of 1,8-ANS was 100 µM. The final concentration of each of the molecules tested for binding is shown in FIGS. 6A–6D. The contents were mixed by repeated uptake and discharge in a 100 µL pipette tip. Finally, one drop of mineral oil (Sigma, St. Lois, Mo.) was added on top of each reaction well to reduce evaporation from samples at elevated temperatures.

The microplate reactions were heated simultaneously, in two degree increments, from 40 to 70° C., using a RoboCycler Gradient Temperature Cycler (Stratagene, La Jolla, Calif.). After each heating step, prior to fluorescence scanning, the sample was cooled to 25 ° C. Fluorescence was measured using a CytoFluor II fluorescence microplate reader (PerSeptive Biosystems, Framingham, Mass.). 1,8-ANS was excited with light at a wavelength of 360 nm. The fluorescence emission was measured at 460 nm.

There were found to be six conditions that stabilized this enzyme with a $\Delta T_m$ of greater than 1.0° C.: (1) 0.5 M $(NH_4)_2SO_4$, (2) 0.5 $MgSO_4$, (3) 0.5 M $Li_2SO_4$, (4) 0.5 M KCl (5) 0.1 M tri-polyphosphate, and (6) 0.1 M $CaCl_2$. The last two conditions are probably most significant, since tri-polyphosphate is a polyelectrolyte that mimics heparin and other sulfated oligosaccharides, and its binding to proteins suggests the presence of a heparin binding site, something that is well known for Factor Xa. Similarly, $Ca^{2+}$ is known to bind to the Gla domain of Factor Xa, which is consistent with the stabilizing effect seen for 0.1 M $CaCl_2$.

Some of metal ions were found to have a strong destabilizing effect on Factor Xa. For example, $[Co(NH_3)_6]Cl_3$, $BaCl_2$, $CdCl_2$, $YCl_2$, and $NiSO_4$ were observed to destabilize Factor Xa by from 6 to 17° C. The reason for this destabilizing effect is unknown. It is possible that these metal ions preferentially bind to the unfolded form of Factor Xa. Some interference with the fluorescence probe is also possible.

EXAMPLE 4

Functional Probe Library Screen Against Human D(II) FGFR1

The compounds in functional probe library Plate 1 was also employed to generate an activity spectrum for D(II) FGFR1. D(II) FGFR1 was cloned and expressed in *E. coli*. Recombinant D(II) FGFR1 was renatured from inclusion bodies essentially as described (Wetmore, D. R. et al., Proc. Soc. Mtg., San Diego, Calif. (1994)), except that a hexahistidine tag was included at the N-terminus to facilitate recovery by affinity chromatography on a $Ni^{2+}$ chelate column (Janknecht, R. et al., *Natl. Acad Sci. USA* 88:8972–8976 (1991)). D(II) FGFR1 was further purified on a heparin-sepharose column (Kan, M. et al., *Science* 259: 1918–1921 (1993); Pantoliano, M. W. et al., *Biochemistry* 33:10229–10248 (1994)). Purity was >95%, as judged by SDS-PAGE. The D(II) FGFR1 protein was concentrated to 12 mg/mL (~1 mM) and stored at 4° C.

Reactions were prepared in 96-well polycarbonate microtitre plate v-bottom wells. The final concentration of D(II) FGFR1 was 50 µM in 200 µM Tris.HCl, pH 8 in each well of a 96-well polycarbonate microtitre plate. The final concentration of 1,8-ANS was 100 µM. The final concentration of each of the molecules tested for binding is shown in FIGS. 7A–7D. The contents were mixed by repeated uptake and discharge in a 100 µL pipette tip. Finally, one drop of mineral oil (Sigma, St. Lois, Mo.) was added on top of each reaction well to reduce evaporation from samples at elevated temperatures.

The microplate reactions were heated simultaneously, in two degree increments, from 25 to 60° C., using a RoboCycler® Gradient Temperature Cycler (Stratagene, La Jolla, Calif.). After each heating step, prior to fluorescence scanning, the sample was cooled to 25 ° C. Fluorescence was measured using a CytoFluor II fluorescence microplate reader (PerSeptive Biosystems, Framingham, Mass.). 1,8-ANS was excited with light at a wavelength of 360 nm. The fluorescence emission was measured at 460 nm.

The resultant activity spectrum is shown in FIGS. 7A–7D. A larger number of compounds were found to stabilize D(II) FGFR1. For example, all of the sugars, D(+)-glucose, D(+)-sucrose, xylitol, and sorbitol were all found to stabilize (and presumably bind) to D(II) FGFR1. This result may be consistent with the known heparin binding properties of this protein. Tri-polyphosphate, a known polyelectrolyte heparin mimic, yielded the largest shift: about 11° C. This result is consistent with the heparin binding properties of this protein (Pantoliano, M. W. et al., *Biochemistry* 33:10229–10248 (1994)).

Thus, in a situation where a user did not know anything about this protein (as is typically the case when a new gene is cloned and the function of the encoded protein is unknown), the information obtained by screening just the compounds in Plate 1 would have provided a user some evidence that D(II)FGFR1 could be classified as a heparin-binding protein.

EXAMPLE 5

Identification of Protein Targets containing DNA Binding Sites

The lac repressor is normally tetrameric protein, a dimer of dimers. However, this protein has been shown to bind to DNA in its dimeric state. Lewis et al. solved the crystal structure of Lac repressor bound to its cognate DNA ligand (Lewis et al., 1996, *Science* 271:1247–1254). A genetically altered dimer, one that is unable to form a tetramer, and a synthetic 21-mer oligonucleotide, the palindromic sequence of the native lac operator, were obtained from Dr. Mitch Lewis at the University of Pennsylvania. Binding of the synthetic lac operator to the mutant lac repressor was assayed using the microplate thermal shift assay.

The final concentration of lac repressor was 60 µM in 200 mM Tris.HCl, pH 8. Reactions were prepared in 96-well polycarbonate microtiter plate V-bottom wells. The final concentration of 1,8-ANS was 100 µM. The final concentration of each of the molecules tested for binding is shown in FIGS. 7A–7D. The contents were mixed by repeated uptake and discharge in a 100 µL pipette tip. Finally, one drop of mineral oil (Sigma, St. Lois, Mo.) was added on top of each reaction well to reduce evaporation from samples at elevated temperatures.

The microplate reactions were heated simultaneously, in two degree increments, from 25° C. to 75° C., using a ROBOCYCLER® Gradient Temperature Cycler (Stratagene, La Jolla, Calif.). After each heating step, prior to fluorescence scanning, the sample was cooled to 25° C. Fluorescence was measured using a CytoFluor II fluorescence microplate reader (PerSeptive Biosystems, Framingham, Mass.). ANS was excited with light at a wavelength of 360 nm. The fluorescence emission was measured at 460 nm.

Figure 8:
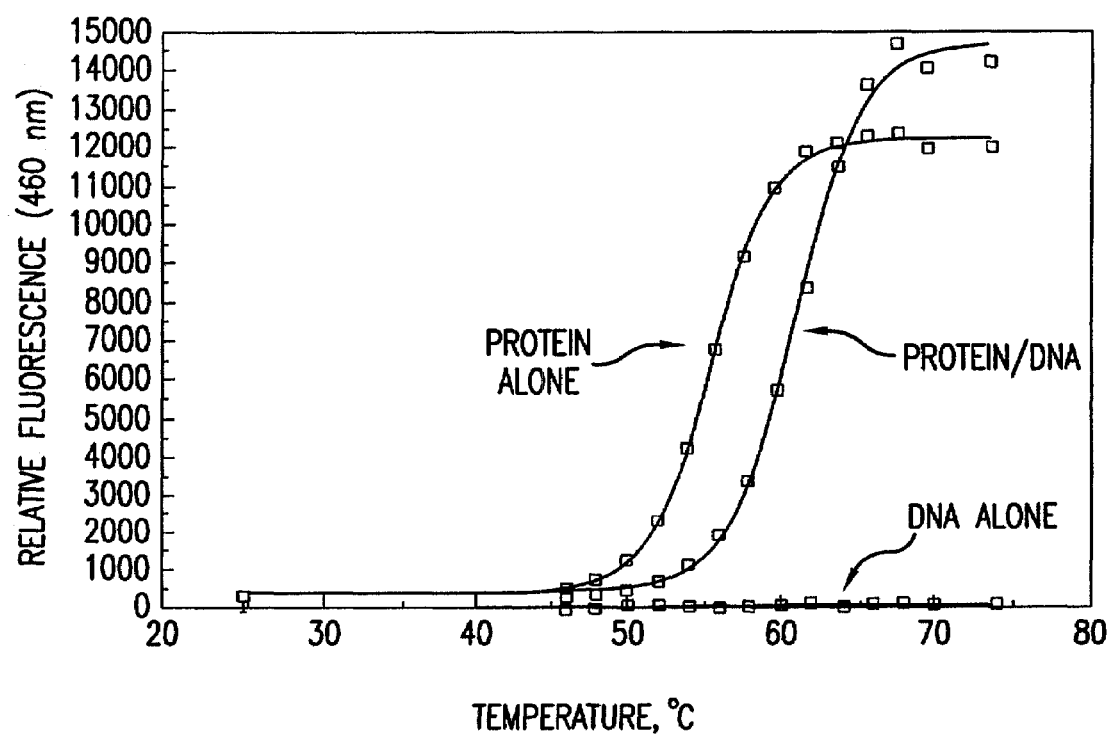
FIG. 8 shows the result of a microplate thermal shift assay of the recombinant dimeric lac repressor binding to a synthetic 21-mer palindromic lac operator sequence.

In the presence of 80 µM synthetic operator DNA, the $T_m$ for the unfolding transition of lac repressor was shifted 5.6° C. (FIG. 8). The calculated $K_d$ at $T_m$ is 6 µM. Using educated guesses for $\Delta H_L$ (−10.0 kcal/mol), the calculated $K_d$ at 25° C. is 1.2 µM and the calculated $K_d$ at physiological temperature (37° C.) is 3.4 µM. The fluorescent probe, 1,8-ANS, did not bind to DNA alone (i.e., there was no fluorescence signal for the control reaction in which no lac repressor was included).

These results show that the microplate thermal shift assay can be used to assay DNA/protein interactions.

EXAMPLE 6

Assays of ATP Binding

Adenosine triphosphate (ATP) and ATP analogue binding can be assayed using the microplate thermal shift assay. Bovine muscle myosin (Sigma), bovine heart 3'–5' cAMP-dependent protein kinase (Sigma), and chicken muscle pyruvate kinase (Sigma) were each dissolved in Buffer A to generate stock solutions at a final concentration of 2 mg/mL. Magnesium chloride ($MgCl_2$), adenosine triphosphate, adenosinetriphosphate-γ-S (ATP-γ-S), aluminum trifluoride ($AlF_3$), and sodium fluoride (NaF) were dissolved in Buffer A (50 mM HEPES, pH 7.5, 100 mM NaCl) to the stock concentrations used in each experiment. Dapoxyl™ 12800 solution was prepared by diluting a stock of 20 MM Dapoxyl 12800™ (5-(4"-dimethylaminophenyl)-2-(4'-phenyl)oxazole sulfonic acid, sodium salt, Molecular Probes, Inc.) in dimethyl sulfoxide to the appropriate concentration in Buffer A.

In the ATP and ATP-γ-S reactions, each sample contained 12 µL of protein stock solution (2 mgs/mL), 9.6 uL of either ATP or ATP-γ-S (50 mM), 4.8 µL of $MgCl_2$ (100 mM) and 21.6 µL of a solution of 222 uM of dapoxyl 12800 in Buffer A. In the ATP, aluminum trifluoride, and sodium fluoride reactions, each sample contained 12 µL of protein stock solution (2 mgs/mL), 9.6 uL of ATP (50 mM), 9.6 mL of aluminum trifluoride (50 mM)+sodium fluoride (50 mM), 4.8 µL of 100 mM $MgCl_2$, and 12 µL of a solution of 400 uM Dapoxyl 12800 in Buffer A.

For the thermal shift assay, four 10 µL aliquots of each assay mixture were dispensed into four wells located in different quadrants of an MJ Research 384-well thermocycler plate. 10 µL of mineral oil was then added to each of the four wells to prevent evaporation. Each data point shown was collected by heating the plate at the temperatures shown for three minutes. For example, the plate was heated to a given temperature, and then allowed to cool to 25 ° C. for one minute, followed by UV illumination and collection of the data. Then the plate was heated to the next higher temperature, and so forth. UV illumination was performed using a long wavelength illumination at 200–420 nm, having a peak at 365 nm. Fluorescence was imaged using a CCD camera having a bandpass filter centered at 550 nm.

Figure 9:
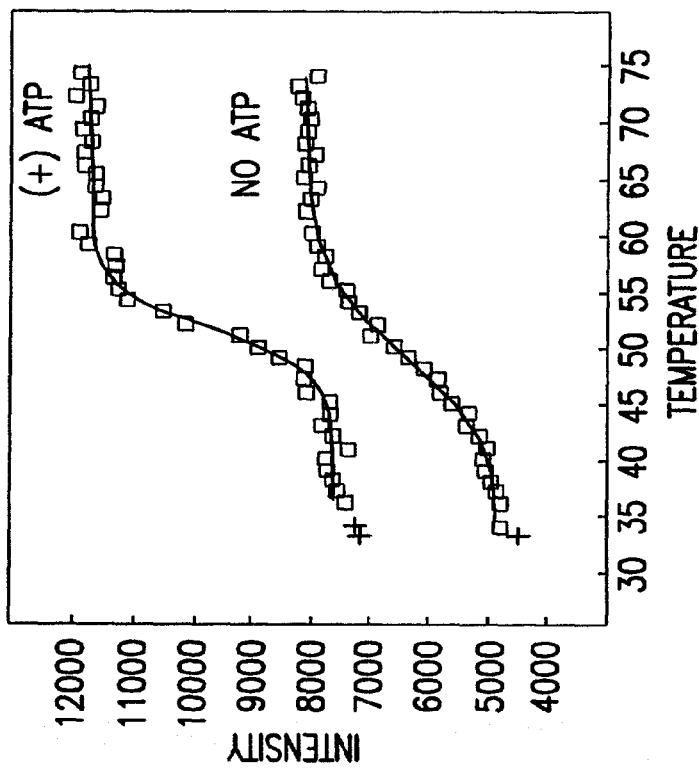
FIG. 9 shows the result of a microplate thermal shift assay of bovine muscle myosin binding to adenosine triphosphate (ATP).

FIG. 9 shows the results of a microplate thermal shift assay of ATP to bovine muscle myosin. The data is plotted as fluorescence intensity as a function of temperature. The $T_m$ of the control thermal unfolding curve (no ATP) was 49.3° C. (microplate well K2). The $T_m$ of the thermal unfolding curve for bovine muscle myosin bound to ATP ((+)ATP) was 51.4° C. (microplate well K16). Thus the $\Delta T_m$ for ATP binding was 2.1° C. The $K_d$ was 440 µM.

Figure 10:
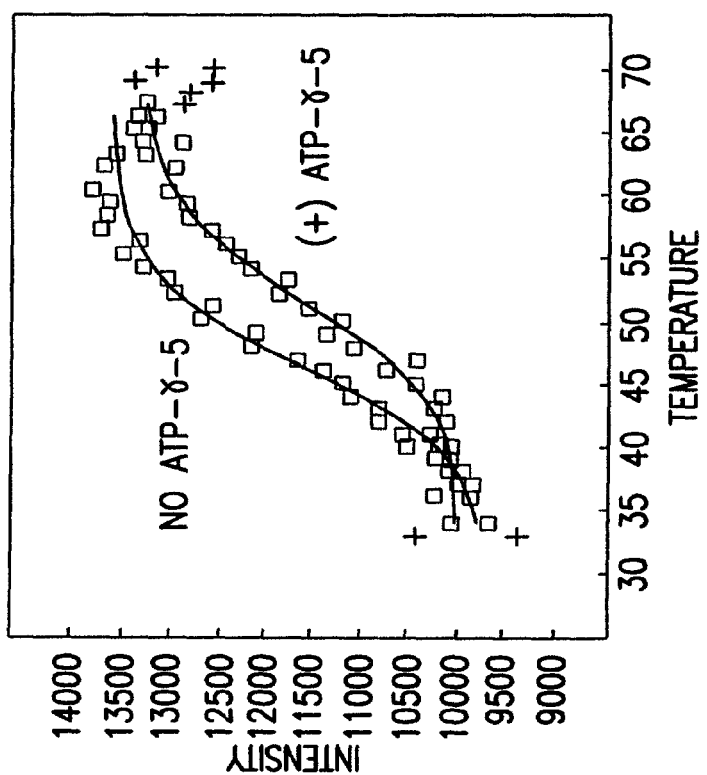
FIG. 10 shows the result of a microplate thermal shift assay of bovine heart 3',5'-cAMP-dependent protein kinase binding to adenosine triphosphate-γ-sulphate (ATP-γ-S).

FIG. 10 shows the result of a microplate thermal shift assay of ATP-γ-S to and 3',5'-cAMP-dependent protein kinase. The data is plotted as fluorescence intensity as a function of temperature. The $T_m$ of the control thermal unfolding curve (no ATP-γ-S) was 46.2° C. (microplate well E14). The $T_m$ of the thermal unfolding curve for 3',5'-cAMP-dependent protein kinase bound to ATP-γ-S ((+) ATP-γ-S) was 51.8° C. (microplate well M15). Thus the $\Delta T_m$ for ATP-γ-S binding was 5.6° C. The $K_d$ was 200 µM. The results, including the results for pyruvate kinase, are summarized in Table 4.

TABLE 4

Summary of results for enzymes that bind to ATP. The value in parentheses is standard deviation.

| Protein | Reference $T_m$ | ATP-γ-S (10 mM) $\Delta T_m$ | ATP (10 mM) $\Delta T_m$ | ATP + $AlF_3$ (10 mM) $\Delta T_m$ |
|---|---|---|---|---|
| Myosin | 49.4 | 0.0 (±0.2) | 2.2 (±0.4) | 2.8 (±0.4) |
| 3'–5' cAMP Protein kinase | 44.7 | 5.6 (±1.7) | 7.5 (±0.7) | 8.2 (±1.4) |
| Pyruvate kinase | 54.5 | 0.8 (±0.11) | −0.44 (±0.1) | −0.27 (±0.2) |

EXAMPLE 7

Assay of Folic Acid Binding

Folic acid binding can be assayed using the microplate thermal shift assay. Bovine liver dihydrofolate reductase (DHFR, Sigma), chicken liver dihydrofolate reductase (DHFR, Sigma), pigeon liver arylamine acetyltransferase (ArAcT, Sigma), and porcine liver formimino glutamic acid transferase (FGT, Sigma) were each dissolved in Buffer A (50 mM HEPES, pH 7.5, 100 mM NaCl) to generate stock solutions at a final concentration of 2 mg/mL. Solutions of dihydrofolic acid ($FAH_2$), methotrexate, nicotinamide adenine dinucleotide phosphate (NADP), were prepared by dissolving solid material into Buffer A immediately prior to use. Dapoxyl™ 12800 solution was prepared by diluting a stock of 20 mM Dapoxyl™, 12800 in dimethyl sulfoxide to the appropriate concentration in Buffer A.

Each assay sample contained 12 µL of protein stock solution (2 mg/mL), 4.8 uL of either dihydrofolic acid (FAH$_2$) or methotrexate stock solution (1 mM), and 31.2 µL of a solution of 154 µM Dapoxyl™ 12800 in Buffer A. Each sample contained 12 µL of protein stock solution (2 mgs/mL), 4.8 uL of NADP stock solution (50 mM), and 31.2 µL of a solution of 154 µM Dapoxyl™ 12800 in Buffer A.

For the thermal shift assay, four 10 µL aliquots of each assay mixture were dispensed into four wells located in different quadrants of an MJ Research 384-well thermocycler plate. 10 µL of mineral oil was then added to each of the four wells to prevent evaporation. Each data point shown was collected by heating the plate at the temperature shown for three minutes, followed by incubation at 25° C. for one minute, followed by UV illumination and collection of the data. The results are shown in Table 5.

TABLE 5

Results for proteins that bind methotrexate, FAH$_2$ and NADP. The value in parentheses is standard deviation.

| Protein | Reference $T_m$ | Methotrexate (100 µM) $\Delta T_m$ | FAH$_2$ (100 µM) $\Delta T_m$ | NADP (5 mM) $\Delta T_m$ |
|---|---|---|---|---|
| DHFR | 52.47 | 7.0 (±−0.1) | −0.64 (±0.2) | 3.2 (±0.13) |
| DHFR | 56.6 | 8.6 (±0.2) | 2.5 (±0.2) | 3.8 (±0.4) |
| Arylamine Acetyl transferase | 49.8 | 1.0 (±0.4) | −1.8 (±0.5) | 2.8 (±0.4) |
| Formimino L-Glutamic acid Transferase | 47.2 | 0.9 (±0.5) | 3.62 (±0.4) | 0.0 (±0.2) |

EXAMPLE 8

Assay of Methotrexate/NADP(H) Binding

The ability to measure temperature shifts for the binding of methotrexate and NADPH, both separately and simultaneously, is another example of the utility of the present invention in measuring milti-ligand binding interactions. In this case, the binding sites of the two ligands are proximal, and there is positive cooperativity in the binding of the two ligands, as shown by the fact that thermal shift for both ligands binding simultaneously is 2–4 degrees more than the total of shifts for each ligand binding separately (Table 6).

Methotrexate (MTX) and NADPH binding can be assayed using the microplate thermal shift assay. Bovine liver dihydrofolate reductase (DHFR, Sigma) and chicken liver dihydrofolate reductase (DHFR, Sigma were each dissolved in Buffer A (50 mM HEPES, pH 7.5, 100 mM NaCl) to generate stock solutions at a final concentration of 2 mg/mL. All stock solutions of ligands were prepared by dissolving solid material in Buffer A immediately prior to use. Stock solutions of nicotinamide adenine dinucleotide phosphate-reduced form (NADPH, 100 mM), NADP (100 mM), and methotrexate (1 mM) were diluted further in Buffer A to twice to the final assay concentration (2×stocks): methotrexate (200 µM), NADP (20 mM), NADPH (20 mM), methotrexate +NADP (200 µM+20 mM), methotrexate+NADPH (200 µM+20 mM). Dapoxyl™ 12800 solutions was prepared by diluting a stock of 20 mM Dapoxyl™ 12800 in dimethyl sulfoxide to the appropriate concentration in Buffer A. 5 µL of each protein stock solution was added to 25 µL of 2×ligand stock solution mixed with 20 µL of a solution of 250 µM Dapoxyl™ 12800 in Buffer A.

The final ligand concentrations were 10 mM NADP; 10 mM NADPH; and 100 µM MTX.

For the thermal shift assay, four 10 µL aliquots of each assay mixture were dispensed into four wells located in different quadrants of an MJ Research 384-well thermocycler plate. 10 µL of mineral oil was then added to each of the four wells to prevent evaporation. Each data point shown was collected by heating the plate at the temperature shown for three minutes, followed by incubation at 25 ° C. for one minute, followed by UV illumination and collection of the data.

Figure 11:
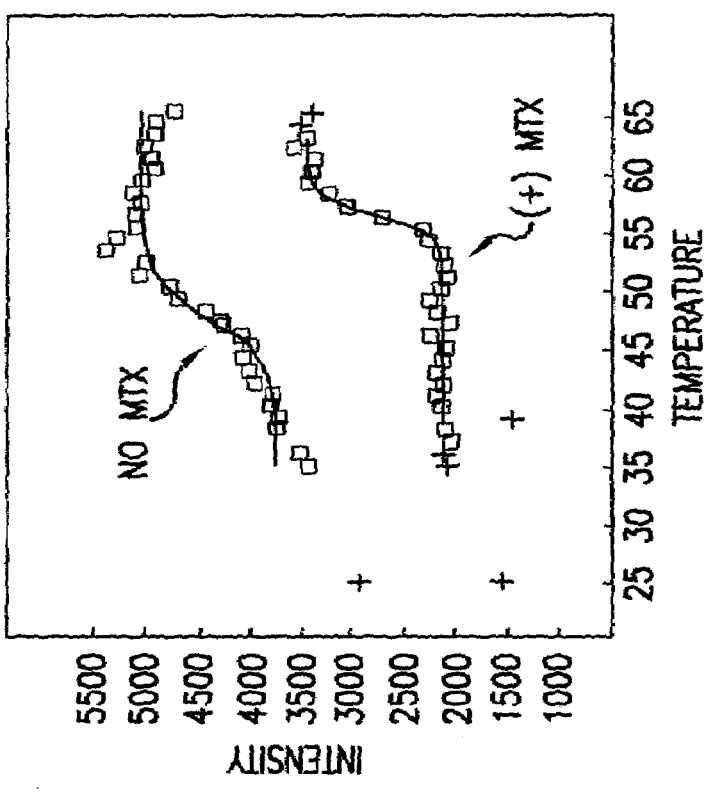
FIG. 11 shows the result of a microplate thermal shift assay of bovine dihydrofolate reductase (DHFR) binding to methotrexate.

FIG. 11 shows the result of a microplate thermal shift assay of methotrexate to dihydrofolate reductase. The data is plotted as fluorescence intensity as a function of temperature. The $T_m$ of the control thermal unfolding curve (no MTX) was 47.2° C. (microplate well M1). The $T_m$ of the thermal unfolding curve for DHFR bound to methotrexate ((+) MTX) was 56.4° C. (microplate well G6). Thus the $\Delta T_m$ for methotrexate binding was 9.2° C. The $K_d$ was 24 nM.

Figure 12:
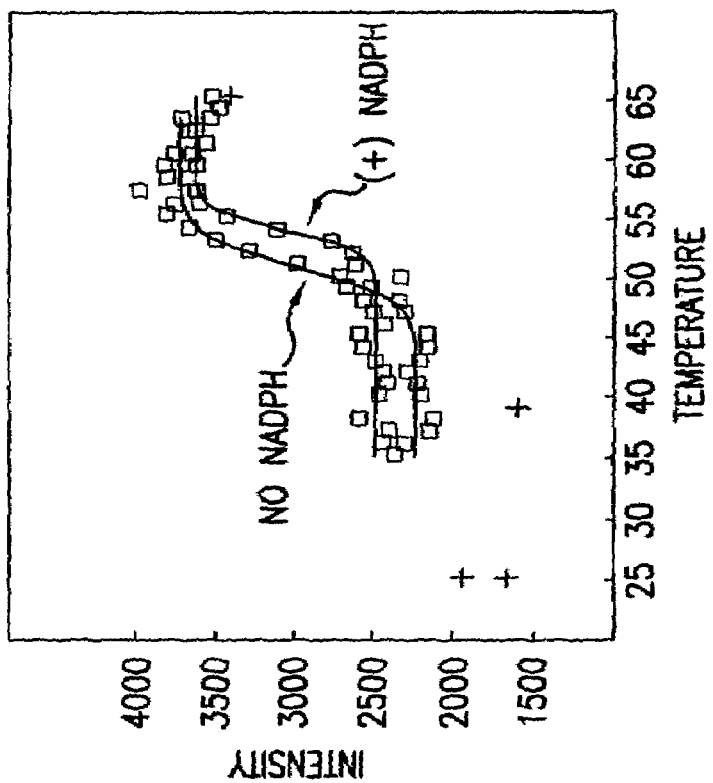
FIG. 12 shows the result of a microplate thermal shift assay of bovine dihydrofolate reductase (DHFR) binding to NADPH.

FIG. 12 shows the result of a microplate thermal shift assay of NADPH to dihydrofolate reductase. The data is plotted as fluorescence intensity as a function of temperature. The $T_m$ of the control thermal unfolding curve (no NADPH) was 50.8° C. (microplate well G8). The $T_m$ of the thermal unfolding curve for DHFR bound to NADPH ((+) NADPH) was 53.8° C. (microplate well B20). Thus the $\Delta T_m$ for NADPH binding was 3.° C. The $K_d$ was 0.7 µM.

TABLE 6

$\Delta T_m$'s of ligand complexed with DHFR. The value in parentheses is standard deviation.

| Protein | NADP | MTX | Sum[a] | NADP + MTX[b] | NADPH | MTX | Sum[a] | NADPH + MTX[b] |
|---|---|---|---|---|---|---|---|---|
| DHFR (chicken) | 7.5 (±0.38) | 10.1 (±0.32) | 17.6 | 20.9 (±0.4) | 11.9 (±1.3) | 10.1 (±0.32) | 22 | 23.8 (±0.4) |
| DHFR (cow) | 6.3 (±0.1) | 7.7 (±0.3) | 14 | 18.1 (±0.4) | 9.7 (±0.2) | 7.7 (±0.3) | 17.4 | 24.6 (±0.6) |

[a]The value shown is the sum of the individual $\Delta T_m$'s observed from the protein incubated separately with each ligand.
[b]The value shown is the $\Delta T_m$ observed when the protein was incubated simultaneously with both ligands.

EXAMPLE 9

Dihydrofolic acid is a substrate of dihydrofolate reductase (DHFR). Methotrexate is a folic acid analog that binds to DHFR. As evidence that the method of the present invention is reliable, it was shown that the method can be used to detect binding of dihydrofolic acid to DHFR. Bovine liver DHFR was combined with 80 compounds to screen for the function of the protein, and binding to methotrexate, but not to a number of other compounds, was detected.

Each well of microsource compound plate #198104 contained one of 80 different compounds at a concentration 10 mM in dimethyl sulfoxide. Each compound solution was diluted in Buffer A (50 mM HEPES, pH 7.5, 100 mM NaCl) to a final concentration of 200 µM in separate wells in a 384-well polystyrene plate. 5 µL of the solution contained in each well was transferred to an MJ research polypropylene plate containing 5 µL of bovine liver DHFR (at a concentration of 0.5 mg/mL and Dapoxyl™ 12800 dye at a concentration of 200 µM, yielding final concentrations of 100 µM ligand, 0.25 mg/mL DHFR, and 100 µM dapoxyl in the 10 L volume of each well.

10 µL of mineral oil was added to each well to prevent evaporation. Thermal unfolding profiles were then measured for each well from 25 to 70° C., by collecting data points at each temperature, separated by one-degree increments. Each data point was collected by heating the plate at the temperature shown for 3 minutes, followed by incubation at 25° C. for one minute, followed by long-wavelength UV illumination and collection of the data using a CCD camera.

The data were collected as four replicates of 80 compounds in the quadrants of a 384-well plate. The four quadrants consist of: wells A2 through H11 (first quadrant), wells A14 through H23 (second quadrant), wells I2 through P11 (third quadrant), and wells I14 through I23 (fourth quadrant). Columns 1, 12, 13, and 24 consist of reference wells containing only DHFR and dimethyl sulfoxide.

Wells F2, F14, N2, and N14 contained methotrexate. Binding was revealed by fitting software as a red well. Methotrexate shifted the $T_m$ by 5.13±0.19 degrees (average of 4 quadrants), and the other compounds on the plate had little or no effect (shown as near-white wells). These results which indicated that DHFR binds methotrexate.

All publications and patents mentioned hereinabove are hereby incorporated in their entireties by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. A method for determining at least one previously unidentified biological function of a target protein comprising:
   (a) screening a multiplicity of different molecules for their ability to modify the stability of a target protein, wherein modification of the stability of said target protein by a molecule indicates that the molecule binds to said target protein; wherein said screening step (a) comprises:
   (a1) contacting said target protein with one or more of said multiplicity of different molecules in each of a multiplicity of containers;
   (a2) treating said target protein in each of said multiplicity of containers to cause said target protein to unfold;
   (a3) measuring in each of said containers a physical change associated with the unfolding of said target protein;
   (a4) generating an unfolding curve for said target protein for each of said containers; and
   (a5) comparing each of said unfolding curves in step (a4) to (1) each of said other unfolding curves and to (2) the unfolding curve obtained for said target protein in the absence of any of said multiplicity of different molecules; and
   (a6) determining whether any of said multiplicity of different molecules modifies the stability of said target protein, wherein a modification in stability is indicated by a change in said unfolding curve
   (b) generating, from step (a), a first list of molecules that modify the stability of said target protein;
   (c) comparing said first list from step (b) to at least one second list of molecules, wherein said second list of molecules are known to modify the stability of a group of proteins which share biological function; and
   (d) determining if any molecule in said first list from step (b) is included in said second list from step (c), thereby determining at least one previously unidentified biological function of said target protein.

2. A method for determining at least one previously unidentified biological function of a target protein comprising:
   (a) screening a multiplicity of different molecules for their ability to shift the thermal unfolding curve of a target protein, wherein a shift in the thermal unfolding curve of said target protein by a molecule indicates that the molecule binds to said target protein;
   (b) generating, from step (a), a first list of molecules that shift the thermal unfolding curve of said target protein;
   (c) comparing said first list from step (b) to at least one second list of molecules, wherein said second list of molecules are known to modify the stability of a group of proteins which share biological function; and
   (d) determining if any molecule in said first list from step (b) is included in said second list from step (c), thereby determining at least one previously unidentified biological function of said target protein.

3. The method of claim 2, wherein said screening step (a) comprises:
   (a1) contacting said protein with one or more of said multiplicity of different molecules in each of a multiplicity of containers;
   (a2) heating said multiplicity of containers from step (a1);
   (a3) measuring in each of said containers a physical change associated with the thermal unfolding of said target protein resulting from said heating;
   (a4) generating a thermal unfolding curve for said target protein as a function of temperature for each of said containers; and
   (a5) comparing each of said unfolding curve in step (a4) to (1) each of said other thermal unfolding curves and to (2) the thermal unfolding curve obtained for said protein in the absence of any of said multiplicity of different molecules; and
   (a6) determining whether any of said multiplicity of different molecules shift the thermal unfolding curve of said protein.

4. The method of claim 3, wherein said comparing step (a5) comprises ranking said molecules in said multiplicity of different molecules for binding to said target protein according to the ability of each of said multiplicity of different molecules to shift the thermal unfolding curve of said target protein.

5. The method of claim 3, wherein in said heating step (a2), said multiplicity of containers is heated simultaneously.

6. The method of claim 3, wherein said step (a4) further comprises determining a midpoint temperature ($T_m$) from the thermal unfolding curve; and
   wherein said step (a5) further comprises comparing the $T_m$ of each of said unfolding curves in step (a4) to (1) the $T_m$ of each of said other thermal unfolding curves and to (2) the $T_m$ of the thermal unfolding curve obtained for said target protein in the absence of any of said different molecules.

7. The method of claim 3, wherein said step (a3) comprises measuring the absorbance of light by said contents of each of said containers.

8. The method of claim 3, wherein said step (a1) comprises contacting said target protein with a fluorescence probe molecule present in each of said multiplicity of containers and wherein said step (a3) comprises
   (i) exciting said fluorescence probe molecule, in each of said multiplicity of containers, with light; and
   (ii) measuring the fluorescence from each of said multiplicity of containers.

9. The method of claim 8, wherein said step (a3)(ii) further comprises measuring the fluorescence from each of said multiplicity of containers one container at a time.

10. The method of claim 8, wherein said step (a3)(ii) further comprises measuring the fluorescence from a subset of said multiplicity of containers simultaneously.

11. The method of claim 8, wherein said step (a3)(ii) further comprises measuring the fluorescence from each of said multiplicity of containers simultaneously.

12. The method of claim 3, wherein said step (a3) comprises
   (i) exciting tryptophan residues in said target protein, in each of said multiplicity of containers, with light; and
   (ii) measuring the fluorescence from each of said multiplicity of containers.

13. The method of claim 3, wherein said multiplicity of containers in step (a1) comprises a multiplicity of wells in a microplate.

* * * * *